(12) United States Patent
Newman et al.

(10) Patent No.: US 9,862,679 B2
(45) Date of Patent: Jan. 9, 2018

(54) POTENT AND SELECTIVE INHIBITORS OF MONOAMINE TRANSPORTERS; METHOD OF MAKING; AND USE THEREOF

(71) Applicant: THE UNITED STATES OF AMERICA, AS REPRESENTED BY THE SECRETARY, DEPARTMENT OF HEALTH AND HUMAN SERVICES, Washington, DC (US)

(72) Inventors: Amy Hauck Newman, Phoenix, AZ (US); Oluyomi M Okunola-Bakare, Beltsville, MD (US); Jianjing Cao, Ellicott City, MD (US)

(73) Assignee: THE UNITED STATES OF AMERICA, AS REPRESENTED BY THE SECRETARY, DEPARTMENT OF HEALTH AND HUMAN SERVICES OFFICE OF TECHNOLOGY TRANSFER, NATIONAL INSTITUTES OF HEALTH, Washington, DC (US)

( * ) Notice: Subject to any disclaimer, the term of this patent is extended or adjusted under 35 U.S.C. 154(b) by 0 days.

(21) Appl. No.: 14/772,486

(22) PCT Filed: Mar. 7, 2014

(86) PCT No.: PCT/US2014/021514
§ 371 (c)(1),
(2) Date: Sep. 3, 2015

(87) PCT Pub. No.: WO2014/138518
PCT Pub. Date: Sep. 12, 2014

(65) Prior Publication Data
US 2016/0009644 A1    Jan. 14, 2016

Related U.S. Application Data

(60) Provisional application No. 61/774,878, filed on Mar. 8, 2013.

(51) Int. Cl.
| | | |
|---|---|---|
| A61K 31/495 | (2006.01) |
| C07C 323/60 | (2006.01) |
| A61K 45/06 | (2006.01) |
| A61K 31/135 | (2006.01) |
| C07C 317/44 | (2006.01) |
| C07C 317/28 | (2006.01) |
| C07C 323/25 | (2006.01) |
| C07D 295/08 | (2006.01) |
| C07D 295/088 | (2006.01) |
| C07D 295/108 | (2006.01) |
| C07D 295/185 | (2006.01) |

(52) U.S. Cl.
CPC .......... *C07C 323/60* (2013.01); *A61K 31/135* (2013.01); *A61K 45/06* (2013.01); *C07C 317/28* (2013.01); *C07C 317/44* (2013.01); *C07C 323/25* (2013.01); *C07D 295/08* (2013.01); *C07D 295/088* (2013.01); *C07D 295/108* (2013.01); *C07D 295/185* (2013.01); *C07C 2601/02* (2017.05)

(58) Field of Classification Search
USPC .................. 514/249, 255.01, 255.04, 255.06
See application file for complete search history.

(56) References Cited

U.S. PATENT DOCUMENTS

| | | | |
|---|---|---|---|
| 2,483,671 A | 10/1949 | Rieveschl, Jr. et al. |
| 2,618,637 A | 11/1952 | Archer et al. |
| 2,621,214 A | 12/1952 | Deinet |
| 3,043,844 A | 7/1962 | Elpern |
| 3,128,308 A | 4/1964 | Doub et al. |
| 3,238,209 A | 3/1966 | Nakanishi et al. |
| 4,066,686 A | 1/1978 | Lafon |
| 4,177,290 A | 12/1979 | Lafon |
| 4,927,855 A | 5/1990 | Lafon |
| 5,324,728 A | 6/1994 | Sekine et al. |
| 6,387,389 B1* | 5/2002 | Rothman ............. A61K 31/495 424/422 |
| 2005/0222257 A1 | 10/2005 | Rebiere et al. |
| 2008/0319227 A1 | 12/2008 | Liang et al. |

(Continued)

FOREIGN PATENT DOCUMENTS

| | | |
|---|---|---|
| BE | 633453 | 12/1963 |
| CH | 358080 | 12/1961 |
| DE | 4219659 A1 | 12/1993 |

(Continued)

OTHER PUBLICATIONS

Cao; ACS Medicinal Chemistry Letters; 2011, 2, 48-52.*
International Search Report; International Application No. PCT/US2014/021514; International Filing Date Mar. 7, 2014; Date of Mailing Sep. 19, 2014; 7 pages.
Jianjing Cao et al: "SARs at the Monoamine Transporters for a Novel Series of Modafinil Analogues", ACS Medicinal Chemistry Letters, American Chemical Society, US, vol. 2, No. 1, Jan. 13, 2011, pp. 48-52.

(Continued)

*Primary Examiner* — Pancham Bakshi
(74) *Attorney, Agent, or Firm* — Cantor Colburn LLP

(57) ABSTRACT

Disclosed herein are bisarylmethylthioacetamides and bisarylmethylthioethylamines useful as inhibitors of monoamine transporters. The compounds are potent and/or selective inhibitors of dopamine (DA), serotonin (5-HT), and/or norepinephrine (NE) reuptake via their respective transporters, DAT, SERT and NET. Also disclosed are methods for eliciting a wake-promoting or cognitive or attention enhancing effect and for treating substance use disorders, attention deficit (hyperactivity) disorder, depressive disorders, bipolar disorder or other neuropsychiatric disorders sleep disorders or cognitive impairment using the compounds.

16 Claims, 2 Drawing Sheets

(56) References Cited

U.S. PATENT DOCUMENTS

2010/0226943 A1    9/2010  Brennan et al.

FOREIGN PATENT DOCUMENTS

| EP | 0097071 A  | 12/1983 |
| EP | 0097546 B1 | 9/1985  |
| EP | 0256909 A1 | 2/1988  |
| EP | 0318093 A2 | 11/1988 |
| EP | 0399818 A1 | 11/1990 |
| EP | 0458387 A1 | 11/1991 |
| EP | 0528172 A1 | 2/1993  |
| GB | 890732     | 3/1962  |
| NL | 105432     | 7/1963  |
| WO | 9501171 A1 | 1/1995  |
| WO | 03066035 A2| 8/2003  |

OTHER PUBLICATIONS

Loland Claus J et al: "R-modafinil (armodafinil): a unique dopamine uptake inhibitor and potential medication for psychostimulant abuse", Biological Psychiatry, USA, vol. 72, No. 5, Sep. 1, 2012, pp. 405-413.
Written Opinion of the International Searching Authority; International Application No. PCT/US2014/021514; International Filing Date Mar. 7, 2014; Date of Mailing Sep. 19, 2014; 10 pages.
Zhang et al: "Synthesis and biological evaluation of (R)-N-(diarylmethylthio/sulfinyl)ethyl/propyl-piperidine-3-carboxylic acid hydrochlorides as GABA uptake inhibitors", Bioorganic & Med. Chem. Letters, vol. 17, No. 13, Jul. 1, 2007, pp. 3769-3773.
International Preliminary Report on Patentability; International Application No. PCT/US2014/021514; International Filing Date Mar. 7, 2014; Date of Issurance Sep. 8, 2015; 11 pages.
Okunola et al., "Is Modafinil an Atypical Dopamine Uptake Inhibitor?", Gordon Research Conference: Catecholamines, Bates College, Lewiston, ME Aug. 2011, Abstract Only (2 pages)
JP05148222A; 19930615; English Abstract Only (1 page).
JP39012646 B4; 19640704; English Abstract Only (1 page).
JP39015839 B4; 19640805; English Abstract Only (1 page).
JP39019655 B4; 19640911; English Abstract Only (1 page).
JP39026553 B4; 19641121; English Abstract Only (1 page).
JP43013468 B4; 19680607; English Abstract Only (1 page).
Jung et al., "Simple Synthesis of Modafinil Derivatives and Their Anti-Inflammatory Activity", Molecules 2012, 17, 10446-10458.
Kharul et al., "Convenient Synthesis of Structurally Novel 1,3-Distributed Azetidine Derivatives", Synthetic Communications 2008, 38(11), 1703-1717.
Mahler et al., "Modafinil attenuates reinstatement of cocaine seeking: role for cystine-glutamate exchange and metabrotropic glutamate receptors", Addiction Biology, Sep. 27, 2012, 1369-1600.
Matsushima et al., Osaka-shiritsu Daigaku Igaku Zasshi (1962), 11 379-92 English Abstract Only (1 page).
Minzenberg et al., "Modafinil: A Review of Neurochemical Actions and Effects on Cognition", Neuropsychopharmacology (2008) 33, 1477-1502.
Newman et al., "Atypical Dopamine Uptake Inhibitors that Provide Clues About Cocaine's Mechanism at the Dopamine Transporter", Top Med Chem (2009) 4: 95-129.
Patel et al., Indian Journal of Experimental Biology (1971), 9(1), 117-119.
Reichel et al., "Chronic modafinil effects on drug-seeking following methamphetamine self-administration in rats", Journal of International Neuropsychopharmacology (2012), 15, 919-929.
Reichel et al., "Modafinil effects on reinstatement of methamphetamine seeking in a rat model of relapse", Psychopharmacology (2010) 210:337-346.
Schmitt et al., "The Atypical Stimulant and Nootropic Modafinil Interacts with the Dopamine Transporter in a Different Manner than Classical Cocaine-Like Inhibitors", PLoS ONE 2011, 6(10), e25790 (13 pages)
SciFinder Search Results; 2013; 13 pages.
Scoriels et al., "Modafinil effects on cognition and emotion in schizophrenia and is neurochemical modulation in the brain", Neuropharmacology 64 (2013) 168-184.
Sonurlikar et al., "Antifilarial Activity of N1, N4-Disubstituted Piperazine Derivatives", Bull Haff Instt, vol. 5, No. 3, 1977, 90-93.
Tahsili-Fahadan et al., Modafinil: an anti-relapse medication, Neuropharmacology Reviews, 2010, 35, 343-344.
Vadodaria et al., "Synthesis and Central Nervous System Depressant Activity of New Piperazine Derivatives and Related Compounds", CNS-Active Piperazines. III, Sep. 1969, pp. 860-865.
Zou et al., Journal of Medicinal Chemistry, 2006, 49, 6391-6399.

* cited by examiner

POTENT AND SELECTIVE INHIBITORS OF MONOAMINE TRANSPORTERS; METHOD OF MAKING; AND USE THEREOF

CROSS REFERENCE TO RELATED APPLICATIONS

This application is a National Stage application of PCT/US14/021514, filed Mar. 7, 2014, which claims the benefit of U.S. Provisional Application No. 61/774,878, filed Mar. 8, 2013, both of which are incorporated by reference in their entirety herein.

STATEMENT OF GOVERNMENTAL INTEREST

The National Institutes of Health funded the subject matter of this disclosure through the National Institute on Drug Abuse—Intramural Research Program. The United States Government has certain rights in this application.

FIELD OF THE DISCLOSURE

The present disclosure is directed to bisarylmethylthioacetamide and bisarylmethylthioethylamine compounds useful as inhibitors of monoamine transporters.

BACKGROUND

The rapid reuptake of the monoaminergic neurotransmitters, dopamine (DA), serotonin (5-HT), and norepinephrine (NE) is described as the terminal step in the synaptic signaling of these neurotransmitters. The reuptake of DA, 5-HT and NE into the pre-synaptic cleft is mediated by the dopamine transporter (DAT), serotonin transporter (SERT) and norepinephrine transporter (NET), respectively. Inhibition of DA reuptake is proposed to be the underlying mechanism of abused drugs such as cocaine and methamphetamine. Modafinil (2-[(diphenylmethyl)sulfinyl]acetamide) has also been shown to inhibit DA reuptake, albeit with no evidence to its abuse liability in humans, despite preclinical data that suggests cocaine-like subjective effects [1] (and references cited therein). Based on its interesting pharmacological profile, modafinil and particularly its R-enantiomer (Armodafinil) have drawn recent attention focused on its binding mode at the DAT [1, 2]. These studies independently demonstrated that modafinil binds the DAT in a unique fashion as compared to cocaine and suggests that this may be related to its behavioral profile. There are many reports suggesting additional mechanisms underlying the pharmacological actions of modafinil and in particular its effectiveness in animal models of drug seeking [3-7]. However, direct interaction with these other targets has not been demonstrated. One potential confound is that modafinil is a non-aminergic compound with limited water solubility, which can complicate investigation due to the large concentration of drug needed for in vitro and in vivo studies. Direct or downstream interactions of modafinil with numerous targets including histaminergic, GABAergic, orexinergic, glutamatergic, adrenergic and serotonergic neurons have been reported [6, 7]. However, whether or not these targets are related to clinical efficacy remains undetermined.

Recently, a series of modafinil analogs have been synthesized and evaluated for binding at DAT, SERT, and NET [8]. Structure-activity relationship (SAR) studies suggested binding interactions at the DAT that appeared to contrast with cocaine and to be more similar to the atypical dopamine uptake inhibitor class of benztropine analogs, which also have a biphenyl structural motif [9]. However, the binding mode of the non-tropane based modafinil and its analogues appear to be unique at the DAT and may be exploited toward efficacious therapeutics without abuse liability. Thus, there remains a need in the art for compounds with improved monoamine transporter affinity(ies) with enhanced solubility properties that will allow further investigation into novel mechanisms that may lead to therapeutic benefit over currently used monoamine transport inhibitors.

SUMMARY

In an embodiment is a compound of Formula I

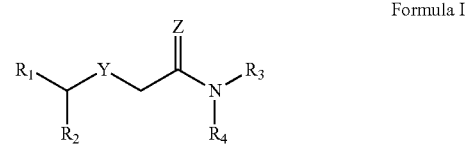

Formula I or a pharmaceutically acceptable salt thereof,
wherein
$R_1$ is $C_6$-$C_{12}$ aryl or mono- or bicyclic heteroaryl, each of which may be optionally substituted with 1, 2, or 3 substituents;

$R_2$ is $C_6$-$C_{12}$ aryl or mono- or bicyclic heteroaryl, each of which may be optionally substituted with 1, 2, or 3 substituents;

$R_3$ is hydrogen, $C_1$-$C_6$alkyl, $C_2$-$C_6$alkenyl, $C_3$-$C_7$cycloalkyl, ($C_3$-$C_7$cycloalkyl)$C_0$-$C_6$alkyl, ($C_3$-$C_7$cycloalkenyl)$C_0$-$C_6$alkyl, (heterocycloalkyl)$C_0$-$C_6$alkyl, (aryl)$C_0$-$C_6$alkyl, or (mono- or bicyclic heteroaryl)$C_0$-$C_6$alkyl;

$R_4$ is hydrogen, $C_3$-$C_6$alkyl, $C_2$-$C_6$alkenyl, $C_3$-$C_7$cycloalkyl, ($C_3$-$C_7$cycloalkyl)$C_0$-$C_6$alkyl, ($C_3$-$C_7$cycloalkenyl)$C_0$-$C_6$alkyl, (heterocycloalkyl)$C_0$-$C_6$alkyl, (aryl)$C_0$-$C_6$alkyl, or (mono- or bicyclic heteroaryl)$C_0$-$C_6$alkyl, or $R_3$ and $R_4$ together with the adjacent nitrogen atom form a heterocycloalkyl or mono- or bicyclic heteroaryl, each of which may be optionally substituted with 1, 2, or 3 substituents;

Y is O, S, S(O), or $S(O)_2$; and
Z is O, S, or 2H,
wherein the following provisos apply:
when $R_1$ and $R_2$ are both unsubstituted phenyl or phenyl substituted at the 4 position with Br, Cl, or F, Y is S, and Z is O, then both $R_3$ and $R_4$ are other than hydrogen;

when $R_1$ and $R_2$ are both unsubstituted phenyl or phenyl substituted at the 4 position with Br or Cl, Y is S, and Z is O, then $R_3$ is other than methyl or 3-phenylpropyl when $R_4$ is hydrogen, and $R_4$ is other than 3-phenylpropyl when $R_3$ is hydrogen;

when $R_1$ and $R_2$ are both unsubstituted phenyl or phenyl substituted at the 4 position with Br, Cl, or F, Y is S(O), and Z is O, then both $R_3$ and $R_4$ are other than hydrogen;

when $R_1$ and $R_2$ are both unsubstituted phenyl or phenyl substituted at the 4 position with Br or Cl, Y is S(O), and Z is O, and $R_4$ is hydrogen, then $R_3$ is other than methyl;

when $R_1$ and $R_2$ are both unsubstituted phenyl or phenyl substituted at the 4 position with Br, Y is S(O), and Z is O, then $R_3$ is other than 3-phenylpropyl when $R_4$ is hydrogen, and $R_4$ is other than 3-phenylpropyl when $R_3$ is hydrogen;

when $R_1$ and $R_2$ are both unsubstituted phenyl, Y is S or S(O), and Z is 2H, then $R_3$ is other than 3-phenylpropyl when $R_4$ is hydrogen, and $R_4$ is other than 3-phenylpropyl when $R_3$ is hydrogen;

when $R_1$ and $R_2$ are both unsubstituted phenyl, Y is S or S(O), and Z is O or 2H, then $R_3$ and $R_4$ together with the adjacent nitrogen atom do not form morpholinyl; and when $R_1$ and $R_2$ are both unsubstituted phenyl, Y is S(O), and Z is O, then $R_3$ and $R_4$ together with the adjacent nitrogen atom do not form a piperidinyl.

In an embodiment, a pharmaceutical comprises a compound of Formula I or a salt thereof and at least one pharmaceutically acceptable carrier.

In an embodiment, a method for eliciting a wake-promoting, cognition-enhancing or mood-enhancing effect comprises providing a therapeutically effective amount of a compound of Formula I or salt thereof to a patient in need of such treatment.

In an embodiment, a method for treating substance use disorders, attention deficit (hyperactivity) disorder, depressive disorders, sleep disorders or cognitive impairment comprises providing a therapeutically effective amount of a compound of Formula I or salt thereof to a patient in need of such treatment.

DETAILED DESCRIPTION

Figure 1:
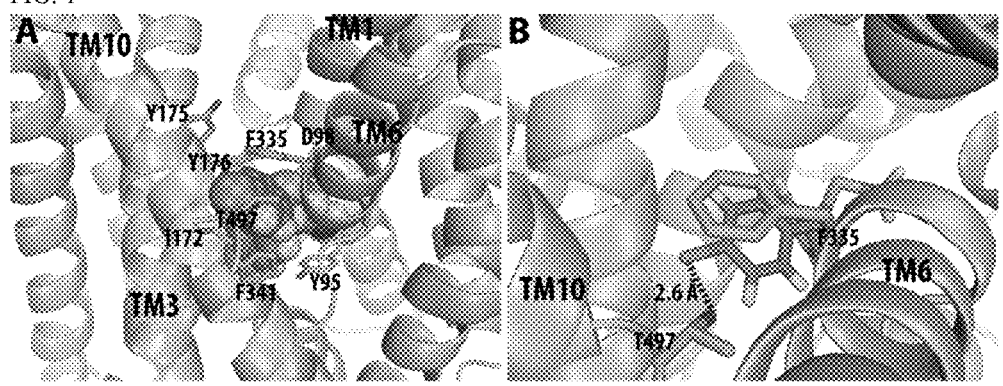
FIG. 1: Docking of compound 2h in the S1 binding sites of wild type SERT. Panel A is an overall view of the binding pose of compound 2h in the binding site. Panel B is a zoom-in view showing the interaction with Thr497 from TM10. The dashed line indicates favorable halogen bonding between 2h and the side chain OH group of T497 in WT SERT, while a similar interaction between 2h and A497, in the mutant, is absent resulting in a reduction in binding affinity.

Disclosed are bisarylmethylthioacetamide and bisarylmethylthioethylamine compounds useful as inhibitors of monoamine transporters. The compounds of Formula I disclosed herein are potent and/or selective inhibitors of dopamine (DA), serotonin (5-HT), and/or norepinephrine (NE) reuptake via their respective transporters, DAT, SERT and NET. These compounds have an advantage over modafinil in that they have higher affinity for the monoamine transporters, which may translate into lower effective doses and better bioavailability, in vivo. Several of the compounds have improved water solubility over modafinil.

Also provided are pharmaceutical compositions comprising a compound of Formula I and a pharmaceutically acceptable carrier. Such pharmaceutical compositions may contain a compound of Formula I as the only active agent or may contain a combination of a compound of Formula I and another pharmaceutically active agent. Also provided are methods for eliciting a wake-promoting, cognition-enhancing or mood-enhancing effect and for treating substance use disorders, attention deficit (hyperactivity) disorder, depressive disorders, sleep disorders or cognitive impairment to a patient in need of such treatment by administration of a compound of Formula I or a pharmaceutical composition thereof.

A compound of Formula I:

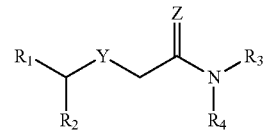

Formula I or a pharmaceutically acceptable salt thereof, wherein $R_1$ is $C_6$-$C_{12}$ aryl or mono- or bicyclic heteroaryl, each of which may be optionally substituted with 1, 2, or 3 substituents;

$R_2$ is $C_6$-$C_{12}$ aryl or mono- or bicyclic heteroaryl, each of which may be optionally substituted with 1, 2, or 3 substituents;

$R_3$ is hydrogen, $C_1$-$C_6$alkyl, $C_2$-$C_6$alkenyl, $C_3$-$C_7$cycloalkyl, ($C_3$-$C_7$cycloalkyl)$C_0$-$C_6$alkyl, ($C_3$-$C_7$cycloalkenyl)$C_0$-$C_6$alkyl, (heterocycloalkyl)$C_0$-$C_6$alkyl, (aryl)$C_0$-$C_6$alkyl, or (mono- or bicyclic heteroaryl)$C_0$-$C_6$alkyl, $R_4$ is hydrogen, $C_3$-$C_6$alkyl, $C_2$-$C_6$alkenyl, $C_3$-$C_7$cycloalkyl, ($C_3$-$C_7$cycloalkyl)$C_0$-$C_6$alkyl, ($C_3$-$C_7$cycloalkenyl)$C_0$-$C_6$alkyl, (heterocycloalkyl)$C_0$-$C_6$alkyl, (aryl)$C_0$-$C_6$alkyl, or (mono- or bicyclic heteroaryl)$C_0$-$C_6$alkyl, or $R_3$ and $R_4$ together with the adjacent nitrogen atom form a heterocycloalkyl or mono- or bicyclic heteroaryl, each of which may be optionally substituted with 1, 2, or 3 substituents;

Y is O, S, S(O), or S(O)$_2$; and

Z is O, S, or 2 hydrogens;

wherein the following provisos apply:

when $R_1$ and $R_2$ are both unsubstituted phenyl or phenyl substituted at the 4 position with Br, Cl, or F, Y is S, and Z is O, then both $R_3$ and $R_4$ are other than hydrogen;

when $R_1$ and $R_2$ are both unsubstituted phenyl or phenyl substituted at the 4 position with Br or Cl, Y is S, and Z is O, then $R_3$ is other than methyl or 3-phenylpropyl

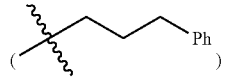

when $R_4$ is hydrogen, and $R_4$ is other than 3-phenylpropyl when $R_3$ is hydrogen;

when $R_1$ and $R_2$ are both unsubstituted phenyl or phenyl substituted at the 4 position with Br, Cl, or F, Y is S(O), and Z is O, then both $R_3$ and $R_4$ are other than hydrogen;

when $R_1$ and $R_2$ are both unsubstituted phenyl or phenyl substituted at the 4 position with Br or Cl, Y is S(O), Z is O, and $R_4$ is hydrogen, then $R_3$ is other than methyl;

when $R_1$ and $R_2$ are both unsubstituted phenyl or phenyl substituted at the 4 position with Br, Y is S(O), and Z is O, then $R_3$ is other than 3-phenylpropyl

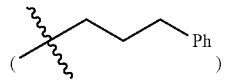

when $R_4$ is hydrogen and $R_4$ is other than 3-phenylpropyl when $R_3$ is hydrogen;

when $R_1$ and $R_2$ are both unsubstituted phenyl, Y is S or S(O), and Z is 2H, then $R_3$ is other than 3-phenylpropyl

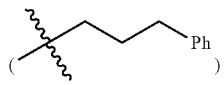

when $R_4$ is hydrogen, and $R_4$ is other than 3-phenylpropyl when $R_3$ is hydrogen;

when $R_1$ and $R_2$ are both unsubstituted phenyl, Y is S or S(O), and Z is O or 2H, then $R_3$ and $R_4$ together with the adjacent nitrogen atom do not form morpholinyl; and when $R_1$ and $R_2$ are both unsubstituted phenyl, Y is S(O), and Z is O, then $R_3$ and $R_4$ together with the adjacent nitrogen atom do not form a piperidinyl.

In an embodiment, $R_1$ and $R_2$ are each independently substituted with 1, 2, or 3 substituents such as halogen, hydroxyl, amino, nitro, cyano, $C_1$-$C_6$ alkyl, —COOH, —CHO, —CONH$_2$, $C_1$-$C_6$alkoxy, $C_2$-$C_6$alkanoyl, mono- or di-$C_1$-$C_2$alkylamino, $C_1$-$C_2$haloalkyl, $C_1$-$C_2$haloalkoxy or a combination thereof; specifically F, Cl, Br, $CH_3$, $CF_3$ or any combination thereof.

The substituent "2H" means two hydrogens, each singly bonded to the adjacent carbon atom, to result in a methylene —$CH_2$— group.

In addition to compounds of Formula I as described above, this disclosure also includes Formulae II, III, and IV, which are subgeneric compounds of Formula I, that carry any combination of the variable definitions set forth below that result in a stable compound.

Formula II

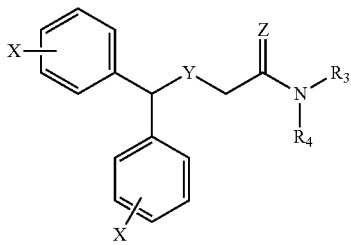

Formula III

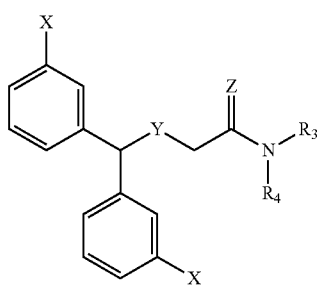

Formula IV

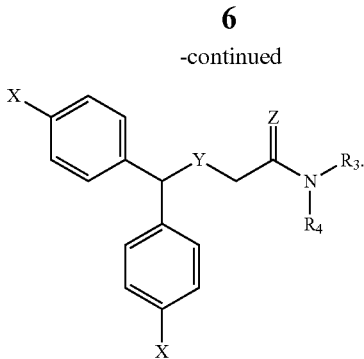

The definitions of Z, Y, $R_3$, and $R_4$ are the same as defined above for Formula I. X are independently chosen at each occurrence from hydrogen, halogen, hydroxyl, amino, nitro, cyano, $C_1$-$C_6$ alkyl, —COOH, —CHO, —CONH$_2$, $C_1$-$C_6$alkoxy, $C_2$-$C_6$alkanoyl, mono- or di-$C_1$-$C_2$alkylamino, $C_1$-$C_2$haloalkyl, and $C_1$-$C_2$haloalkoxy; specifically X are independently chosen at each occurrence from H, F, Cl, Br, $CH_3$, or $CF_3$. Unless indicated, each X independently can be located at the ortho, meta, or para positions of the ring, specifically the meta or para positions.

In addition to compounds of Formula I as described above, this disclosure also includes Formula V, which is subgeneric formula of Formula I, that carry any combination of the variable definitions set forth below that result in a stable compound.

Formula V

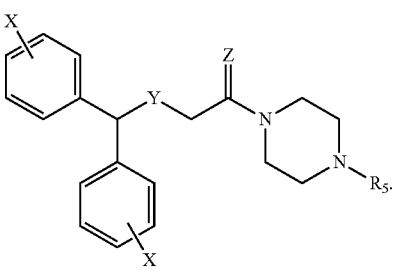

The definitions of Z and Y are the same as defined above for Formula I. X are independently chosen at each occurrence from hydrogen, halogen, hydroxyl, amino, nitro, cyano, $C_1$-$C_6$ alkyl, —COOH, —CHO, —CONH$_2$, $C_1$-$C_6$alkoxy, $C_2$-$C_6$alkanoyl, mono- or di-$C_1$-$C_2$alkylamino, $C_1$-$C_2$haloalkyl, and $C_1$-$C_2$haloalkoxy; specifically X are independently chosen at each occurrence from H, F, Cl, Br, $CH_3$, or $CF_3$. $R_5$ is hydrogen, $C_1$-$C_6$alkyl, $C_2$-$C_6$alkenyl, $C_3$-$C_7$cycloalkyl, ($C_3$-$C_7$cycloalkyl)$C_0$-$C_6$alkyl, ($C_3$-$C_7$cycloalkenyl)$C_0$-$C_6$alkyl, (hetero cycloalkyl)$C_0$-$C_6$alkyl, (aryl)$C_0$-$C_6$alkyl, or (mono- or bicyclic heteroaryl)$C_0$-$C_6$alkyl, wherein each alkyl portion independently can optionally be substituted with a hydroxyl group. Unless indicated, each X independently can be located at the ortho, meta, or para positions of the ring, specifically the meta or para positions. In an embodiment, a compound of Formula V wherein Y is S or S(O); Z is O or 2H, $R_5$ is 3-phenylpropyl, —$CH_2CH(OH)CH_3$, or —$CH_2CH(OH)CH_2Ph$; and each instance of X is located at the para position and is hydrogen, fluoro, methyl, or $CF_3$. In an embodiment, a compound of Formula V wherein Y is S or S(O); Z is O or 2H, $R_5$ is 3-phenylpropyl, —$CH_2CH(OH)$ CH$_3$, or —CH$_2$CH(OH)CH$_2$Ph; and each instance of X is located at the meta position and is hydrogen, fluoro, methyl, or CF$_3$.

Also included in this disclosure are compounds of Formula I that meets one or more of the following: R$_1$ and R$_2$ is each independently an optionally substituted C$_6$-C$_{12}$ aryl group, specifically optionally substituted phenyl; Y is S or S(O); Z is O or 2H. Also included in this disclosure are compounds of Formula I in which each of R$_1$ and R$_2$ independently is an optionally substituted C$_6$-C$_{12}$ aryl group; Y is S or S(O); Z is 2H; and R$_3$ and R$_4$ together with the adjacent nitrogen atom form an optionally substituted heterocycloalkyl. Within this embodiment, R$_3$ and R$_4$ together with the adjacent nitrogen atom form an N-substituted piperazinyl. Further within this embodiment, the N-substituted piperazinyl is substituted with C$_1$-C$_6$alkyl, C$_2$-C$_6$alkenyl, C$_3$-C$_7$cycloalkyl, (C$_3$-C$_7$cycloalkyl)C$_0$-C$_6$alkyl, (C$_3$-C$_7$cycloalkenyl)C$_0$-C$_6$alkyl, (heterocycloalkyl)C$_0$-C$_6$alkyl, (aryl)C$_0$-C$_6$alkyl, or (mono- or bicyclic heteroaryl)C$_0$-C$_6$alkyl, wherein each alkyl portion independently can optionally be substituted with a hydroxyl group.

Also included in this disclosure are compounds of Formula I, specifically Formula II, having specific formulas:

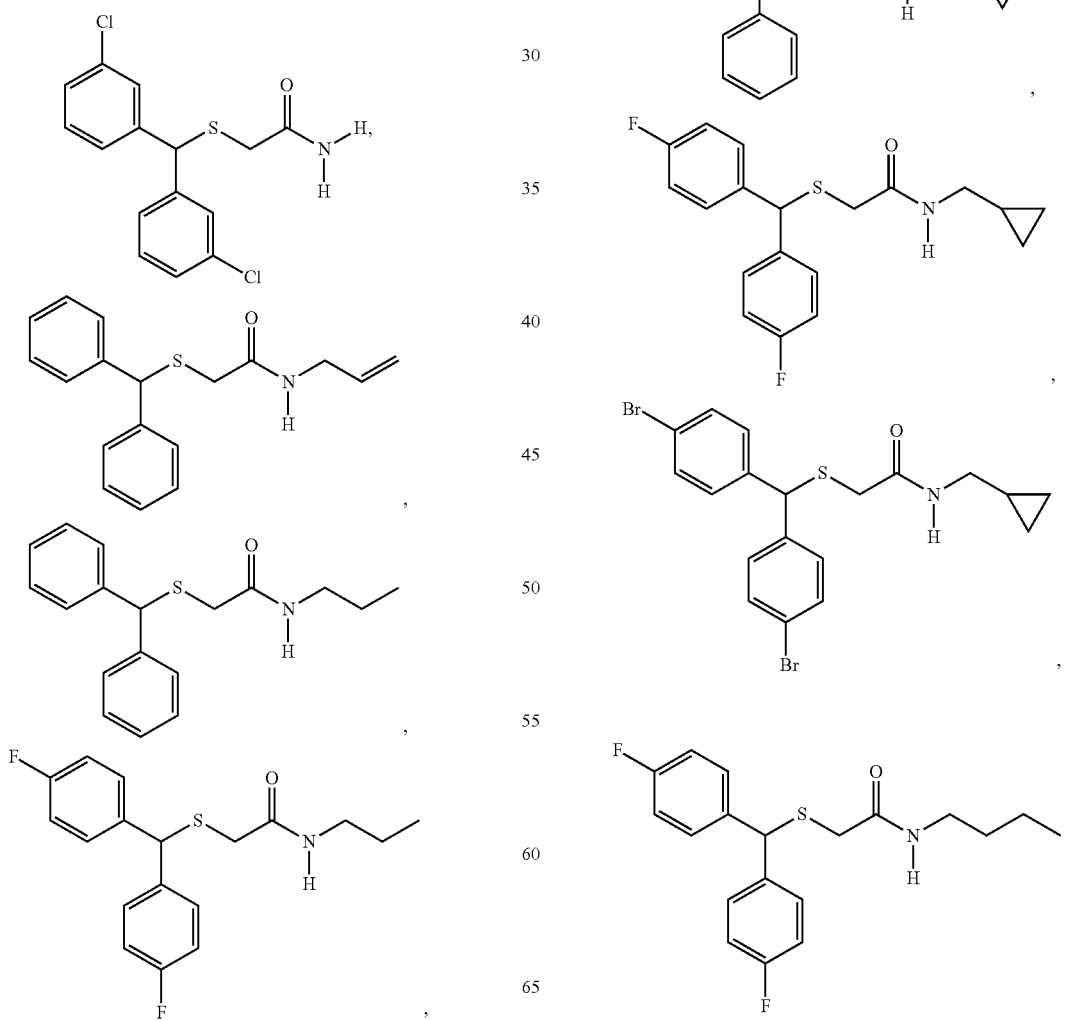
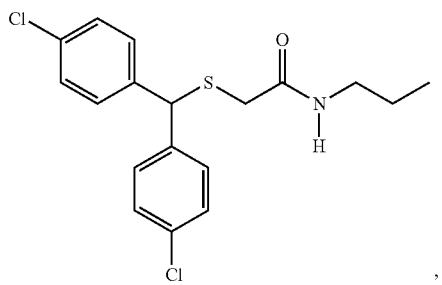
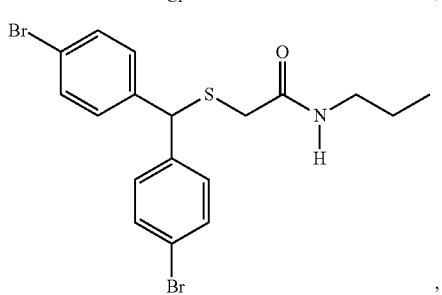
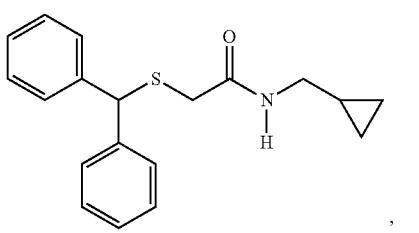
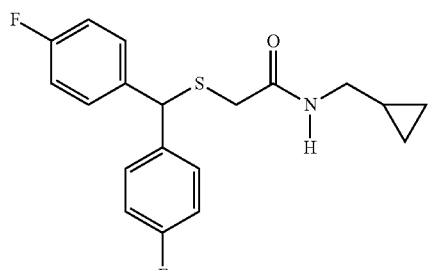
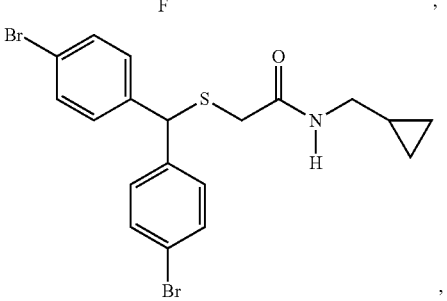
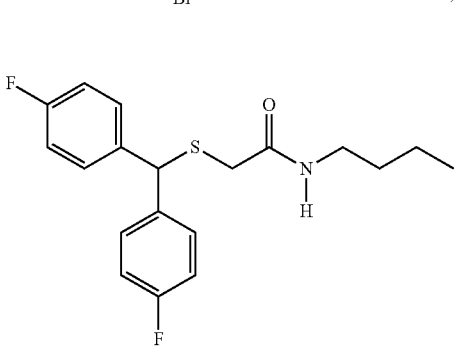

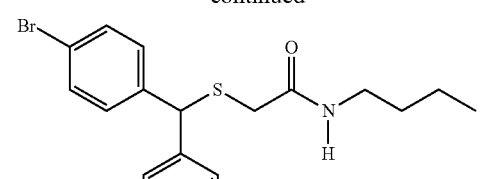
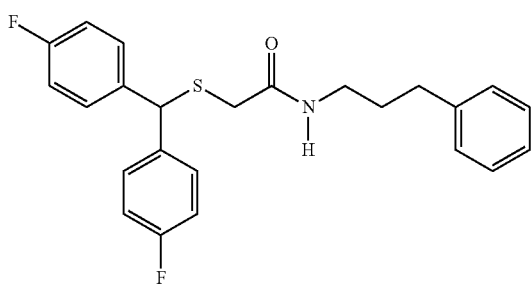
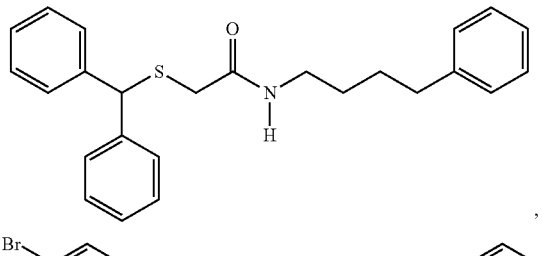
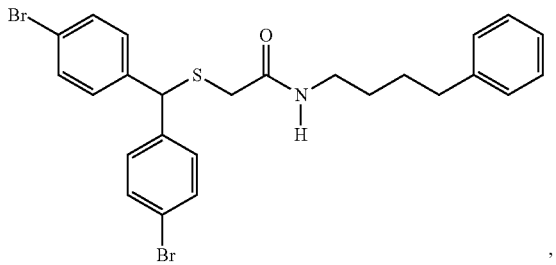
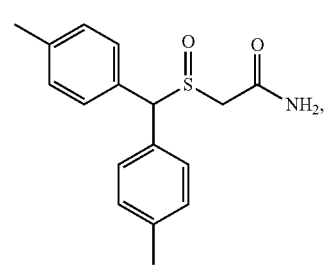
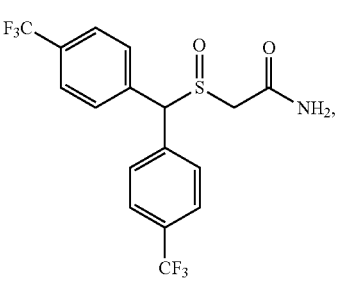
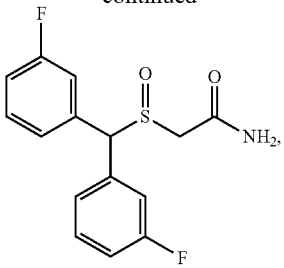
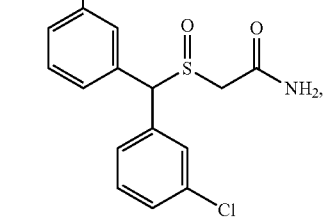
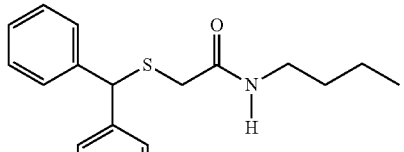
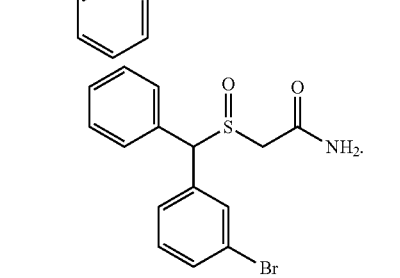
, or
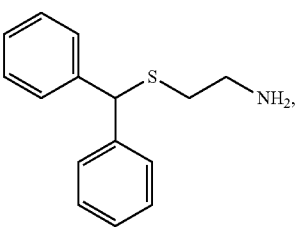
Also included in this disclosure are compounds of Formula I, wherein the following conditions are met: Y is S or S(O); Z is 2H; $R_3$ is ethyl, propyl, butyl, allyl, cyclopropylmethyl, benzyl, 2-arylethyl, 3-arylpropyl, or 4-arylbutyl; and $R_4$ is hydrogen.
Also included in this disclosure are compounds of Formula I, specifically Formula II, having specific formulas:
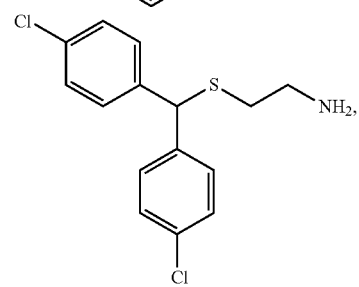

-continued

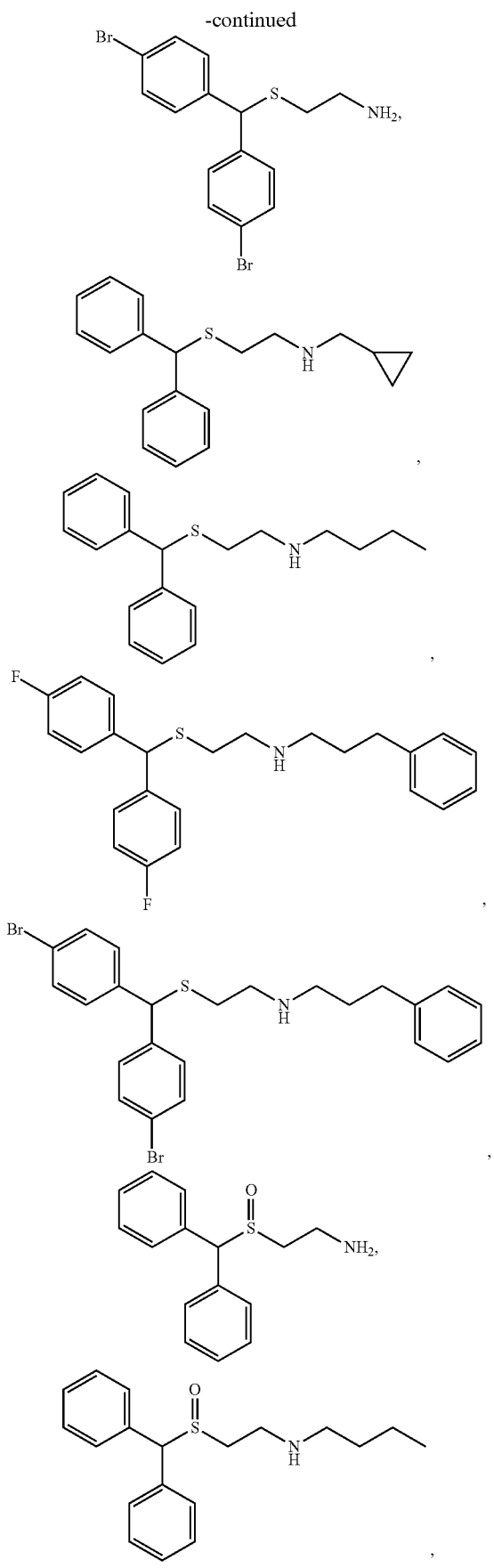

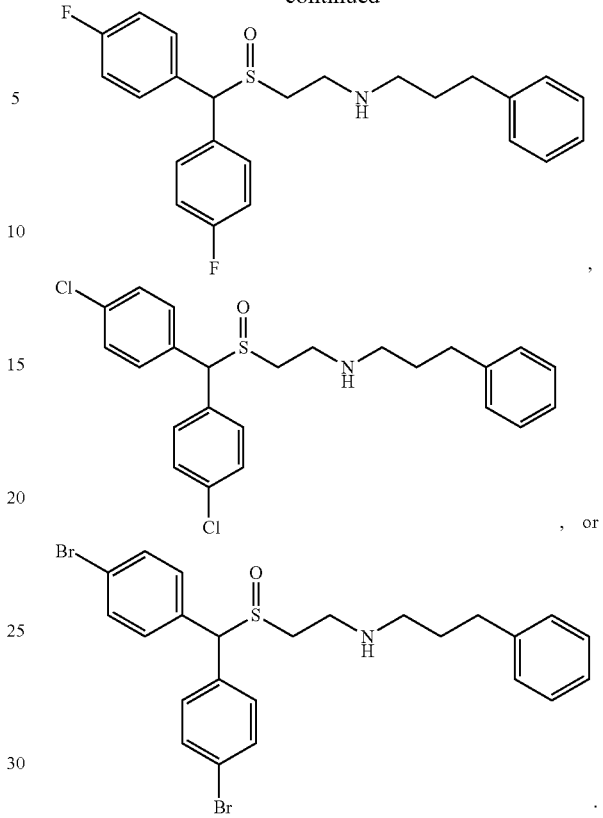

In addition to compounds of Formula I as described above, this disclosure also includes compounds of Formula I wherein a sulfoxide fragment (i.e., where Y is S(O)) has an (R)- or (S)-configuration, specifically (R).

The compounds are described using standard nomenclature. Unless defined otherwise, all technical and scientific terms used herein have the same meaning as is commonly understood by one of skill in the art to which this disclosure belongs. Unless clearly contraindicated by the context each compound name includes the free acid or free base form of the compound as well hydrates of the compound and all pharmaceutically acceptable salts of the compound.

The term "Formula I", as used herein, encompasses all compounds that satisfy Formula I, including any enantiomers, racemates and stereoisomers, as well as all pharmaceutically acceptable salts of such compounds. The phrase "a compound of Formula I" includes all subgeneric groups of Formula I including Formula II, III, IV, V, and so forth, as well as all forms of such compounds, including salts and hydrates, unless clearly contraindicated by the context in which this phrase is used.

Formula I includes all subformulae thereof. In certain situations, the compounds of Formula I may contain one or more asymmetric elements such as stereogenic centers, stereogenic axes and the like, e.g. asymmetric carbon atoms, so that the compounds can exist in different stereoisomeric forms. These compounds can be, for example, racemates or optically active forms. For compounds with two or more asymmetric elements, these compounds can additionally be mixtures of diastereomers. For compounds having asymmetric centers, it should be understood that all of the optical isomers and mixtures thereof are encompassed. In these situations, single enantiomers, i.e., optically active forms, can be obtained by asymmetric synthesis, synthesis from optically pure precursors, or by resolution of the racemates. Resolution of the racemates can also be accomplished, for example, by conventional methods such as crystallization in the presence of a resolving agent, or chromatography, using, for example, a chiral HPLC column.

Where a compound exists in various tautomeric forms, the compound is not limited to any one of the specific tautomers, but rather includes all tautomeric forms.

All isotopes of atoms occurring in the present compounds are contemplated. Isotopes include those atoms having the same atomic number but different mass numbers. By way of general example, and without limitation, isotopes of hydrogen include tritium and deuterium and isotopes of carbon include $^{11}C$, $^{13}C$, and $^{14}C$.

Certain compounds are described herein using a general formula that includes variables, e.g. $R_1$-$R_3$, X, Y, and Z. Unless otherwise specified, each variable within such a formula is defined independently of other variables. Thus, if a group is said to be substituted, e.g., with 0-2 $R_1$, then the group may be substituted with up to two $R_1$ groups and $R_1$ at each occurrence is selected independently from the definition of $R_1$. Also, combinations of substituents and/or variables are permissible only if such combinations result in stable compounds.

The term "active agent", as used herein, means a compound (including a compound of Formula I), element, or mixture that when administered to a patient, alone or in combination with another compound, element, or mixture, confers, directly or indirectly, a physiological effect on the patient. The indirect physiological effect may occur via a metabolite or other indirect mechanism. When the active agent is a compound, then salts, solvates (including hydrates) of the free compound, crystalline forms, non-crystalline forms, and any polymorphs of the compound are included. All forms are contemplated herein regardless of the methods used to obtain them.

A dash ("-") that is not between two letters or symbols is used to indicate a point of attachment for a substituent. For example, —($CH_2$)$C_3$-$C_8$cycloalkyl is attached through carbon of the methylene ($CH_2$) group.

"Alkanoyl" is an alkyl group as defined herein, covalently bound to the group it substitutes by a keto (—(C=O)—) bridge. Alkanoyl groups have the indicated number of carbon atoms, with the carbon of the keto group being included in the numbered carbon atoms. For example a $C_2$alkanoyl group is an acetyl group having the formula $CH_3(C=O)$—.

The term "alkyl", as used herein, means a branched or straight chain saturated aliphatic hydrocarbon group having the specified number of carbon atoms, generally from 1 to about 12 carbon atoms. The term $C_1$-$C_6$alkyl as used herein indicates an alkyl group having from 1, 2, 3, 4, 5, or 6 carbon atoms. Other embodiments include alkyl groups having from 1 to 8 carbon atoms, 1 to 4 carbon atoms or 1 or 2 carbon atoms, e.g. $C_1$-$C_6$alkyl, $C_1$-$C_4$alkyl, and $C_1$-$C_2$alkyl. When $C_0$-$C_n$ alkyl is used herein in conjunction with another group, for example, (cycloalkyl)$C_0$-$C_4$alkyl, the indicated group, in this case cycloalkyl, is either directly bound by a single covalent bond ($C_0$), or attached by an alkyl chain having the specified number of carbon atoms, in this case 1, 2, 3, or 4 carbon atoms. Examples of alkyl include, but are not limited to, methyl, ethyl, n-propyl, isopropyl, n-butyl, 3-methylbutyl, t-butyl, n-pentyl, and sec-pentyl.

The term "cycloalkyl", as used herein, indicates a saturated hydrocarbon ring group, having only carbon ring atoms and having the specified number of carbon atoms, usually from 3 to about 8 ring carbon atoms, or from 3 to about 7 carbon atoms. Examples of cycloalkyl groups include cyclopropyl, cyclobutyl, cyclopentyl, or cyclohexyl as well as bridged or caged saturated ring groups such as norborane or adamantane.

The term "heterocycloalkyl", as used herein, indicates a saturated cyclic group containing from 1 to about 3 heteroatoms chosen from N, O, and S, with remaining ring atoms being carbon. Heterocycloalkyl groups have from 3 to about 8 ring atoms, and more typically have from 5 to 7 ring atoms. Examples of heterocycloalkyl groups include morpholinyl, piperazinyl, piperidinyl, and pyrrolidinyl groups. A nitrogen in a heterocycloalkyl group may optionally be quaternized.

The term "alkenyl", as used herein, means straight and branched hydrocarbon chains comprising one or more unsaturated carbon-carbon bonds, which may occur in any stable point along the chain. Alkenyl groups described herein typically have from 2 to about 12 carbon atoms. Exemplary alkenyl groups are lower alkenyl groups, those alkenyl groups having from 2 to about 8 carbon atoms, e.g. $C_2$-$C_8$, $C_2$-$C_6$, and $C_2$-$C_4$ alkenyl groups. Examples of alkenyl groups include ethenyl, propenyl, and butenyl groups.

The term "cycloalkenyl", as used herein, means a saturated hydrocarbon ring group, comprising one or more unsaturated carbon-carbon bonds, which may occur in any stable point of the ring, and having the specified number of carbon atoms. Monocyclic cycloalkenyl groups typically have from 3 to about 8 carbon ring atoms or from 3 to 7 (3, 4, 5, 6, or 7) carbon ring atoms. Cycloalkenyl substituents may be pendant from a substituted nitrogen or carbon atom, or a substituted carbon atom that may have two substituents may have a cycloalkenyl group, which is attached as a spiro group. Examples of cycloalkenyl groups include cyclopropenyl, cyclobutenyl, cyclopentenyl, or cyclohexenyl as well as bridged or caged saturated ring groups such as norbornene.

The terms "(cycloalkyl)$C_0$-$C_n$alkyl", as used herein, means a substituent in which the cycloalkyl and alkyl are as defined herein, and the point of attachment of the (cycloalkyl)alkyl group to the molecule it substitutes is either a single covalent bond, ($C_0$alkyl) or on the alkyl group. (Cycloalkyl)alkyl encompasses, but is not limited to, cyclopropylmethyl, cyclobutylmethyl, and cyclohexylmethyl.

The terms "(heterocycloalkyl)$C_0$-$C_n$alkyl", as used herein, means a substituent in which the heterocycloalkyl and alkyl are as defined herein, and the point of attachment of the (heterocycloalkyl)alkyl group to the molecule it substitutes is either a single covalent bond, ($C_0$alkyl) or on the alkyl group. (Heterocycloalkyl)alkyl encompasses, but is not limited to, morpholinylmethyl, piperazinylmethyl, piperidinylmethyl, and pyrrolidinylmethyl groups.

The term "aryl", as used herein, means aromatic groups containing only carbon in the aromatic ring or rings. Typical aryl groups contain 1 to 3 separate, fused, or pendant rings and from 6 to about 18 ring atoms, without heteroatoms as ring members. When indicated, such aryl groups may be further substituted with carbon or non-carbon atoms or groups. Bicyclic aryl groups may be further substituted with carbon or non-carbon atoms or groups. Bicyclic aryl groups may contain two fused aromatic rings (naphthyl) or an aromatic ring fused to a 5- to 7-membered non-aromatic cyclic group that optionally contains 1 or 2 heteroatoms independently chosen from N, O, and S, for example, a 3,4-methylenedioxy-phenyl group. Aryl groups include, for example, phenyl, naphthyl, including 1-naphthyl and 2-naphthyl, and bi-phenyl.

The term "mono- or bicyclic heteroaryl", as used herein, indicates a stable 5- to 7-membered monocyclic or 7- to 10-membered bicyclic heterocyclic ring which contains at least 1 aromatic ring that contains from 1 to 4, or specifically from 1 to 3, heteroatoms chosen from N, O, and S, with remaining ring atoms being carbon. When the total number of S and O atoms in the heteroaryl group exceeds 1, theses heteroatoms are not adjacent to one another. Specifically, the total number of S and O atoms in the heteroaryl group is not more than 2, more specifically the total number of S and O atoms in the heteroaryl group is not more than 1. A nitrogen atom in a heteroaryl group may optionally be quaternized. When indicated, such heteroaryl groups may be further substituted with carbon or non-carbon atoms or groups. Such substitution may include fusion to a 5 to 7-membered saturated cyclic group that optionally contains 1 or 2 heteroatoms independently chosen from N, O, and S, to form, for example, a [1,3]dioxolo[4,5-c]pyridyl group. In certain embodiments 5- to 6-membered heteroaryl groups are used. Examples of heteroaryl groups include, but are not limited to, pyridyl, indolyl, pyrimidinyl, pyridizinyl, pyrazinyl, imidazolyl, oxazolyl, furanyl, thiophenyl, thiazolyl, triazolyl, tetrazolyl, isoxazolyl, quinolinyl, pyrrolyl, pyrazolyl, benz[b]thiophenyl, isoquinolinyl, quinazolinyl, quinoxalinyl, thienyl, isoindolyl, and 5,6,7,8-tetrahydroisoquinoline.

"Haloalkyl" includes both branched and straight-chain alkyl groups having the specified number of carbon atoms, substituted with 1 or more halogen atoms, up to the maximum allowable number of halogen atoms. Examples of haloalkyl include, but are not limited to, trifluoromethyl, difluoromethyl, 2-fluoroethyl, and penta-fluoroethyl.

"Haloalkoxy" is a haloalkyl group as defined herein attached through an oxygen bridge (oxygen of an alcohol radical).

"Halo" or "halogen" is any of fluoro, chloro, bromo, and iodo.

"Mono- and/or di-alkylamino" is a secondary or tertiary alkyl amino group, wherein the alkyl groups are independently chosen alkyl groups, as defined herein, having the indicated number of carbon atoms. The point of attachment of the alkylamino group is on the nitrogen. Examples of mono- and di-alkylamino groups include ethylamino, dimethylamino, and methyl-propyl-amino.

The term "substituted", as used herein, means that any one or more hydrogens on the designated atom or group is replaced with a selection from the indicated group, provided that the designated atom's normal valence is not exceeded. When the substituent is oxo (i.e., =O) then 2 hydrogens on the atom are replaced. When an oxo group substitutes aromatic moieties, the corresponding partially unsaturated ring replaces the aromatic ring. For example, a pyridyl group substituted by oxo is a pyridone. Combinations of substituents and/or variables are permissible only if such combinations result in stable compounds or useful synthetic intermediates. A stable compound or stable structure is meant to imply a compound that is sufficiently robust to survive isolation from a reaction mixture, and subsequent formulation into an effective therapeutic agent.

Unless otherwise specified substituents are named into the core structure. For example, it is to be understood that when (cycloalkyl)alkyl is listed as a possible substituent the point of attachment of this substituent to the core structure is in the alkyl portion, or when arylalkyl is listed as a possible substituent the point attachment to the core structure is the alkyl portion.

Suitable groups that may be present on a "substituted" or "optionally substituted" position include, but are not limited to, halogen; cyano; hydroxyl; nitro; azido; alkanoyl (such as a $C_2$-$C_6$ alkanoyl group such as acyl or the like); carboxamido; alkyl groups (including cycloalkyl groups) having 1 to about 8 carbon atoms, or 1 to about 6 carbon atoms; alkenyl and alkynyl groups including groups having one or more unsaturated linkages and from 2 to about 8, or 2 to about 6 carbon atoms; alkoxy groups having one or more oxygen linkages and from 1 to about 8, or from 1 to about 6 carbon atoms; aryloxy such as phenoxy; alkylthio groups including those having one or more thioether linkages and from 1 to about 8 carbon atoms, or from 1 to about 6 carbon atoms; alkylsulfinyl groups including those having one or more sulfinyl linkages and from 1 to about 8 carbon atoms, or from 1 to about 6 carbon atoms; alkylsulfonyl groups including those having one or more sulfonyl linkages and from 1 to about 8 carbon atoms, or from 1 to about 6 carbon atoms; aminoalkyl groups including groups having one or more N atoms and from 1 to about 8, or from 1 to about 6 carbon atoms; aryl having 6 or more carbons and one or more rings, (e.g., phenyl, biphenyl, naphthyl, or the like, each ring either substituted or unsubstituted aromatic); arylalkyl having 1 to 3 separate or fused rings and from 6 to about 18 ring carbon atoms, with benzyl being an exemplary arylalkyl group; arylalkoxy having 1 to 3 separate or fused rings and from 6 to about 18 ring carbon atoms, with benzyloxy being an exemplary arylalkoxy group; or a saturated, unsaturated, or aromatic heterocyclic group having 1 to 3 separate or fused rings with 3 to about 8 members per ring and one or more N, O or S atoms, e.g. coumarinyl, quinolinyl, isoquinolinyl, quinazolinyl, pyridyl, pyrazinyl, pyrimidinyl, furanyl, pyrrolyl, thienyl, thiazolyl, triazinyl, oxazolyl, isoxazolyl, imidazolyl, indolyl, benzofuranyl, benzothiazolyl, tetrahydrofuranyl, tetrahydropyranyl, piperidinyl, morpholinyl, piperazinyl, and pyrrolidinyl. Such heterocyclic groups may be further substituted, e.g. with hydroxy, alkyl, alkoxy, halogen and amino.

The term "dosage form", as used herein, means a unit of administration of an active agent. Examples of dosage forms include tablets, capsules, injections, suspensions, liquids, emulsions, creams, ointments, suppositories, inhalable forms, transdermal forms, and the like. Exemplary dosage form is a solid oral dosage form.

The term "pharmaceutical compositions", as used herein, are compositions comprising at least one active agent, such as a compound or salt of Formula I, and at least one other substance, such as a carrier. Pharmaceutical compositions meet the U.S. FDA's GMP (good manufacturing practice) standards for human or non-human drugs. The pharmaceutical compositions can be formulated into a dosage form.

The term "pharmaceutically acceptable salt", as used herein, includes derivatives of the disclosed compounds in which the parent compound is modified by making inorganic and organic, acid or base addition salts thereof. The salts of the present compounds can be synthesized from a parent compound that contains a basic or acidic moiety by conventional chemical methods. Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two. Generally, non-aqueous media like ether, ethyl acetate, ethanol, isopropanol, or acetonitrile are used, where practicable. Salts of the present compounds further include solvates of the compounds and of the compound salts.

Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts and the quaternary ammonium salts of the parent compound formed, for example, from non-toxic inorganic or organic acids. For example, conventional non-toxic acid salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, mesylic, esylic, besylic, sulfanilic, 2-acetoxybenzoic, fumaric, toluenesulfonic, methanesulfonic, ethane disulfonic, oxalic, isethionic, $HOOC-(CH_2)_n-COOH$ where n is 0-4, and the like. Lists of additional suitable salts may be found, e.g., in *Remington's Pharmaceutical Sciences,* 17th ed., Mack Publishing Company, Easton, Pa., p. 1418 (1985).

The term "carrier", as used herein, applied to pharmaceutical compositions refers to a diluent, excipient, or vehicle with which an active compound is provided.

The term "patient", as used herein, is a human or non-human animal in need of medical treatment. Medical treatment can include treatment of an existing condition, such as a disease or disorder, prophylactic or preventative treatment, or diagnostic treatment. In some embodiments the patient is a human patient.

The term "providing", as used herein, means giving, administering, selling, distributing, transferring (for profit or not), manufacturing, compounding, or dispensing.

The term "providing a compound of Formula I with at least one additional therapeutic agent", as used herein, means the compound of Formula I and the additional active agent(s) are provided simultaneously in a single dosage form, provided concomitantly in separate dosage forms, or provided in separate dosage forms for administration separated by some amount of time that is within the time in which both the compound of Formula I and the at least one additional active agent are within the blood stream of a patient. The compound of Formula I and the additional active agent need not be prescribed for a patient by the same medical care worker. The additional active agent or agents need not require a prescription. Administration of the compound of Formula I or the at least one additional active agent can occur via any appropriate route, for example, oral tablets, oral capsules, oral liquids, inhalation, injection, suppositories or topical contact.

The term "treatment", as used herein, includes providing a compound of Formula I, either as the only active agent or together with at least one additional active agent sufficient to: (a) prevent a disease or a symptom of a disease from occurring in a patient who may be predisposed to the disease but has not yet been diagnosed as having it; (b) inhibiting the disease, i.e. arresting its development; and (c) relieving the disease, i.e., causing regression of the disease. "Treating" and "treatment" also means providing a therapeutically effective amount of a compound of Formula I, as the only active agent or together with at least one additional active agent to a patient suffering from substance use disorders, attention deficit hyperactive disorder (ADHD), depressive disorders, sleep disorders or cognitive impairment or in order to elicit a wake-promoting, cognition-enhancing or mood-enhancing effect in a patient.

The term "therapeutically effective amount" of a pharmaceutical composition, as used herein, means an amount effective, when administered to a patient, to provide a therapeutic benefit such as an amelioration of symptoms, e.g., to treat a patient suffering from substance use disorders, attention deficit hyperactive disorder (ADHD), depressive disorders, sleep disorders or cognitive impairment or in order to elicit a wake-promoting, cognition-enhancing or mood-enhancing effect in a patient.

The compounds can be administered as the neat chemical, or administered as a pharmaceutical composition. Accordingly, an embodiment provides pharmaceutical compositions comprising a compound or pharmaceutically acceptable salt of Formula I, II, III, or IV, together with a pharmaceutically acceptable carrier. The pharmaceutical composition may contain a compound or salt of Formula I, II, III, IV, or V as the only active agent, or may contain one or more additional active agents.

The compounds may be administered orally, topically, parenterally, by inhalation or spray, sublingually, transdermally, via buccal administration, rectally, as an ophthalmic solution, or by other means, in dosage unit formulations containing conventional pharmaceutically acceptable carriers. The pharmaceutical composition may be formulated as any pharmaceutically useful form, e.g., as an aerosol, a cream, a gel, a pill, a capsule, a tablet, a syrup, a transdermal patch, or an ophthalmic solution. Some dosage forms, such as tablets and capsules, are subdivided into suitably sized unit doses containing appropriate quantities of the active components, e.g., an effective amount to achieve the desired purpose.

Carriers include excipients and diluents and must be of sufficiently high purity and sufficiently low toxicity to render them suitable for administration to the patient being treated. The carrier can be inert or it can possess pharmaceutical benefits of its own. The amount of carrier employed in conjunction with the compound is sufficient to provide a practical quantity of material for administration per unit dose of the compound.

Classes of carriers include, for example, buffering agents, coloring agents, diluents, disintegrants, emulsifiers, flavorants, glidants, lubricants, preservatives, stabilizers, surfactants, tableting agents, and wetting agents. Some carriers may be listed in more than one class, for example vegetable oil may be used as a lubricant in some formulations and a diluent in others. Exemplary pharmaceutically acceptable carriers include sugars, starches, celluloses, powdered tragacanth, malt, gelatin, talc, and vegetable oils. Optional active agents may be included in a pharmaceutical composition, which do not substantially interfere with the activity of the compound of Formula I.

The pharmaceutical compositions can be formulated for oral administration. These compositions contain between 0.1 and 99 weight percent ("wt. %") of a compound of Formula I, II, III, IV, or V and usually at least about 5 wt. %. Some embodiments contain from about 25 wt. % to about 50 wt. % or from about 5 wt. % to about 75 wt. % of a compound of Formula I, II, III, IV, or V.

The pharmaceutical composition can be formulated in a package comprising the pharmaceutical composition of Formula I, II, III, IV, or V in a container and further comprising instructions for using the composition in order to elicit a therapeutic effect (e.g. wake-promoting, cognition-enhancing or mood-enhancing effect) in a patient.

The pharmaceutical composition can also be formulated in a package comprising the pharmaceutical composition of Formula I, II, III, IV, or V in a container and further comprising instructions for using the composition to treat a patient suffering from, for example, substance use disorders, attention deficit (hyperactivity) disorder, depressive disorders, sleep disorders or cognitive impairment.

In an embodiment, a method of eliciting a wake-promoting, cognition-enhancing or mood-enhancing effect comprises providing an effective amount of a compound or salt of Formula I, II, III, IV, or V to a patient in need of such treatment. Alternatively, the compound may be provided in the form of a pharmaceutical composition.

In an embodiment, a method for treating substance use disorders (e.g. cocaine, methamphetamine, opioids, and the like), attention deficit hyperactive disorder, sleep disorders or cognitive impairment including cognitive impairment in psychostimulant abuse, schizophrenia and NeuroAIDS, Alzheimer's disease, depression, nicotine abuse (e.g., for smoking cessation), cancer-associated fatigue, multiple sclerosis-associated fatigue, jet-lag, post-operative grogginess, age-related memory decline, obesity, attention, bipolar disorder, anxiety, sleep disorders, or obsessive-compulsive disorders comprises providing an effective amount of a compound or salt of Formula I, II, III, IV, or V to a patient in need of such treatment. Alternatively, the compound may be provided in the form of a pharmaceutical composition.

This invention is further illustrated by the following examples that should not be construed as limiting.

EXAMPLES

Reaction conditions and yields were not optimized, and spectroscopic data and yields refer to the free base unless otherwise described for each compound. Flash chromatography was performed using silica gel (EMD Chemicals, Inc.; 230-400 mesh, 60 Å). $^1$H and $^{13}$C nuclear magnetic resonance (NMR) spectra were acquired using a Varian Mercury Plus 400 spectrometer. Chemical shifts are reported in parts-per-million (ppm) and referenced according to deuterated solvent for $^1$H spectra (CDCl$_3$, 7.26, CD$_3$OD, 3.31 or DMSO-d$_6$, 2.50), and $^{13}$C spectra (CDCl$_3$, 77.2, CD$_3$OD, 49.0 or DMSO-d$_6$, 39.5). Gas chromatography-mass spectrometry (GC/MS) data were acquired using an Agilent Technologies (Santa Clara, Calif.) 6890N GC equipped with an HP-5MS column (cross-linked 5% PH ME siloxane, 30 m×0.25 mm i.d.×0.25 micrometer film thickness) and a 5973 mass-selective ion detector in electron-impact mode. Ultrapure grade helium was used as the carrier gas at a flow rate of 1.2 ml/min. The injection port and transfer line temperatures were 250 and 280° C., respectively, and the oven temperature gradient used was as follows: the initial temperature (100° C.) was held for 3 min and then increased to 295° C. at 15° C./min over 13 min, and finally maintained at 295° C. for 10 min. Combustion analysis was performed by Atlantic Microlab, Inc. (Norcross, Ga.) and agrees within 0.5% of calculated values. Melting point determination was conducted using a Thomas-Hoover melting point apparatus and are uncorrected. On the basis of NMR, GC-MS, and combustion data, all final compounds are >95% pure.

Example 1

Synthesis of Thioacetamide and Sulfinylacetamide Analogs of Modafinil

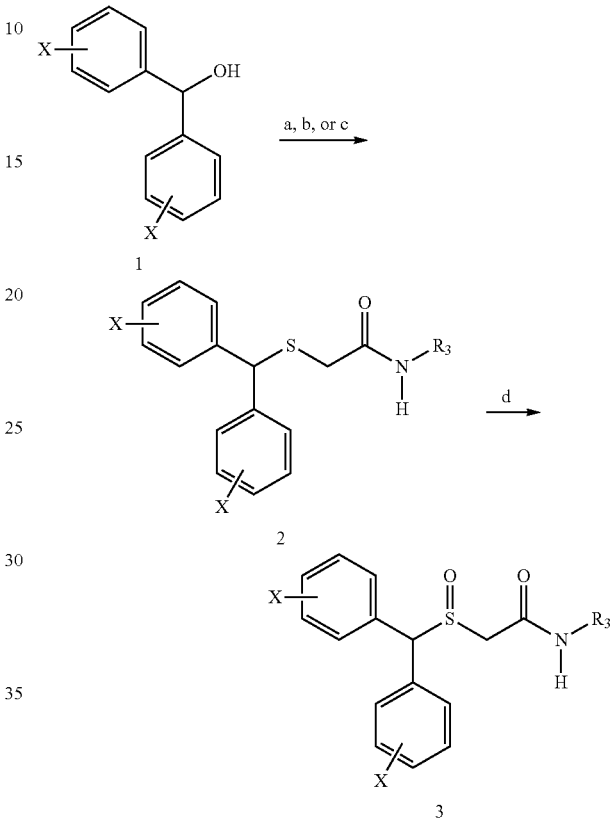

Scheme 1

Generalized reaction conditions for obtaining the thioacetamide and sulfinylacetamide compounds according to Scheme 1 are as follows: Reagents and conditions: (a) 2-Mercaptoacetamide or 2-mercapto-N-methylacetamide, trifluoroacetic acid (TFA), room temperature (60° C. for substituted-phenyl analogs), 20 h (Procedure A); (b) (i) Thioglycolic acid, TFA, room temperature (55-60° C. for substituted-phenyl analogs), overnight; (ii) CH$_3$I, K$_2$CO$_3$, acetone, reflux, overnight; (iii) NH$_4$OH, NH$_4$Cl, methanol (MeOH), 50° C., 72 hours (Procedure B); (c) (i) Thioglycolic acid, TFA, room temperature (55-60° C. for substituted-phenyl analogs), overnight; (ii) N,N'-carbonyldiimidazole (CDI), tetrahydrofuran (THF), room temperature, 2 hours; (iii) R$_3$NH$_2$, THF, 0° C. to room temperature, overnight (Procedure C); (d) H$_2$O$_2$ (30%), AcOH:MeOH (1:3), 40° C., overnight.

Bis(4-bromophenyl)methanol (1d). Starting material compound 1d was synthesized by adapting a literature method (10; Kharul et. al. Synthetic Comm. 2008, 38, 1703-1717.), from bis(4-bromophenyl)methanone (10.2 g, 30.0 mmol) and NaBH$_4$ (2.55 g, 67.4 mmol) in anhydrous ethanol (65 mL) at 0° C. under argon. The product, 1d (9.8 g, 95% yield), was recovered as a white solid. Mp 109-111° C.; $^1$H NMR (CDCl$_3$): δ 7.46 (d, J=8.6 Hz, 4H), 7.22 (d, J=8.6 Hz, 4H), 5.76 (sd, J=3.5 Hz, 1H), 2.21 (sd, J=3.5 Hz, 1H); $^{13}$C NMR (CDCl$_3$): δ 142.4, 131.9, 128.3, 121.9, 75.2.

Thioacetamides

General Thioacetamide Synthesis Procedures. Procedure A. A solution of 2-mercapto-N-methylacetamide (1 equiv.) and diphenylmethanol or the appropriate substituted diphenylmethanol (1 equiv.) in trifluoroacetic acid (TFA; 25 equiv.) was stirred at room temperature (60° C. for substituted analogs) for 20 h. The solvent was removed in vacuo and the thick oily residue was washed with water (30 mL). After decanting the water, a crude solid product was isolated by addition of diisopropyl ether (20 mL) to the oily residue and mixing vigorously. The crude solid was filtered and purified by flash column chromatography using 5% MeOH/CH$_2$Cl$_2$ to give the pure, desired product.

Procedure B. Thioacetamides 2b-2f were synthesized in three steps. Step 1: Thioglycolic acid (1 equiv.) was reacted with diphenylmethanol or the appropriate substituted diphenylmethanol (1 equiv.) in TFA (14 equiv.) overnight at room temperature. After solvent removal in vacuo, the residue obtained was washed with water (5 mL) and hexanes (15 mL) to give the carboxylic acid product, which was carried to the next step without further purification. Step 2: The acid product from step 1 was reacted with K$_2$CO$_3$ (1.5 equiv.) and iodomethane (CH$_3$I; 1.5 equiv.) in acetone (50 mL) overnight under reflux conditions. After solvent removal in vacuo, the residue was suspended in water (20 mL) and extracted with CH$_2$Cl$_2$ (3×20 mL). The combined organic layer was dried over MgSO$_4$ and concentrated to give the methyl ester, which was carried to the next step without further purification. Step 3: A mixture of the ester (1 equiv.), NH$_4$Cl (1.4 equiv.), concentrated NH$_4$OH (28.0-30.0%; 20 mL) and MeOH (5.7 mL) was stirred at 50° C. for 72 hours. MeOH was removed in vacuo and the reaction mixture was diluted with water (50 mL), extracted with ethyl acetate (3×50 mL), and dried over Na$_2$SO$_4$. The solvent was evaporated and the recovered crude product was purified by flash column chromatography using 1:1 ethyl acetate/hexanes to afford the pure product.

Procedure C. Thioacetamides 2l, 2p, 2s, 2v, and 2w were synthesized in two steps, while compounds 2j, 2k, 2m-2o, 2q, 2r, 2t, 2u, and 2x-2z were synthesized in two steps with slight modifications to the second step. Step 1: The same as step 1 for Procedure B. Step 2: CDI (1.1 equiv.) was added to a solution of the carboxylic acid product (1 equiv.) from step 1 in anhydrous THF (20 mL). The reaction mixture was stirred at room temperature for 2 hours, and then cooled to 0° C. Water (a few drops) was added to the reaction mixture (to quench excess CDI), followed by the dropwise addition of the appropriate amine (1 equiv.; dissolved in THF). The reaction mixture was left to warm to room temperature and stir overnight. The solvent was removed under vacuum to give a crude residue, which was dissolved in diethyl ether or ethyl acetate. The organic solution was washed with aqueous 1.0 M HCl solution (55 mL), water (80 mL), dilute aqueous NaHCO$_3$ solution (36 mL; 1:6 dilution of saturated NaHCO$_3$ solution), and water (2×30 mL). The organic layer was dried over MgSO$_4$, and concentrated in vacuo to give the pure product. The bromo-substituted analogs 2q, 2t, 2x, and 2z required further purification by flash column chromatography as indicated.

2-(Benzhydrylthio)acetamide (2a). Compound 2a was synthesized by stirring a solution of 2-mercaptoacetamide (0.63 g, 6.9 mmol; recovered from the 10% w/v methanol-NH$_3$ solution) and diphenylmethanol (1.3 g, 7.1 mmol) in TFA (11.9 g, 104 mmol) at room temperature for 4 h. The solvent was removed in vacuo and the brown oily residue was dissolved in CHCl$_3$ (30 mL) and washed with water (30 mL), followed by dilute NaHCO$_3$ solution (30 mL; 1:3 dilution of saturated NaHCO$_3$ solution), and water (30 mL). The organic layer was dried over MgSO$_4$ and concentrated in vacuo. The crude product was purified by flash chromatography using 1:1 ethyl acetate/hexanes to give pure 2a (0.31 g, 17% yield) as a white solid. Mp 105-106° C. (lit. 109-110° C.);[3] $^1$H NMR (CDCl$_3$): δ 7.41 (d, J=7.6 Hz, 4H), 7.33 (t, J=7.4 Hz, 4H), 7.25 (tt, J=7.2, 1.4 Hz, 2H), 6.50 (brs, 1H), 5.57 (brs, 1H), 5.17 (s, 1H), 3.09 (s, 2H); $^{13}$C NMR (CDCl$_3$): δ 171.2, 140.3, 128.9, 128.4, 127.8, 54.9, 35.7. Anal. (C$_{15}$H$_{15}$NOS) C, H, N.

2-((Di-p-tolylmethyl)thio)acetamide (2b). Compound 2b was synthesized according to general procedure B to give 2b (450 mg, 52% yield) as a yellow oil. $^1$H NMR (CDCl$_3$): δ 7.26-7.30 (m, 4H), 7.12 (d, J=7.6 Hz, 4H), 6.54 (brs, 1H), 5.53 (brs, 1H), 5.11 (s, 1H), 3.07 (s, 2H), 2.31 (s, 6H); GC/MS (EI): m/z 285 (M$^+$).

2-((Bis(4-(trifluoromethyl)phenyl)methyl)thio)acetamide (2c). Compound 2c was synthesized according to general procedure B to give 2c (680 mg, 58% yield) as a white foam. $^1$H NMR (CDCl$_3$): δ 7.61 (d, J=8.0 Hz, 4H), 7.53 (d, J=8.0 Hz, 4H), 6.29 (brs, 1H), 5.72 (brs, 1H), 5.34 (s, 1H), 3.08 (s, 2H); GC/MS (EI): m/z 393 (M$^+$).

2-((Bis(3-fluorophenyl)methyl)thio)acetamide (2d). Compound 2d was synthesized according to general procedure B to give 2d (810 mg, 61% yield) as a yellow oil. $^1$H NMR (CDCl$_3$): δ 7.27-7.33 (m, 2H), 7.17 (d, J=8.0 Hz, 2H), 7.12 (dt, J=10.0, 2.0 Hz, 2H), 6.97 (td, J=8.0, 2.4 Hz, 2H), 6.43 (brs 1H), 6.09 (brs, 1H), 5.19 (s, 1H), 3.09 (s, 2H); GC/MS (EI): m/z 293 (M$^+$).

2-((Bis(3-chlorophenyl)methyl)thio)acetamide (2e). Compound 2e was synthesized according to general procedure B to give 2e (800 mg, 65% yield) as a yellow oil. $^1$H NMR (CDCl$_3$): δ 7.38-7.39 (m, 2H), 7.25-7.28 (m, 6H), 6.42 (brs, 1H), 6.05 (brs, 1H), 5.15 (s, 1H), 3.09 (s, 2H); $^{13}$C NMR (CDCl$_3$): δ 170.9, 141.6, 134.8, 130.1, 128.3, 128.1, 126.5, 53.4, 35.4; Anal. (C$_{15}$H$_{13}$Cl$_2$NOS) C, H, N.

2-(((3-Bromophenyl)(phenyl)methyl)thio)acetamide (2f). Compound 2f was synthesized according to general procedure B to give 2f (750 mg, 58% yield) as a yellow oil. $^1$H NMR (CDCl$_3$): δ 7.57-7.58 (m, 1H), 7.31-7.39 (m, 6H), 7.25-7.29 (m, 1H), 7.18 (t, J=7.8 Hz, 1H), 6.49 (brs, 1H), 6.32 (brs, 1H), 5.16 (s, 1H), 3.07 (s, 2H); GC/MS (EI): m/z 337 (M$^+$).

2-(Benzhydrylthio)-N-methylacetamide (2g). Compound 2g was synthesized using 2-mercapto-N-methylacetamide and diphenylmethanol according to general procedure A. The product, 2g (3.5 g, 59% yield), was obtained as a white solid. Mp 101-102° C.; $^1$H NMR (DMSO-d$_6$): δ 7.86 (brs, 1H), 7.42 (d, J=8.2 Hz, 4H), 7.33 (t, J=7.6 Hz, 4H), 7.23 (t, J=7.2 Hz, 2H), 5.40 (s, 1H), 2.96 (s, 2H), 2.54 (sd, J=4.7 Hz, 3H); $^{13}$C NMR (DMSO-d$_6$): δ 169.6, 142.2, 129.5, 128.9, 128.1, 54.0, 35.8, 26.7. Anal. (C$_{16}$H$_{17}$NOS) C, H, N.

2-((Bis(4-chlorophenyl)methyl)thio)-N-methylacetamide (2h). Compound 2h was synthesized using 2-mercapto-N-methylacetamide and bis(4-chlorophenyl)methanol at 60° C. according to general procedure A. The product, 2h (2.12 g, 79% yield), was obtained as a white solid. Mp 156-158° C.; $^1$H NMR (DMSO-d$_6$): δ 7.87 (brs, 1H), 7.38-7.44 (m, 8H), 5.45 (s, 1H), 2.99 (s, 2H), 2.53 (sd, J=4.7 Hz, 3H); $^{13}$C NMR (DMSO-d$_6$): δ 169.3, 140.8, 132.8, 130.8, 129.6, 52.4, 35.8, 26.6. Anal. (C$_{16}$H$_{15}$Cl$_2$NOS) C, H, N.

2-((Bis(4-bromophenyl)methyl)thio)-N-methylacetamide (2i). Compound 2i was synthesized from 2-mercapto-N-methylacetamide and bis(4-bromophenyl)methanol at 60° C. according to general procedure A. The product, 2i (1.86 g, 74% yield), was obtained as a white solid. Mp 149-151° C.; $^1$H NMR (DMSO-d$_6$): δ 7.86 (brs, 1H), 7.53 (dt, J=8.4, 2.2 Hz, 4H), 7.35 (dt, J=8.4, 2.2 Hz, 4H), 5.42 (s, 1H), 2.99 (s, 2H), 2.53 (sd, J=4.8 Hz, 3H); $^{13}$C NMR (DMSO-d$_6$): δ 168.3, 140.2, 131.5, 130.2, 120.4, 51.6, 34.9, 25.7. Anal. (C$_{16}$H$_{15}$Br$_2$NOS) C, H, N.

N-Allyl-2-(benzhydrylthio)acetamide (2j). Compound 2j was synthesized from 2-(benzhydrylthio)acetic acid and allylamine according to the modified general procedure C. The product, 2j (1.97 g, 86% yield), was obtained as a viscous yellow oil that solidified over time. Mp 45-47° C.; $^1$H NMR (CDCl$_3$): δ 7.40 (d, J=7.2 Hz, 4H), 7.32 (t, J=7.4 Hz, 4H), 7.25 (t, J=8.0 Hz, 2H), 6.67 (brs, 1H), 5.77-5.86 (m, 1H), 5.19 (d, J$_{trans}$=17.6 Hz, 1H), 5.15 (d, J$_{cis}$=10.6 Hz, 1H), 5.13 (s, 1H), 3.84 (tt, J=5.6, 1.6 Hz), 3.14 (s, 2H); $^{13}$C NMR (CDCl$_3$): δ 168.0, 140.3, 133.8, 128.8, 128.2, 127.6, 116.8, 55.1, 42.1, 36.1. Anal. (C$_{15}$H$_{19}$NOS) C, H, N.

2-(Benzhydrylthio)-N-propylacetamide (2k). Compound 2k was synthesized from 2-(benzhydrylthio)acetic acid and propylamine according to the modified general procedure C. The product, 2k (1.05 g, 91% yield), was obtained as a yellow oil that solidified over time. Mp 57-58° C.; $^1$H NMR (CDCl$_3$): δ 7.39 (d, J=7.6 Hz, 4H), 7.32 (tt, J=7.2, 1.6 Hz, 4H), 7.24 (t, J=7.2 Hz, 2H), 6.64 (brs, 1H), 5.11 (s, 1H), 3.18 (q, J=6.8 Hz, 2H), 3.11 (s, 2H), 1.47-1.56 (m, 2H), 0.93 (t, J=7.4 Hz, 3H); $^{13}$C NMR (CDCl$_3$): δ 168.2, 140.5, 128.9, 128.4, 127.7, 55.2, 41.6, 36.3, 22.9, 11.5. Anal. (C$_{18}$H$_{21}$NOS) C, H, N.

2-((Bis(4-fluorophenyl)methyl)thio)-N-propylacetamide (2l). Compound 2l was synthesized from 2-((bis(4-fluorophenyl)methyl)thio)acetic acid and propylamine according to general procedure C. The product, 2l (320 mg, 95% yield), was obtained as a white solid. Mp 83-85° C.; $^1$H NMR (CDCl$_3$): δ 7.32-7.37 (m, 4H), 6.99-7.05 (m, 4H), 6.55 (brs, 1H), 5.14 (s, 1H), 3.20 (q, J=6.6 Hz, 2H), 3.07 (s, 2H), 1.48-1.58 (m, 2H), 0.94 (t, J=7.4 Hz, 3H); $^{13}$C NMR (CDCl$_3$): δ 168.0, 162.1 ($^1$J$_{CF}$=247 Hz), 136.0 ($^4$J$_{CF}$=3.7 Hz), 129.8 ($^3$J$_{CF}$=8.1 Hz), 115.7 ($^2$J$_{CF}$=21.4 Hz), 53.2, 41.5, 36.0, 22.8, 11.4. Anal. (C$_{18}$H$_{19}$F$_2$NOS) C, H, N.

2-((Bis(4-chlorophenyl)methyl)thio)-N-propylacetamide (2m). Compound 2m was synthesized from 2-((bis(4-chlorophenyl)methyl)thio)acetic acid and propylamine according to the modified general procedure C. The product, 2m (2.06 g, 91% yield), was obtained as a viscous yellow oil that solidified over time. Mp 57-59° C.; $^1$H NMR (CDCl$_3$): δ 7.30 (s, 8H), 6.34 (brs, 1H), 5.11 (s, 1H), 3.20 (q, J=6.8 Hz, 2H), 3.07 (s, 2H), 1.48-1.57 (m, 2H), 0.93 (t, J=7.4 Hz, 3H); $^{13}$C NMR (CDCl$_3$): δ 168.0, 138.6, 133.8, 129.7, 129.2, 53.6, 41.7, 36.1, 22.9, 11.5. Anal. (C$_{18}$H$_{19}$Cl$_2$NOS) C, H, N.

2-((Bis(4-bromophenyl)methyl)thio)-N-propylacetamide (2n). Compound 2n was synthesized from 2-((bis(4-bromophenyl)methyl)thio)acetic acid and propylamine according to the modified general procedure C. The product, 2n (1.75 g, 80% yield), was obtained as a light yellow solid. Mp 92-94° C.; $^1$H NMR (CDCl$_3$): δ 7.45 (d, J=8.8 Hz, 4H), 7.24 (d, J=8.8 Hz, 4H), 6.41 (brs, 1H), 5.08 (s, 1H), 3.19 (q, J=6.8 Hz, 2H), 3.07 (s, 2H), 1.47-1.56 (m, 2H), 0.93 (t, J=7.2 Hz, 3H); $^{13}$C NMR (CDCl$_3$): δ 168.0, 139.1, 132.1, 130.0, 121.9, 53.7, 41.7, 36.1, 22.9, 11.5. Anal. (C$_{18}$H$_{19}$Br$_2$NOS) C, H, N.

2-(Benzhydrylthio)-N-(cyclopropylmethyl)acetamide (2o). Compound 2o was synthesized from 2-(benzhydrylthio)acetic acid and cyclopropylmethylamine according to the modified general procedure C. The product, 2o (0.25 g, 94% yield), was obtained as a yellow oil. $^1$H NMR (CDCl$_3$): δ 7.41 (d, J=7.6 Hz, 4H), 7.33 (tt, J=7.4, 1.9 Hz, 4H), 7.25 (tt, J=7.4, 1.7 Hz, 2H), 6.73 (brs, 1H), 5.14 (s, 1H), 3.12 (s, 2H), 3.09 (dd, J=7.2, 5.6 Hz, 2H), 0.90-1.00 (m, 1H), 0.53 (q, J=6.4 Hz, 2H), 0.22 (q, J=5.2 Hz, 2H); $^{13}$C NMR (CDCl$_3$): δ 168.1, 140.5, 128.9, 128.4, 127.7, 55.1, 44.7, 36.3, 10.8, 3.6. Anal. (C$_{19}$H$_{21}$NOS) C, H, N.

2-((Bis(4-fluorophenyl)methyl)thio)-N-(cyclopropylmethyl)acetamide (2p). Compound 2p was synthesized from 2-((bis(4-fluorophenyl)methyl)thio)acetic acid and cyclopropylmethylamine according to general procedure C. The product, 2p (320 mg, 92% yield), was obtained as a white solid. Mp 103-105° C.; $^1$H NMR (CDCl$_3$): δ 7.35 (dd, J=8.8, 5.2 Hz, 4H), 6.99-7.05 (m, 4H), 6.58 (brs, 1H), 5.16 (s, 1H), 3.11 (dd, J=7.0, 5.4 Hz, 2H), 3.08 (s, 2H), 0.91-1.01 (m, 1H), 0.52-0.56 (m, 2H), 0.23 (q, J=5.0 Hz, 2H); $^{13}$C NMR (CDCl$_3$): δ 167.9, 162.1 ($^1$J$_{CF}$=248 Hz), 136.0 ($^4$J$_{CF}$=3.0 Hz), 129.8 ($^3$J$_{CF}$=8.1 Hz), 115.7 ($^2$J$_{CF}$=21.4 Hz), 53.3, 44.6, 36.0, 10.7, 3.4. Anal. (C$_{19}$H$_{19}$F$_2$NOS) C, H, N.

2-((Bis(4-bromophenyl)methyl)thio)-N-(cyclopropylmethyl)acetamide (2q). Compound 2q was synthesized from 2-((bis(4-bromophenyl)methyl)thio)acetic acid and cyclopropylmethylamine according to the modified general procedure C. Purification by flash column chromatography using 1:1 ethyl acetate/hexanes gave the pure product, 2q (1.08 g, 94% yield), as a white solid. Mp 84-85° C.; $^1$H NMR (CDCl$_3$): δ 7.49 (dt, J=8.8, 2.2 Hz, 4H), 7.25 (dt, J=8.4, 2.4 Hz, 4H), 6.56 (brs, 1H), 5.12 (s, 1H), 3.09 (dd, J=7.2, 5.6 Hz, 2H), 3.07 (s, 2H), 0.88-0.97 (m, 1H), 0.53 (q, J=6.6 Hz, 2H), 0.21 (q, J=5.2 Hz, 2H); $^{13}$C NMR (CDCl$_3$): δ 167.9, 139.0, 132.0, 130.0, 121.8, 53.5, 44.6, 35.9, 10.7, 3.5. Anal. (C$_{19}$H$_{19}$Br$_2$NOS ¼C$_4$H$_8$O$_2$) C, H, N.

2-(Benzhydrylthio)-N-butylacetamide (2r). Compound 2r was synthesized from 2-(benzhydrylthio)acetic acid and n-butylamine according to the modified general procedure C. The product, 2r (264 mg, 87% yield), was obtained as a yellow oil. $^1$H NMR (CDCl$_3$): δ 7.39 (d, J=7.2 Hz, 4H), 7.32 (t, J=7.4 Hz, 4H), 7.24 (tt, J=7.2, 1.7 Hz, 2H), 6.64 (brs, 1H), 5.11 (s, 1H), 3.21 (q, J=6.7 Hz, 2H), 3.10 (s, 2H), 1.43-1.51 (m, 2H), 1.30-1.39 (m, 2H), 0.93 (t, J=7.2 Hz, 3H); $^{13}$C NMR (CDCl$_3$): δ 168.2, 140.5, 128.9, 128.3, 127.7, 55.1, 39.6, 31.7, 20.2, 13.9. Anal. (C$_{19}$H$_{23}$NOS) C, H, N.

2-((Bis(4-fluorophenyl)methyl)thio)-N-butylacetamide (2s). Compound 2s was synthesized from 2-((bis(4-fluorophenyl)methyl)thio)acetic acid and n-butylamine according to general procedure C. The product, 2s (350 mg, 100%), was obtained as a white solid. Mp 63-64° C.; $^1$H NMR (CDCl$_3$): δ 7.34 (dd, J=8.8, 5.2 Hz, 4H), 6.99-7.05 (m, 4H), 6.49 (brs, 1H), 5.13 (s, 1H), 3.24 (q, J=6.6 Hz, 2H), 3.07 (s, 2H), 1.45-1.52 (m, 2H), 1.31-1.40 (m, 2H), 0.94 (t, J=7.2 Hz, 3H); $^{13}$C NMR (CDCl$_3$): δ 167.9, 162.1 ($^1$J$_{CF}$=247 Hz), 136.0 ($^4$J$_{CF}$=3.7 Hz), 129.8 ($^3$J$_{CF}$=8.1 Hz), 115.7 ($^2$J$_{CF}$=21.4 Hz, 4C), 53.3, 39.5, 36.0, 31.6, 20.1, 13.7. Anal. (C$_{19}$H$_{21}$F$_2$NOS) C, H, N.

2-((Bis(4-bromophenyl)methyl)thio)-N-butylacetamide (2t). Compound 2t was synthesized from 2-((bis(4-bromophenyl)methyl)thio)acetic acid and n-butylamine according to the modified general procedure C. Purification by flash column chromatography using 10% MeOH/CHCl$_3$ gave the pure product, 2t (0.50 g, 88% yield), as a yellow oil. $^1$H NMR (CDCl$_3$): δ 7.45 (dt, J=8.4, 2.0 Hz, 4H), 7.24 (dt, J=8.8, 2.4 Hz, 4H), 6.40 (brs, 1H), 5.07 (s, 1H), 3.22 (q, J=6.8 Hz, 2H), 3.07 (s, 2H), 1.43-1.51 (m, 2H), 1.30-1.39 (m, 2H), 0.94 (t, J=7.2 Hz, 3H); $^{13}$C NMR (CDCl$_3$): δ 167.9, 139.1, 132.1, 130.0, 121.9, 53.7, 39.7, 36.1 31.7, 20.2, 13.9. Anal. (C$_{19}$H$_{21}$Br$_2$NOS) C, H, N.

2-(Benzhydrylthio)-N-(3-phenylpropyl)acetamide (2u). Compound 2u was synthesized from 2-(benzhydrylthio)acetic acid and 3-phenyl-1-propylamine according to the modified general procedure C. Purification on a Teledyne ISCO CombiFlash® R$_f$ instrument using 1:1 ethyl acetate/hexanes gave the pure product 2u (1.66 g, 94% yield), as a white solid. Mp 63-65° C.; $^1$H NMR (CDCl$_3$): δ 7.37-7.39 (m, 4H), 7.28-7.33 (m, 6H), 7.16-7.27 (m, 5H), 6.61 (brs, 1H), 5.10 (s, 1H), 3.24 (q, J=6.8 Hz, 2H), 3.09 (s, 2H), 2.64 (t, J=7.6 Hz, 2H), 1.78-1.86 (m, 2H); $^{13}$C NMR (CDCl$_3$): δ 168.3, 141.3, 140.5, 128.9, 128.6, 128.5, 128.3, 127.7, 126.2, 55.2, 39.5, 36.3, 33.4, 31.2. Anal. (C$_{24}$H$_{25}$NOS) C, H, N.

2-((Bis(4-fluorophenyl)methyl)thio)-N-(3-phenylpropyl)acetamide (2v). Compound 2v was synthesized from 2-((bis(4-fluorophenyl)methyl)thio)acetic acid and 3-phenyl-1-propylamine according to general procedure C. The product, 2v (1.2 g, 100%), was obtained as a yellow oil. $^1$H NMR (CDCl$_3$): δ 7.26-7.35 (m, 6H), 7.16-7.22 (m, 3H), 6.98-7.04 (m, 4H), 6.48 (brs, 1H), 5.12 (s, 1H), 3.27 (q, J=6.8 Hz, 2H), 3.04 (s, 2H), 2.66 (t, J=7.8 Hz, 2H), 1.81-1.88 (m, 2H); $^{13}$C NMR (CDCl$_3$): δ 168.0, 162.1 ($^1J_{CF}$=247 Hz), 141.1, 135.9 ($^4J_{CF}$=2.9 Hz), 129.8 ($^3J_{CF}$=8.1 Hz), 128.4 ($^2J_{CF}$=21.4 Hz), 126.1, 115.8, 115.6, 53.3, 39.4, 36.0, 33.2, 31.1. Anal. (C$_{24}$H$_{23}$F$_2$NOS) C, H, N.

2-((bis(4-chlorophenyl)methyl)thio)-N-(3-phenylpropyl)acetamide (2w). Compound 2w was synthesized from 2-((bis(4-chlorophenyl)methyl)thio)acetic acid and 3-phenyl-1-propylamine according to general procedure C. The product 2w (1 g, 75%) was obtained as a yellow oil. $^1$H NMR (CDCl$_3$): δ 7.15-7.31 (m, 13H), 6.38 (brs, 1H), 5.09 (s, 1H), 3.26 (q, J=6.6 Hz, 2H), 3.04 (s, 2H), 2.65 (t, J=7.6 Hz, 2H), 1.80-1.87 (m, 2H); $^{13}$C NMR (CDCl$_3$): δ 167.9, 141.1, 138.4, 133.6, 129.5, 129.0, 128.5, 128.3, 126.1, 53.4, 39.4, 35.9, 33.2, 31.0. Anal. (C$_{24}$H$_{23}$Cl$_2$NOS) C, H, N.

2-((Bis(4-bromophenyl)methyl)thio)-N-(3-phenylpropyl)acetamide (2x). Compound 2x was synthesized from 2-((bis(4-bromophenyl)methyl)thio)acetic acid and 3-phenyl-1-propylamine according to the modified general procedure C. Purification by flash column chromatography using 7:3 ethyl acetate/hexanes and trituration in boiling diisopropyl ether gave the pure product, 2x (1.94 g, 76% yield), as a white solid. Mp 89-91° C.; $^1$H NMR (DMSO-d$_6$): δ 7.97 (t, J=5.4 Hz, 1H), 7.52 (dt, J=8.8, 2.2 Hz, 4H), 7.35 (dt, J=8.8, 2.3 Hz, 4H), 7.26 (t, J=7.6 Hz, 2H), 7.17 (d, J=7.6 Hz, 2H), 7.15-7.18 (m, 1H), 5.42 (s, 1H), 2.99-3.04 (m, 4H), 2.55 (t, J=7.8 Hz, 2H), 1.62-1.70 (m, 2H); $^{13}$C NMR (DMSO-d$_6$): δ 168.9, 142.5, 141.1, 132.5, 131.1, 129.2, 126.7, 121.4, 52.6, 52.5, 39.3, 35.9, 33.4, 31.6. Anal. (C$_{24}$H$_{23}$Br$_2$NOS) C, H, N.

2-(Benzhydrylthio)-N-(4-phenylbutyl)acetamide (2y). Compound 2y was synthesized from 2-(benzhydrylthio)acetic acid and 4-phenyl-1-butylamine according to the modified general procedure C. The product, 2y (0.73 g, 96% yield), was obtained as a yellow oil. $^1$H NMR (CDCl$_3$): δ 7.35-7.38 (m, 4H), 7.28-7.32 (m, 6H), 7.16-7.26 (m, 5H), 6.61 (brs, 1H), 5.08 (s, 1H), 3.22 (q, J=6.7 Hz, 2H), 3.10 (s, 2H), 2.64 (t, J=7.4 Hz, 2H), 1.61-1.69 (m, 2H), 1.48-1.55 (m, 2H); $^{13}$C NMR (CDCl$_3$): δ 168.2, 142.1, 140.4, 128.9, 128.52, 128.50, 128.3, 127.7, 126.0, 55.2, 39.7, 36.2, 35.6, 29.2, 28.8. Anal. (C$_{25}$H$_{27}$NOS) C, H, N.

2-((Bis(4-bromophenyl)methyl)thio)-N-(4-phenylbutyl)acetamide (2z). Compound 2z was synthesized from 2-((bis(4-bromophenyl)methyl)thio)acetic acid and 4-phenyl-1-butylamine according to the modified general procedure C. Purification by flash column chromatography using 1:1 ethyl acetate/hexanes gave the pure product, 2z (1.2 g, 90% yield), as a yellow oil. $^1$H NMR (CDCl$_3$): δ 7.43 (dt, J=8.0, 2.3 Hz, 4H), 7.28 (t, J=7.4 Hz, 2H), 7.20 (d, J=8.4 Hz, 4H), 7.15-7.19 (m, 3H), 6.39 (brs, 1H), 5.04 (s, 1H), 3.23 (q, J=6.7 Hz, 2H), 3.05 (s, 2H), 2.64 (t, J=7.6 Hz, 2H), 1.61-1.69 (m, 2H), 1.48-1.55 (m, 2H); $^{13}$C NMR (CDCl$_3$): δ 168.0, 142.0, 139.0, 132.1, 130.0, 128.54, 128.52, 126.1, 121.9, 53.6, 39.8, 36.0, 35.6, 29.2, 28.8. Anal. (C$_{25}$H$_{25}$Br$_2$NOS) C, H, N.

Sulfinylacetamides 2-((Di-p-tolylmethyl)sulfinyl)acetamide (3a). Compound 3a was synthesized by adding H$_2$O$_2$ (0.11 mL, 1.1 mmol; 1 equiv.) to a solution of compound 2b (310 mg, 1.1 mmol; 1 equiv.) in a solvent mixture of acetic acid (1.1 mL) and MeOH (3.3 mL). The reaction mixture was stirred at 40° C. overnight. The solvent was removed in vacuo, and the isolated crude residue was purified by flash column chromatography using a gradient solvent system of 1:1 ethyl acetate: CH$_2$Cl$_2$ to 5% MeOH:CH$_2$Cl$_2$. The pure product, 3a (510 mg, 72%), was obtained as a white solid. Mp 138-139° C.; $^1$H NMR (CDCl$_3$): δ 7.36 (d, J=8.2 Hz, 2H), 7.30, (d, J=8.2 Hz, 2H), 7.20 (sd, J=3.7 Hz, 4H), 7.12 (brs, 1H), 5.72 (brs, 1H), 5.12 (s, 1H), 3.46 (d, J=14.8 Hz, 1H), 3.10 (d, J=14.4 Hz, 1H), 2.34 (s, 6H); $^{13}$C NMR (CDCl$_3$): δ 166.4, 138.8, 138.5, 131.3, 131.2, 130.1, 129.6, 129.2, 128.6, 71.2, 51.2, 21.1. Anal. (C$_{17}$H$_{19}$NO$_2$S.½H$_2$O) C, H, N.

2-((Bis(4-(trifluoromethyl)phenyl)methyl)sulfinyl)acetamide (3b). Compound 3b was synthesized as described for 3a using compound 2c (680 mg, 1.73 mmol) to give the product, 3b (510 mg, 72%), as a white solid. Mp 75-77° C.; $^1$H NMR (CDCl$_3$): δ 7.70 (dd, J=8.0, 6.0 Hz, 4H), 7.60 (dd, J=8.6, 2.6 Hz, 4H), 6.70 (brs, 1H), 5.71 (brs, 1H), 5.40 (s, 1H), 3.56 (d, J=14.0 Hz, 1H), 3.12 (d, J=14.2 Hz, 1H); $^{13}$C NMR (CDCl$_3$): δ 165.3, 137.8, 137.0, 131.4 ($^2J_{CF}$=33.2 Hz), 131.2 ($^2J_{CF}$=33.2 Hz), 129.9, 129.3, 126.6 ($^3J_{CF}$=3.7 Hz), 126.0 ($^3J_{CF}$=3.7 Hz), 123.8 ($^1J_{CF}$=272 Hz), 123.6 ($^1J_{CF}$=273 Hz), 69.6, 51.8. Anal. (C$_{17}$H$_{13}$F$_6$NO$_2$S.½H$_2$O) C, H, N.

2-((Bis(3-fluorophenyl)methyl)sulfinyl)acetamide (3c). Compound 3c was synthesized as described for 3a using compound 2d (810 mg, 2.76 mmol) to give the product, 3c (600 mg, 70%), as a white solid. Mp 161-162° C.; $^1$H NMR (CDCl$_3$): δ 7.34-7.42 (m, 2H), 7.14-7.27 (m, 4H), 7.04-7.10 (m, 2H), 6.98 (brs, 1H), 6.18 (brs, 1H), 5.33 (s, 1H), 3.49 (d, J=13.6 Hz, 1H), 3.23 (d, J=14.0 Hz, 1H); $^{13}$C NMR (CDCl$_3$): δ 166.0, 163.0 ($^1J_{CF}$=248 Hz), 162.8 ($^1J_{CF}$=248 Hz), 136.5, 135.8, 131.2 ($^3J_{CF}$=8.1 Hz), 130.5 ($^3J_{CF}$=8.1 Hz), 125.3, 124.5 ($^4J_{CF}$=3.0 Hz), 116.5 ($^2J_{CF}$=22.8 Hz), 115.9 ($^2J_{CF}$=22.1 Hz), 69.7, 52.2. Anal. (C$_{15}$H$_{13}$F$_2$NO$_2$S) C, H, N.

2-((Bis(3-chlorophenyl)methyl)sulfinyl)acetamide (3d). Compound 3d was synthesized as described for 3a using compound 2e (800 mg, 2.45 mmol) to give the product, 3d (600 mg, 71%), as a white solid. Mp 115-116° C.; $^1$H NMR (CDCl$_3$): δ 7.43-7.43 (m, 2H), 7.31-7.37 (m, 6H), 7.05 (brs, 1H), 6.36 (brs, 1H), 5.36 (s, 1H), 3.47 (d, J=13.6 Hz, 1H), 3.27 (d, J=13.6 Hz, 1H); $^{13}$C NMR (CDCl$_3$): δ, 166.3, 136.3, 135.6, 135.4, 134.8, 130.8, 130.2, 129.6, 129.2, 129.0, 128.8, 127.7, 126.9, 69.4, 52.9. Anal. (C$_{15}$H$_{13}$Cl$_2$NO$_2$S) C, H, N.

2-(((3-Bromophenyl)(phenyl)methyl)sulfinyl)acetamide (3e). Compound 3e was synthesized as described for 3a using compound 2f (750 mg, 2.23 mmol) to give the product, 3e (540 mg, 69%), as a white solid. Mp 149-151° C.; $^1$H NMR (DMSO-d$_6$): δ 7.65-7.69 (m, 2H), 7.48-7.57 (m, 4H), 7.30-7.43 (m, 5H), 5.36 (s, 1H), 3.39 (d, J=13.6 Hz, 1H), 3.20 (d, J=13.6 Hz, 1H); $^{13}$C NMR (DMSO-d$_6$): δ 166.2, 137.4, 136.7, 132.2, 130.8, 130.6, 129.7, 129.1, 128.7, 128.6, 128.4, 128.1, 121.6, 67.5, 56.4. Anal. (C$_{15}$H$_{14}$BrNO$_2$S) C, H, N.

2-(Benzhydrylsulfinyl)-N-methylacetamide (3f). Compound 3f was synthesized as described for 3a using compound 2g (500 mg, 1.84 mmol) to give the product, 3f (427 mg, 81%), as a yellow oil. $^1$H NMR (CDCl$_3$): δ 7.35-7.49

(m, 10H), 7.02 (brs, 1H), 5.18 (s, 1H), 3.44 (d, J=14.0 Hz, 1H), 3.13 (d, J=14.0 Hz, 1H), 2.82 (sd, J=4.7 Hz, 3H); $^{13}$C NMR (CDCl3): δ 164.9, 134.9, 134.2, 129.7, 129.6, 129.13, 129.08, 129.01, 128.9, 71.7, 52.3, 26.7. Anal. ($C_{16}H_{17}NO_2S·¾H_2O$) C, H, N.

2-(Bis(4-bromophenyl)methylsulfinyl)-N-(3-phenylpropyl)acetamide (3g). Compound 3g was synthesized as described for 3a using compound 2x (220 mg, 0.41 mmol) to give the product, 3g (100 mg, 44%), as a colorless oil. $^1$H NMR (CDCl$_3$): δ 7.51-7.55 (m, 4H), 7.16-7.31 (m, 9H), 6.69 (t, J=5.4 Hz, 1H), 5.13 (s, 1H), 3.42 (d, J=14.0 Hz, 1H), 3.33 (q, J=7.0 Hz, 2H), 3.05 (d, J=14.0 Hz, 1H), 2.67 (t, J=7.8 Hz, 2H), 1.85-1.89 (m, 2H); $^{13}$C NMR (CDCl3): δ 163.7, 141.3, 133.4, 132.9, 132.5, 132.3, 131.3, 130.7, 128.7, 128.6, 126.3, 123.53, 123.47, 69.7, 52.4, 39.7, 33.4, 31.2. Anal. ($C_{24}H_{23}Br_2NO_2S·½H_2O$) C, H, N.

Example 2

Synthesis of Thioethanamine and Sulfinylethanamine Analogs of Modafinil

Generalized reaction conditions for obtaining the thioethanamine and sulfinylethanamine compounds according to Scheme 2 are as follows: (a) cysteamine hydrochloride, BF$_3$.OEt$_2$, glacial AcOH, 80-90° C., ~20 min (40-50 min for substituted analogs (Procedure D)); (b) (i) Procedure D; (ii) cyclopropane carboxaldehyde, NaBH$_3$CN, MeOH, 1,2-dichloroethane, room temperature, overnight; (c) (i) Procedure D; (ii) BuBr, CsOH.H$_2$O, 4 Å molecular sieve (MS), dimethyl formamide (DMF), room temperature (rt), 20 h; (d) LiAlH$_4$, H$_2$SO$_4$, THF; (e) BH$_3$.THF, THF, reflux, overnight; (f) NaIO$_4$, H$_2$O, EtOH, 0° C. to room temperature, overnight; (g) H$_2$O$_2$ (30%), AcOH:MeOH (1:3), 40° C., 24 h.

Thioethanamines

General Thioethanamine Synthesis Procedure. Procedure D. Compounds 4a-4c were synthesized as follows. A solution of cysteamine hydrochloride (1 equiv.), diphenylmethanol or the appropriate halogen-substituted diphenylmethanol (1 equiv.), and BF$_3$.OEt$_2$ (1.1 equiv.) in glacial acetic acid (3 mL/mmol) was stirred at 90-95° C. for 20 min (40-50 min for substituted analogs). The reaction mixture was cooled to room temperature and diethyl ether (20 mL/mmol) was added to precipitate a solid (the hydrochloride salt) from the mixture. The solid was filtered and dried under vacuum for 3 days in the presence of NaOH pellets. The dried solid was dissolved in hot ethanol, filtered and the solvent removed in vacuo. Finally, the solid was triturated in hot (boiling) ethyl acetate to give the pure product as the hydrochloride salt.

2-(benzhydrylthio)ethan-1-amine (4a). Compound 4a was synthesized from diphenylmethanol according to general

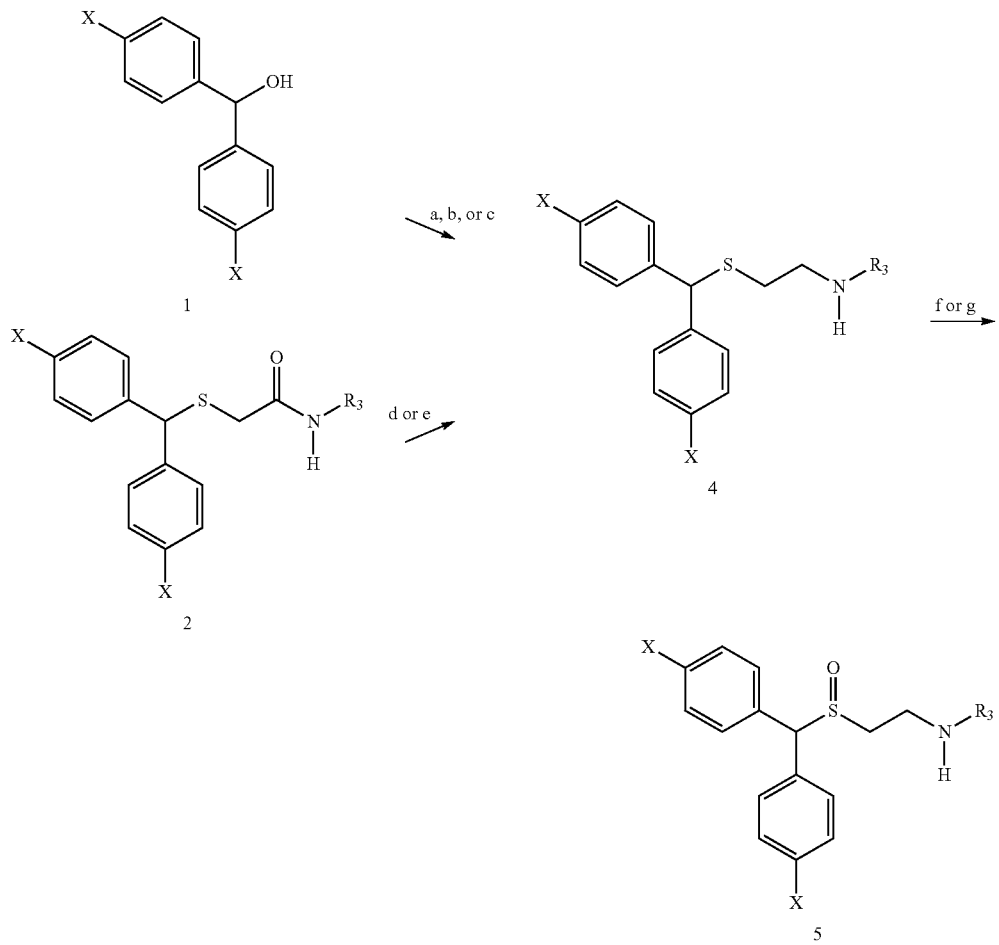

Scheme 2 procedure D to give the hydrochloride salt in quantitative yield. The hydrochloride salt of 4a (10.1 g, 36.1 mmol) was converted to the free base by dissolving in saturated aqueous $NaHCO_3$ solution (120 mL) and extracted into $CHCl_3$ (150 mL). The layers were separated and the organic layer was washed with distilled water (80 mL) and aqueous brine solution (100 mL), and dried over $MgSO_4$. The solvent was evaporated in vacuo to give the free base, 4a (7.90 g, 90% yield), as a yellow oil. Some of the isolated free base was converted into the oxalate salt. Mp 177-179° C.; $^1$H NMR ($CDCl_3$): δ 7.43 (d, J=8.0 Hz, 4H), 7.31 (t, J=7.4 Hz, 4H), 7.22 (tt, J=7.4, 1.5 Hz, 2H), 5.16 (s, 1H), 2.81 (t, J=6.2 Hz, 2H), 2.51 (t, J=6.4 Hz, 2H); $^{13}$C NMR ($CDCl_3$): δ 141.5, 128.7, 128.4, 127.4, 54.0, 41.0, 36.7. Anal. ($C_{15}H_{17}NS.\frac{3}{4}C_2H_2O_4$) C, H, N.

2-((bis(4-chlorophenyl)methyl)thio)ethan-1-amine (4b). Compound 4b was synthesized from bis(4-chlorophenyl)methanol according to general procedure D with a reaction time of 50 min. The hydrochloride salt product, 4b (1.06 g, 62% yield), was obtained as an off-white solid. Mp 179-181° C.; $^1$H NMR (HCl salt; DMSO-$d_6$): δ 8.12 (brs, 3H), 7.48 (d, J=8.4 Hz, 4H), 7.42 (d, J=8.8 Hz, 4H), 5.56 (s, 1H), 2.94 (t, J=7.6 Hz, 2H), 2.60 (t, J=7.2 Hz, 2H); $^{13}$C NMR (HCl salt; DMSO-$d_6$): δ 139.9, 132.0, 129.9, 128.7, 50.2, 38.0, 28.6. Anal. ($C_{15}H_{15}Cl_2NS.\frac{3}{4}HCl.\frac{3}{4}H_2O$) C, H, N.

2-((bis(4-bromophenyl)methyl)thio)ethan-1-amine (4c). Compound 4c was synthesized from bis(4-bromophenyl)methanol according to general procedure D with a reaction time of 40 min. The hydrochloride salt product, 4c (4.15 g, 72% yield), was obtained as an off-white solid. Mp 192-194° C.; $^1$H NMR (HCl salt: DMSO-$d_6$): δ 8.09 (brs, 3H), 7.55 (dt, J=8.4, 2.3 Hz, 4H), 7.41 (dt, J=8.8, 2.2 Hz, 4H), 5.53 (s, 1H), 2.94 (t, J=7.4 Hz, 2H), 2.59 (t, J=7.4 Hz, 2H); $^{13}$C NMR (HCl salt; DMSO-$d_6$): δ 140.2, 131.6, 130.2, 120.5, 50.2, 37.9, 28.5. Anal. ($C_{15}H_{15}Br_2NS.HCl$) C, H, N.

2-(benzhydrylthio)-N-(cyclopropylmethyl)ethan-1-amine (4d). Compound 4d was synthesized according to general procedure D starting with compound 4a. A suspension of the hydrochloride salt of 4a (1.0 g, 3.6 mmol) and cyclopropane carboxaldehyde (0.28 g, 4.0 mmol) in 1,2-dichloroethane (62 mL) was stirred at room temperature under argon atmosphere for 1.3 h. Sodium cyanoborohydride (0.69 g, 1 mmol) dissolved in methanol (2.0 mL) was added to the reaction mixture, and the mixture was stirred at room temperature under an argon atmosphere overnight. After 19 h of reaction time, saturated $NaHCO_3$ solution (30 mL), distilled water (30 mL) and $CH_2Cl_2$ (15 mL) were added to the reaction mixture and stirred vigorously for 1 hour. The layers were separated and the aqueous layer was washed with $CH_2Cl_2$ (3×25 mL). The combined $CH_2Cl_2$ extract was washed with water (50 mL), dried over $MgSO_4$ and concentrated in vacuo to give a crude product. The isolated crude was purified by flash column chromatography using an ethyl acetate/hexanes solvent gradient (from 4:1 to 1:4) to give the free base, 4d (0.50 g, 47% yield), as a yellow oil. Some of the isolated free base was converted into the hydrochloride salt in $CHCl_3$ using a 1.0 M HCl in ether solution. Mp 122-124° C.; $^1$H NMR ($CDCl_3$): δ 7.42 (d, J=7.4 Hz, 4H), 7.30 (t, J=7.4 Hz, 4H), 7.22 (tt, J=7.2, 1.6 Hz, 2H), 5.17 (s, 1H), 2.76 (t, J=6.4 Hz, 2H), 2.59 (t, J=6.6 Hz, 2H), 2.40 (d, J=6.8 Hz, 2H), 0.81-0.97 (m, 1H), 0.44-0.48 (m, 2H), 0.09 (qd, J=4.8, 1.2 Hz, 2H); $^{13}$C NMR ($CDCl_3$): δ 141.6, 128.7, 128.4, 127.3, 54.7, 54.3, 48.1, 32.9, 11.4, 3.5. Anal. ($C_{19}H_{23}NS.HCl.\frac{1}{4}H_2O$) C, H, N.

N-(2-(benzhydrylthio)ethyl)butan-1-amine (4e). Compound 4e was synthesized using compound 4a (general procedure D). A mixture of $CsOH.H_2O$ (0.29 g, 1.7 mmol) and activated 4 Å molecular sieves (0.52 g) in anhydrous DMF (8.3 mL; freshly distilled and stored over activated 4 Å molecular sieves) was purged of air under vacuum and flushed with argon gas. After stirring the mixture for 13 min, the free base of compound 4a (0.41 g, 1.7 mmol), dissolved in anhydrous DMF (4.0 mL), was added. The reaction mixture was stirred under vacuum for 25 min, flushed with argon for 5 min, and n-butyl bromide (0.28 g, 2.04 mmol) was added. This was followed by another 10 min of vacuum purging, and the reaction left to stir overnight at room temperature. The reaction mixture was filtered after 20 h of reaction time and the undissolved solids washed with ethyl acetate. The filtrate was evaporated in vacuo to give a liquid residue, which was taken up in aqueous 1M NaOH (30 mL) and extracted with ethyl acetate (2×25 mL). The organic extract was washed with brine (50 mL), dried over a 1:1 $Na_2SO_4/MgSO_4$ mixture, and concentrated in vacuo. The crude product was purified by flash column chromatography using 5% diethyl ether/hexanes (with 0.5% $NEt_3$) to give the free base, 4e (0.22 g, 44% yield), as a yellow oil. Some of the isolated free base was converted into the oxalate salt. Mp 209-211° C.; $^1$H NMR ($CDCl_3$): δ 7.42 (d, J=7.2 Hz, 4H), 7.30 (t, J=7.6 Hz, 4H), 7.22 (tt, J=7.2, 1.6 Hz, 2H), 5.17 (s, 1H), 2.74 (t, J=6.4 Hz, 2H), 2.58 (t, J=6.2 Hz, 2H), 2.53 (t, J=7.2 Hz, 2H), 1.40-1.47 (m, 2H), 1.27-1.37 (m, 2H), 0.90 (t, J=7.6 Hz, 3H); $^{13}$C NMR ($CDCl_3$): δ 141.6, 128.7, 128.4, 127.3, 54.2, 49.3, 48.3, 32.8, 32.3, 20.6, 14.1. Anal ($C_{19}H_{25}NS.C_2H_2O_4$) C, H, N.

N-(2-(benzhydrylthio)ethyl)-3-phenylpropan-1-amine (4f). Compound 4f was synthesized from compound 2u. Briefly, sulfuric acid (98%; 305 mg, 3.11 mmol) in THF (8.0 mL) was added dropwise at 0° C. to $LiAlH_4$ (227 mg, 5.99 mmol) in THF (13 mL) and the mixture was stirred for 15 minutes at room temperature. Compound 2u (563 mg, 1.50 mmol) in THF (11 mL) was added dropwise to the reduction mixture at room temperature and stirred overnight. The reaction mixture was cooled to 0° C. and quenched with water (5.0 mL) and 10% NaOH (20 mL) successively. The mixture was filtered, the insolubles washed with THF, and the filtrate evaporated to dryness. The crude product was purified on a Teledyne ISCO CombiFlash® $R_f$ instrument using 97:3:0.03 $CHCl_3$/MeOH/$NH_4OH$ to give the pure product, 4f (312 mg, 58%), as a yellow oil. The free base was converted to the oxalate salt. Mp 196-198° C.; $^1$H NMR ($CDCl_3$): δ 7.42 (d, J=7.6 Hz, 4H), 7.27-7.32 (m, 6H), 7.16-7.23 (m, 5H), 5.16 (s, 1H), 2.73 (t, J=6.4 Hz, 2H), 2.63 (t, J=7.8 Hz, 2H), 2.54-2.58 (m, 4H), 1.74-1.82 (m, 2H); $^{13}$C NMR ($CDCl_3$): δ 142.2, 141.6, 128.7, 128.53, 128.47, 128.4, 127.4, 125.9, 54.2, 49.1, 48.3, 33.7, 32.8, 31.8. Anal ($C_{24}H_{27}NS.C_2H_2O_4$) C, H, N.

N-(2-((bis(4-fluorophenyl)methyl)thio)ethyl)-3-phenylpropan-1-amine (4g). Compound 4g was synthesized as described for compound 4f using compound 2v, except that the reaction mixture was stirred at room temperature for 2 hours (instead of overnight) before quenching with water and NaOH (15% instead of 10%/). The crude product was purified by flash column chromatography (95:5:0.5 $CHCl_3$/MeOH/$NH_4OH$) to give the pure product, 4g (820 mg, 86.6%), as a yellow oil. The free base was converted to the oxalate salt, which was recrystallized from a methanol/acetone mixture. Mp 198-200° C.; $^1$H NMR ($CDCl_3$): δ 7.33-7.37 (m, 4H), 7.16-7.30 (m, 5H), 6.97-7.02 (m, 4H), 5.13 (s, 1H), 2.72 (t, J=6.4 Hz, 2H), 2.64 (t, J=7.8 Hz, 2H), 2.52 (m, 4H), 1.75-1.82 (m, 2H); $^{13}$C NMR ($CDCl_3$): δ 161.9 ($^1J_{CF}$=246 Hz), 142.0, 137.0 ($^4J_{CF}$=3.0 Hz), 129.7 ($^3J_{CF}$=8.1 Hz), 128.4, 125.8, 115.5 ($^2J_{CF}$=21.4 Hz, 4C), 52.5, 48.8, 48.0, 33.6, 32.6, 31.6. Anal. ($C_{24}H_{25}F_2NS \cdot C_2H_2O_4$) C, H, N.

N-(2-((bis(4-chlorophenyl)methyl)thio)ethyl)-3-phenylpropan-1-amine (4h). Compound 4h was synthesized as described for 4g using compound 2w (1 g, 2.2 mmol). The crude product, 4h (850 mg), was obtained as a yellow oil and carried to the next step without further purification.

N-(2-((bis(4-bromophenyl)methyl)thio)ethyl)-3-phenylpropan-1-amine (4i). Compound 4i was synthesized by reducing compound 2x with a borane-THF reagent. A solution of 1 M $BH_3$.THF complex (14 mL, 14.0 mmol) was added slowly (in two aliquots) to a solution of compound 2x (1.50 g, 2.81 mmol) in freshly distilled THF (15 mL) at 2° C. The reaction mixture was refluxed for 16 h, cooled to 0° C., quenched with $CH_3OH$ (30 mL), saturated with aqueous HCl (5.0 mL of conc. HCl (37%)), and refluxed for another 23 h, successively. The solvent was removed in vacuo to give a yellow, oily residue which was taken up in $CHCl_3$ (50 mL) and washed with distilled water (2×50 mL). The combined aqueous extract was back-washed with $CHCl_3$ (3×30 mL), then discarded. The combined $CHCl_3$ extract was washed with water (100 mL) and brine (100 mL), and concentrated in vacuo to give the hydrochloride salt of 4i. The salt was suspended in a small amount of water and the suspension made basic to a pH of 13 with 10 M NaOH (20 mL). The basic solution was continuously extracted with $CHCl_3$ for 6 h, and the layers separated. Solvent was removed from the organic layer to give the crude free base of compound 4i, which was purified by flash column chromatography (5% $MeOH/CH_2Cl_2$). The pure product, 4i (0.58 g, 40% yield), was obtained as a yellow oil and converted to the oxalate salt. Mp 187-189° C.; $^1H$ NMR ($CDCl_3$): δ 7.43 (dt, J=8.4, 2.3 Hz, 4H), 7.23-7.30 (m, 6H), 7.16-7.20 (m, 3H), 5.07 (s, 1H), 2.74 (t, J=6.6 Hz, 2H), 2.64 (t, J=7.6 Hz, 2H), 2.53-2.29 (m, 4H), 1.77-1.83 (m, 2H); $^{13}C$ NMR ($CDCl_3$): δ 142.1, 140.1, 131.9, 131.6, 130.0, 128.5, 126.0, 121.5, 53.0, 49.0, 48.3, 33.7, 32.7, 31.7. Anal. ($C_{24}H_{25}Br_2NS \cdot C_2H_2O_4$) C, H, N.

Sulfinylethanamines 2-(Benzhydrylsulfinyl)ethan-1-amine (5a). Compound 5a: a solution of sodium periodate ($NaIO_4$; 2.25 g, 10.5 mmol) in water (50 mL) was added in a dropwise manner, to a solution of the hydrochloride salt of compound 4a (2.80 g, 10.0 mmol) in ethanol (150 mL) at 0° C. The reaction was allowed to stir and warm up to room temperature for ~20 h under an argon atmosphere. The reaction mixture, which contained a white precipitate was cooled in an ice-bath and filtered. The filtrate was concentrated in vacuo to give a dark yellow, oily residue. The oily residue (the hydrochloride salt) was dissolved in $CHCl_3$, washed with an aqueous $NaHCO_3$ solution (2:3 dilution in water of saturated $NaHCO_3$ solution), distilled water, aqueous brine, and dried over $Na_2SO_4$ successively. After filtration, solvent was removed in vacuo to give the crude, free base of compound 5a. The crude product was purified by flash column chromatography using a $MeOH/CHCl_3$ (with 0.1% $NH_4OH$) gradient (from 0-1% MeOH) to give pure 5a (1.12 g, 43% yield) as a yellow oil. Some of the isolated free base was converted to the oxalate salt. Mp 161-163° C.; $^1H$ NMR ($CDCl_3$): δ 7.50 (d, J=7.8 Hz, 2H), 7.31-7.44 (m, 8H), 4.90 (s, 1H), 3.10-3.23 (m, 2H), 2.53-2.65 (m, 2H); $^{13}C$ NMR ($CDCl_3$): δ 135.8, 135.2, 129.4, 128.9, 128.7, 128.5, 128.4, 73.1, 54.4, 36.5. Anal. ($C_{15}H_{17}NOS \cdot C_2H_2O_4$) C, H, N.

N-(2-(benzhydrylsulfinyl)ethyl)butan-1-amine (5b). Compound 5b was synthesized as described for 5a from compound 4e (0.070 g, 0.23 mmol) and $NaIO_4$ (0.053 g, 0.25 mmol) in an ethanol/water ($EtOH/H_2O$) mixture (4.0/1.2 mL v/v). The pure free base product, 5b (0.020 g, 41% yield), was obtained as a yellow oil after purification of the crude by flash column chromatography using a $MeOH/CHCl_3$ (with 0.1% $NH_4OH$) gradient (from 0-2% MeOH). The isolated free base was converted to the oxalate salt. Mp 162-164° C.; $^1H$ NMR ($CDCl_3$): δ 7.49 (d, J=7.6 Hz, 2H), 7.30-7.44 (m, 8H), 4.92 (s, 1H), 2.99-3.13 (m, 2H), 2.65 (t, J=5.8 Hz, 2H), 2.56 (t, J=7.0 Hz, 2H), 1.40-1.47 (m, 2H), 1.27-1.36 (m, 2H), 0.89 (t, J=7.4 Hz, 3H); $^{13}C$ NMR ($CDCl_3$): δ 135.9, 135.2, 129.44, 129.42, 128.9, 128.8, 128.49, 128.44, 73.0, 51.1, 49.6, 43.6, 32.1, 20.5, 14.1. Anal. ($C_{19}H_{25}NOS \cdot C_2H_2O_4 \cdot 2H_2O$) C, H, N.

N-(2-((bis(4-fluorophenyl)methyl)sulfinyl)ethyl)-3-phenylpropan-1-amine (5c). Compound 5c was synthesized as described for compound 3a using 4g (900 mg, 2.27 mmol). The free base product, 5c (820 mg, 87.5% yield), was obtained as a yellow oil and converted into the oxalate salt, which was recrystallized from a methanol-acetone mixture. Mp 180-181° C. (dec.); $^1H$ NMR ($CDCl_3$): δ 7.37-7.44 (m, 4H), 7.05-7.29 (m, 9H), 5.00 (s, 1H), 3.16-3.22 (m, 1H), 3.04-3.11 (m, 1H), 2.60-2.83 (m, 6H), 1.80-1.88 (m, 2H); $^{13}C$ NMR ($CDCl_3$): δ162.8 ($^1J_{CF}$=248 Hz), 162.6 ($^1J_{CF}$=249 Hz), 141.1, 131.0 ($^3J_{CF}$=8.1 Hz), 130.3 ($^3J_{CF}$=8.1 Hz), 130.1 ($^4J_{CF}$=3.7 Hz), 128.4, 128.3, 126.0, 116.4 ($^2J_{CF}$=21.4 Hz), 115.8 ($^2J_{CF}$=21.4 Hz), 70.6, 48.7, 48.4, 43.1, 33.1, 30.1. Anal ($C_{24}H_{25}F_2NOS \cdot C_2H_2O_4$) C, H, N.

N-(2-((bis(4-chlorophenyl)methyl)sulfinyl)ethyl)-3-phenylpropan-1-amine (5d). Compound 5d was synthesized as described for compound 3a using 4h (850 mg, 1.97 mmol). The free base product, 5d (640 mg, two steps yield 72.6%), was obtained as a yellow oil and converted into the oxalate salt, which was recrystallized from hot MeOH. Mp 153-155° C.; $^1H$ NMR ($CDCl_3$): δ 7.15-7.39 (m, 13H), 4.88 (s, 1H), 2.99-3.08 (m, 2H), 2.57-2.65 (m, 6H), 1.75-1.82 (m, 2H); $^{13}C$ NMR (CDCl3): δ 141.9, 134.7, 134.6, 134.0, 132.9, 130.6, 129.9, 129.6, 129.0, 128.4, 125.9, 70.6, 51.2, 49.1, 43.1, 33.5, 31.4. Anal. ($C_{24}H_{25}Cl_2NOS \cdot C_2H_2O_4 \cdot \frac{1}{2}H_2O$) C, H, N.

N-(2-((bis(4-bromophenyl)methyl)sulfinyl)ethyl)-3-phenylpropan-1-amine (5e). Compound 5e was synthesized as described for compound 3a using 4i (230 mg, 0.443 mmol). The free base product, 5e (130 mg, 55% yield), was obtained as a yellow oil, and converted into the oxalate salt, which was recrystallized from hot MeOH. Mp 161-162° C. (dec.); $^1H$ NMR ($CDCl_3$): δ 7.45-7.53 (m, 4H), 7.15-7.32 (m, 7H), 4.83 (s, 1H), 2.99-3.08 (m, 2H), 2.57-2.65 (m, 6H), 1.75-1.82 (m, 2H); $^{13}C$ NMR (CDCl3): δ 141.9, 134.5, 133.3, 132.5, 132.3, 132.0, 131.4, 130.9, 130.2, 128.4, 125.9, 122.9, 122.7, 70.7, 51.2, 49.1, 43.1, 33.5, 31.4. Anal. ($C_{24}H_{25}Br_2NOS \cdot C_2H_2O_4$) C, H, N.

Example 3

Binding Affinity Data at Monoamine Transporters

Binding affinities of all compounds were evaluated at the DAT, SERT, and NET in rat brain membranes using previously described methods:

Dopamine Transporter Binding Assay. Brains from male Sprague-Dawley rats weighing 200-225 g (Taconic Labs) were removed, striatum dissected and quickly frozen. Membranes were prepared by homogenizing tissues in 20 volumes (w/v) of ice cold modified sucrose phosphate buffer (0.32 M sucrose, 7.74 mM $Na_2HPO_4$, 2.26 mM $NaH_2PO_4$, pH adjusted to 7.4) using a Brinkman Polytron (setting 6 for 20 sec) and centrifuged at 20,000×g for 10 min at 4° C. The resulting pellet was resuspended in buffer, recentrifuged and resuspended in buffer to a concentration of 10 mg/ml. Ligand binding experiments were conducted in assay tubes containing 0.5 ml sucrose phosphate buffer for 120 min on ice. Each tube contained 0.5 nM $^3$H WIN 35428 (specific activity 84 Ci/mmol) and 1.0 mg striatal tissue (original wet weight). Nonspecific binding was determined using 0.1 mM cocaine HCl. Incubations were terminated by rapid filtration through Whatman GF/B filters, presoaked in 0.05% PEI (polyethyleneimine), using a Brandel R48 filtering manifold (Brandel Instruments Gaithersburg, Md.). The filters were washed twice with 5 ml cold buffer and transferred to scintillation vials. Beckman Ready Safe (3.0 ml) was added and the vials were counted the next day using a Beckman 6000 liquid scintillation counter (Beckman Coulter Instruments, Fullerton, Calif.). Data were analyzed by using GraphPad Prism software (San Diego, Calif.).

Serotonin Transporter Binding Assay. Brains from male Sprague-Dawley rats weighing 200-225 g (Taconic Labs, Germantown, N.Y.) were removed, midbrain dissected and rapidly frozen. Membranes were prepared by homogenizing tissues in 20 volumes (w/v) of 50 mM Tris containing 120 mM NaCl and 5 mM KCl, (pH 7.4 at 25° C.), using a Brinkman Polytron and centrifuged at 50,000×g for 10 min at 4° C. The resulting pellet was resuspended in buffer, recentrifuged and resuspended in buffer to a concentration of 15 mg/mL. Ligand binding experiments were conducted in assay tubes containing 0.5 mL buffer for 60 min at room temperature. Each tube contained 1.4 nM [$^3$H]Citalopram (Amersham Biosciences, Piscataway, N.J.) and 1.5 mg midbrain tissue (original wet weight). Nonspecific binding was determined using 10 mM fluoxetine. Incubations were terminated by rapid filtration through Whatman GF/B filters, presoaked in 0.3% polyethylenimine, using a Brandel R48 filtering manifold (Brandel Instruments Gaithersburg, Md.). The filters were washed twice with 3 mL cold buffer and transferred to scintillation vials. Beckman Ready Value (3.0 mL) was added and the vials were counted the next day using a Beckman 6000 liquid scintillation counter (Beckman Coulter Instruments, Fullerton, Calif.). Each compound was tested with concentrations ranging from 0.01 nM to 100 mM for competition against binding of [$^3$H]Citalopram, in at least three independent experiments, each performed in triplicate. Data were analyzed with GraphPad Prism software (San Diego, Calif.).

Norepinephrine Transporter Binding Assay. Brains from male Sprague-Dawley rats weighing 200-225 g (Taconic Labs, Germantown, N.Y.) were removed, frontal cortex dissected and rapidly frozen. Membranes were prepared by homogenizing tissues in 20 volumes (w/v) of 50 mM Tris containing 120 mM NaCl and 5 mM KCl, (pH 7.4 at 25° C.), using a Brinkman Polytron and centrifuged at 50,000×g for 10 min at 4° C. The resulting pellet was resuspended in buffer, recentrifuged and resuspended in buffer to a concentration of 80 mg/mL. Ligand binding experiments were conducted in assay tubes containing 0.5 mL buffer for 60 min at 0-4° C. Each tube contained 0.5 nM [$^3$H]Nisoxetine (PerkinElmer Life Sciences, Boston, Mass.) and 8 mg frontal cortex tissue (original wet weight). Nonspecific binding was determined using 1 mM desipramine. Incubations were terminated by rapid filtration through Whatman GF/B filters, presoaked in 0.05% polyethylenimine, using a Brandel R48 filtering manifold (Brandel Instruments Gaithersburg, Md.). The filters were washed twice with 3 mL cold buffer and transferred to scintillation vials. Beckman Ready Value (3.0 mL) was added and the vials were counted using a Beckman 6000 liquid scintillation counter (Beckman Coulter Instruments, Fullerton, Calif.). Each compound was tested with concentrations ranging from 0.01 nM to 100 mM for competition against binding of [$^3$H]Nisoxetine, in at least three independent experiments, each performed in triplicate. Data were analyzed by using GraphPad Prism software (San Diego, Calif.) [11; Zou et. al. J. Med. Chem. 2006, 49, 6391-6399]. The results of the in vitro assays, grouped by functionality into the amides and amines are presented in Tables 1 and 2, respectively. All compounds were tested as racemic mixtures.

Table 1 shows the binding data for the thioacetamide and sulfinylacetamide compounds and comparative compound (±)-modafinil. Similar to (±)-modafinil ($K_i$=2520 nM), most of the compounds displayed micromolar affinities at the DAT. When there are no substituents on the diphenyl rings, substitution of the terminal amide nitrogen decreases binding affinity at the DAT with or without the S=O motif (e.g., compounds 2a, 2g, 2j, 2k, 2o, 2r, and 3f). The slight exception to this trend is observed with compounds 2u and 2y which displayed similar or nominally improved binding affinities ($K_i$=2020 and 1160 (two-fold increase) nM respectively) in comparison to (±)-modafinil. Within each series of N-substituted thioacetamides, binding affinity generally increased with halogen substitution at the para-position of the diphenylmethyl moiety in the order: H<F<Cl<Br. This order applies to both the thioacetamides and sulfinylacetamides with or without substitution on the amide nitrogen. Additionally, substitution at other positions of the diphenyl rings follows this halogen-substitution order, for example, compounds 3c-3e with halogen substituents in the meta-positions of the diphenyl rings. In general, the acetamides were selective for the DAT over the SERT and NET, except for compounds 2a and 3g, both of which display roughly equal affinities at the DAT and SERT (DAT:SERT ratio=1 and 1.4 respectively). Four compounds—2e, 2w, 2x, and 2z—were identified as the most DAT-selective compounds (SERT/DAT≥2668, 440, 249, and 241 respectively; NET/DAT≥123, 440, and 149 respectively; no displacement at the NET for 2z) among the amides. The pronounced selectivity observed with compound 2e for DAT over SERT (SERT/DAT=2668) is remarkable, especially in comparison to its regioisomer, compound 100, which is only modestly selective for DAT over SERT (SERT/DAT=5.7).

TABLE 1

BINDING AFFINITY DATA AT MONOAMINE TRANSPORTERS
FOR THIOACETAMIDE AND SULFINYLACETAMIDE
ANALOGS OF MODAFINIL IN RAT BRAIN MEMBRANES[a]

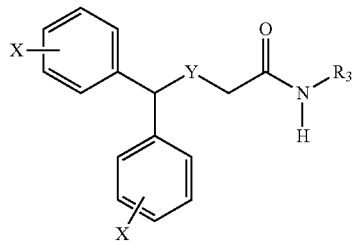

(±)-Modafinil and compounds 2a-2z, 3a-3g, and 100

| Compound | X | Y | $R_3$ | $K_i$ (nM) ± S.E.M. DAT | SERT | NET |
|---|---|---|---|---|---|---|
| (±)-modafinil[b] | H | S=O | H | 2,520 ± 204 | ND[c] | ND[c] |
| 2a | H | S | H | 12,700 ± 1,700 | 12,700 ± 1,820 | >100,000 |
| 2e | 3,3'-diCl | S | H | 277 ± 18.3 | 739,000 ± 99,800 | 34,000 ± 3,730 |
| 2g | H | S | methyl | 19,400 ± 1,410 | >300,000 | 27,300 ± 1,540 |
| 2h | 4,4'-diCl | S | methyl | 4,240 ± 557 | >30,000 | 9,810 ± 626 |
| 2i | 4,4'-diBr | S | methyl | 3,030 ± 243 | 5,750 ± 417 | 11,200 ± 1,600 |
| 2j | H | S | allyl | 9,190 ± 1,820 | >300,000 | >230,000 |
| 2k | H | S | n-propyl | 20,700 ± 420 | >550,000 | 55,900 ± 9,120 |
| 2l | 4,4'-diF | S | n-propyl | 12,000 ± 1,430 | 45,100 ± 6,330 | 61,700 ± 8,230 |
| 2m | 4,4'-diCl | S | n-propyl | 1,250 ± 133 | 10,300 ± 1,350 | 7,620 ± 788 |
| 2n | 4,4'-diBr | S | n-propyl | 592 ± 42.6 | 8,970 ± 756 | 10,600 ± 629 |
| 2o | H | S | cyclopropylmethyl | 13,900 ± 1,800 | 20,900 ± 2,960 | >100,000 |
| 2p | 4,4'-diF | S | cyclopropylmethyl | 6,860 ± 1,030 | 35,400 ± 5,680 | 57,600 ± 5,830 |
| 2q | 4,4'-diBr | S | cyclopropylmethyl | 993 ± 139 | 7,270 ± 1,080 | >100,000 |
| 2r | H | S | n-butyl | 24,000 ± 3,140 | >100,000 | >100,000 |
| 2s | 4,4'-diF | S | n-butyl | 6,470 ± 647 | 25,800 ± 2,360 | 56,200 ± 2,250 |
| 2t | 4,4'-diBr | S | n-butyl | 729 ± 69.3 | 7,090 ± 105 | 7,600 ± 383 |
| 2u | H | S | 3-phenylpropyl | 2,020 ± 29.8 | ND[c] | ND[c] |
| 2v | 4,4'-diF | S | 3-phenylpropyl | 452 ± 65.8 | 3,640 ± 517 | >100,000 |
| 2w | 4,4'-diCl | S | 3-phenylpropyl | 228 ± 32.2 | >100,000 | >100,000 |
| 2x | 4,4'-diBr | S | 3-phenylpropyl | 244 ± 36.4 | 60,800 ± 2,490 | 36,300 ± 4,510 |
| 2y | H | S | 4-phenylbutyl | 1,160 ± 145 | >100,000 | 7,980 ± 373 |
| 2z | 4,4'-diBr | S | 4-phenylbutyl | 414 ± 59.5 | >100,000 | ND |
| 3a | 4,4'-diCH$_3$ | S=O | H | 12,700 ± 347 | ND[c] | ND[c] |
| 3b | 4,4'-diCF$_3$ | S=O | H | 35,400 ± 1,280 | NT[d] | NT[d] |
| 3c | 3,3'-diF | S=O | H | 6,180 ± 816 | ND[c] | ND[c] |
| 3d | 3,3'-diCl | S=O | H | 908 ± 126 | ND[c] | ND[c] |
| 3e | H, 3-Br | S=O | H | 550 ± 7.40 | ND[c] | ND[c] |
| 3f | H | S=O | methyl | 13,400 ± 798 | >100,000 | >100,000 |
| 3g | 4,4'-diBr | S=O | 3-phenylpropyl | 1,290 ± 117 | 906 ± 113 | ND[c] |
| 100[b] | 4,4'-diCl | S | H | 2,230 ± 166 | 12,700 ± 520 | 52,100 ± 5,510 |

[a] Each $K_i$ value represents data from at least three independent experiments, each performed in triplicate. $K_i$ values were analyzed by PRISM.
[b] Comparative compound.
[c] ND, no displacement up to a concentration of 100 μM.
[d] NT, not tested.

As shown in Table 2, removal of the amide carbonyl (C=O) function resulted in improved affinities at the DAT, SERT and NET (compare compounds 4a and 5a to (±)-modafinil), with several compounds having nanomolar binding affinities at the DAT in comparison to comparative compound (±)-modafinil's micromolar affinity. With the thioethanamines, DAT affinity generally increased with increasingly bulky substitution on the terminal amine nitrogen for analogs with no diphenyl ring substituent (see compounds 4d, 4e and 4f). For analogs with halogen-substituents on the diphenyl rings within a particular series, DAT binding affinities generally increased in a reverse order to that observed for the acetamides, i.e., Br<Cl<F<H with or without the S=O group. Overall, compounds 4g ($K_i$=116 nM) and 4a ($K_i$=143 nM) displayed the highest affinities at the DAT, with each displaying about 20-fold improved affinity compared to (±)-modafinil. However, in terms of selectivity ratios among the monoamine transporters, the most DAT-selective compounds in this series are 4d, 4e and 5b (SERT/DAT=23, 18, and 41 respectively; NET/DAT=40, 36, and 89 respectively). Four compounds of this series that are SERT-selective, 4b, 4c, 4i, and 5e with compounds 4b and 4c displaying low nanomolar affinities ($K_i$=30 and 26 nM respectively) at the SERT.

TABLE 2

BINDING AFFINITY DATA AT MONOAMINE TRANSPORTERS FOR THIOETHANAMINE AND SULFINYLETHANAMINE ANALOGS OF MODAFINIL IN RAT BRAIN MEMBRANES[a]

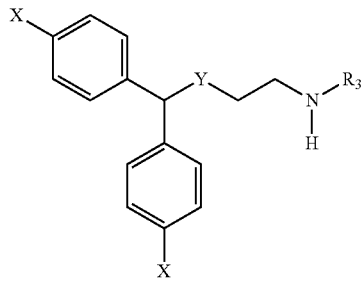

| Compounds 4a-4i, 5a-5e, and 200 | | | $K_i$ (nM) ± S.E.M. | | |
|---|---|---|---|---|---|
| Compound | X | Y | R₃ | DAT | SERT | NET |
| 4a | H | S | H | 143 ± 12.0 | 226 ± 30.6 | 982 ± 43.3 |
| 4b | Cl | S | H | 298 ± 24.6 | 29.9 ± 1.65 | 6,970 ± 595 |
| 4c | Br | S | H | 488 ± 52.2 | 26.3 ± 2.28 | 8,580 ± 595 |
| 4d | H | S | cyclopropylmethyl | 437 ± 30.1 | 10,000 ± 447 | 17,500 ± 1,940 |
| 4e | H | S | n-butyl | 315 ± 39.9 | 5,820 ± 662 | 11,500 ± 759 |
| 4f | H | S | 3-phenylpropyl | 297 ± 28.2 | 853 ± 127 | 3,910 ± 474 |
| 4g | F | S | 3-phenylpropyl | 116 ± 16.3 | 360 ± 48.3 | 3,848 ± 21.7 |
| 4i | Br | S | 3-phenylpropyl | 618 ± 53.0 | 163 ± 7.49 | 3,180 ± 228 |
| 5a | H | S=O | H | 1,110 ± 86.4 | 3,420 ± 407 | 24,600 ± 1,640 |
| 5b | H | S=O | n-butyl | 1,580 ± 79.2 | 64,600 ± 8,200 | >140,000 |
| 5c | F | S=O | 3-phenylpropyl | 200 ± 38.7 | 1,310 ± 177 | 3,280 ± 148 |
| 5d | Cl | S=O | 3-phenylpropyl | 660 ± 76.9 | 542 ± 42.6 | 5,800 ± 724 |
| 5e | Br | S=O | 3-phenylpropyl | 1,290 ± 146 | 564 ± 65.3 | 7,580 ± 615 |
| 200[b] | H | S=O | 3-phenylpropyl | 194 ± 16.8 | 1,000 ± 120 | 2,350 ± 267 |

[a]Each $K_i$ value represents data from at least three independent experiments, each performed in triplicate. $K_i$ values were analyzed by PRISM.
[b]Comparative compound.

Reduction of the amide to a secondary or primary amine significantly improves water solubility and binding affinities at all three monoamine transporters (e.g. 2a v. 4a). The effect appears to be most profound at DAT, as all but a few analogs in Table 2 have submicromolar affinities for DAT. When the diphenyl ring system is substituted with either para-Cl or Br groups, the binding affinities at SERT are more improved than at DAT in all cases and most dramatically with, compounds 4b and 4c that bind with $K_i$ values<30 nM at SERT, suggesting a secondary interaction that may differ between these two transporters.

Example 4

Synthesis of Piperazinyl Derivatives

Scheme 3

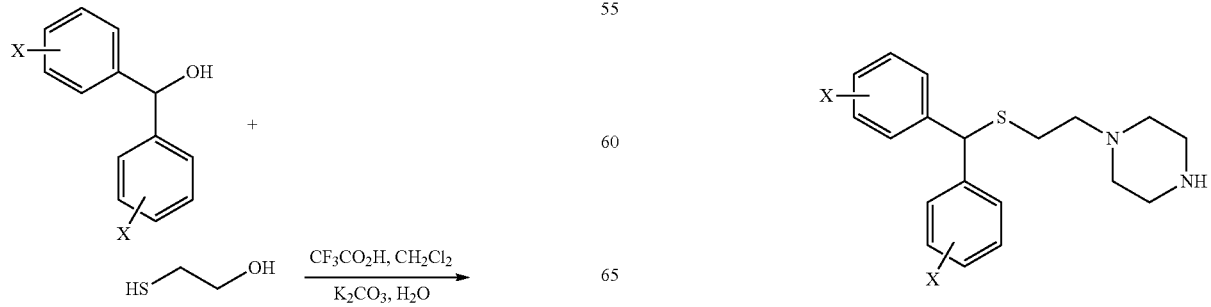

Scheme 4

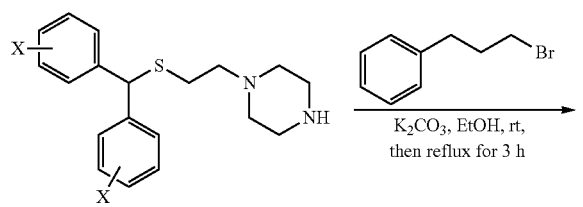

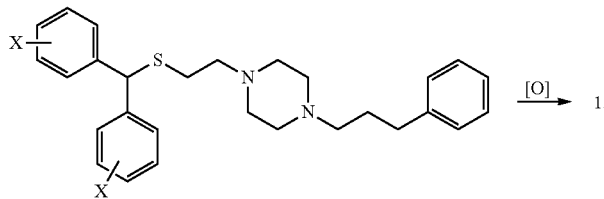

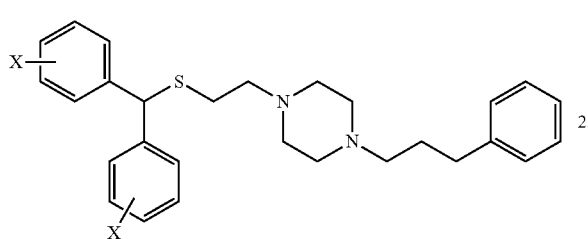

Scheme 5

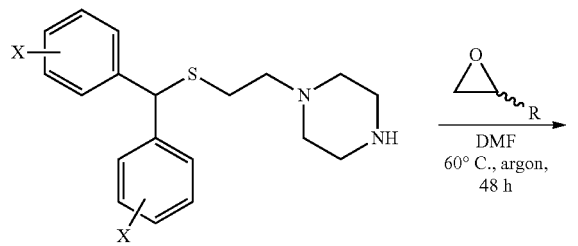

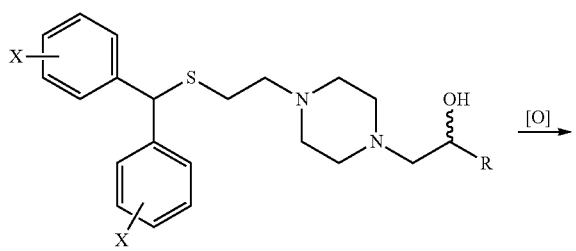

Scheme 6.

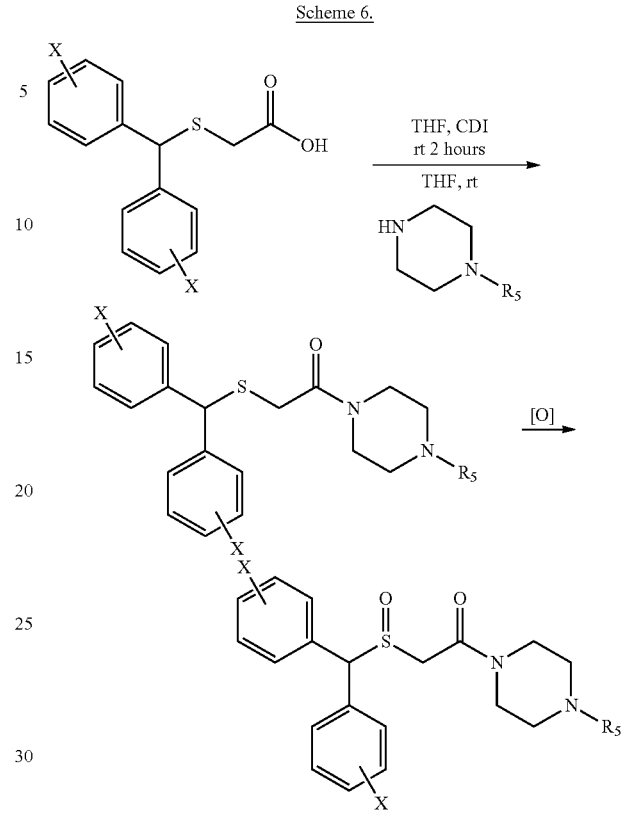

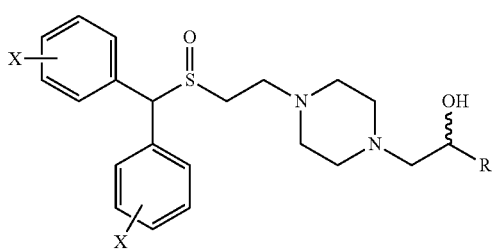

Generalized reaction conditions for obtaining piperazinyl derivatives diphenylmethanol is reacted with HSCH$_2$CH$_2$OH using trifluoroacetic acid and conditions according to BMCL 2007, 17(13), 3769-3773. The resulting alcohol is brominated using triphenyl phosphine and tetrabromomethane according to BMCL 2007, 17(13), 3769-3773. The brominated compound is coupled with piperazine using a procedure according to JMC 1999, 42(24), 5029-5042. In another approach, the brominated compound is coupled with a N-substituted piperazine (e.g. 1-3-phenylpropyl)piperazine or 1-(piperazin-1-yl)propan-2-ol in the presence of potassium carbonate in refluxing acetone.

The piperazine product of Scheme 3 is substituted according to general procedures as set out in Scheme 4. In a first step, the piperazine is alkylated with 1-bromo-3-phenylpropane using a procedure from Eur J Med Chem 1980, 15(4), 363-370. The sulfide can then be oxidized to the sulfoxide using conditions according to ACS-MCL 2011, 2(1), 48-52. For example, the sulfide can be oxidized using H$_2$O$_2$ in AcOH/MeOH 40° C. overnight.

The piperazine product of Scheme 3 is substituted according to general procedures as set out in Scheme 5. In a first step, the piperazine product of Scheme 3 is reacted with an epoxide (R=CH$_3$ or CH$_2$PH, racemic, R, or S isomer) using procedures according to BMCL 2003, 13, 553-556 or JMC 2002 45(6), 1321-1329. Alternatively, the piperazine product of Scheme 3 can be reacted with 1-chloro-2-hydroxy-3-phenylpropane (racemic, R, or S isomer) using N,N-diisopropylethylamine (N,N'-DIPEA), sodium iodide, in DMF at 60° C. according to procedures set out in JMC 2002, 45(6) 1321-1329. The resulting sulfide can then be oxidized to the sulfoxide using conditions according to ACS-MCL 2011, 2(1), 48-52.

Generalized reaction conditions for obtaining piperazinyl derivatives according to Scheme 6 are as follows: 2-(benzhydrylthio)acetic acid or an appropriately-substituted analog thereof is reacted with CDI in THF. A N-substituted piperazine in solution with THF is then added to form the sulfide product. The resulting sulfide can then be oxidized to the sulfoxide using conditions according to ACS-MCL 2011, 2(1), 48-52. For example, the sulfide can be oxidized using $H_2O_2$ in AcOH/MeOH 40° C. overnight.

Compounds that can be prepared according to Schemes 3-5 are provided in Table 3 and compounds that can be prepared according to Scheme 6 are provided in Table 4. It should be noted that analogs of the compounds in Tables 3 and 4 where X is in the meta position are fully contemplated.

TABLE 3

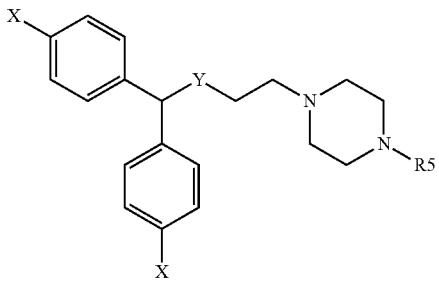

Compounds 6a-6e, 7a-7e, 8a-8e, 9a-9l, and 10a-10l

| Compound | X | Y | $R_5$ |
|---|---|---|---|
| 6a | H | S | H |
| 6b | F | S | H |
| 6c | Cl | S | H |
| 6d | $CH_3$ | S | H |
| 6e | $CF_3$ | S | H |
| 7a | H | S | 3-phenylpropyl |
| 7b | F | S | 3-phenylpropyl |
| 7c | Cl | S | 3-phenylpropyl |
| 7d | $CH_3$ | S | 3-phenylpropyl |
| 7e | $CF_3$ | S | 3-phenylpropyl |
| 8a | H | S=O | 3-phenylpropyl |
| 8b | F | S=O | 3-phenylpropyl |
| 8c | Cl | S=O | 3-phenylpropyl |
| 8d | $CH_3$ | S=O | 3-phenylpropyl |
| 8e | $CF_3$ | S=O | 3-phenylpropyl |
| 9a | H | S | —$CH_2CH(OH)CH_3$ (racemic) |
| 9b | H | S | —$CH_2CH(OH)CH_3$ (S configuration) |
| 9c | H | S | —$CH_2CH(OH)CH_3$ (R configuration) |
| 9d | F | S | —$CH_2CH(OH)CH_3$ (racemic) |
| 9e | F | S | —$CH_2CH(OH)CH_3$ (S configuration) |
| 9f | F | S | —$CH_2CH(OH)CH_3$ (R configuration) |
| 9g | H | S | —$CH_2CH(OH)CH_2Ph$ (racemic) |
| 9h | H | S | —$CH_2CH(OH)CH_2Ph$ (S configuration) |
| 9i | H | S | —$CH_2CH(OH)CH_2Ph$ (R configuration) |
| 9j | F | S | —$CH_2CH(OH)CH_2Ph$ (racemic) |
| 9k | F | S | —$CH_2CH(OH)CH_2Ph$ (S configuration) |
| 9l | F | S | —$CH_2CH(OH)CH_2Ph$ (R configuration) |
| 10a | H | S=O | —$CH_2CH(OH)CH_3$ (racemic) |
| 10b | H | S=O | —$CH_2CH(OH)CH_3$ (S configuration) |
| 10c | H | S=O | —$CH_2CH(OH)CH_3$ (R configuration) |
| 10d | F | S=O | —$CH_2CH(OH)CH_3$ (racemic) |
| 10e | F | S=O | —$CH_2CH(OH)CH_3$ (S configuration) |
| 10f | F | S=O | —$CH_2CH(OH)CH_3$ (R configuration) |
| 10g | H | S=O | —$CH_2CH(OH)CH_2Ph$ (racemic) |
| 10h | H | S=O | —$CH_2CH(OH)CH_2Ph$ (S configuration) |
| 10i | H | S=O | —$CH_2CH(OH)CH_2Ph$ (R configuration) |
| 10j | F | S=O | —$CH_2CH(OH)CH_2Ph$ (racemic) |
| 10k | F | S=O | —$CH_2CH(OH)CH_2Ph$ (S configuration) |
| 10l | F | S=O | —$CH_2CH(OH)CH_2Ph$ (R configuration) |

TABLE 4

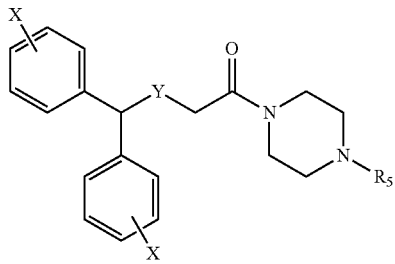

Compounds 11a-e, 12a-e, 13a-l, and 14a-l

| Compound | X (para) | Y | $R_5$ |
|---|---|---|---|
| 11a | H | S | 3-phenylpropyl |
| 11b | F | S | 3-phenylpropyl |
| 11c | Cl | S | 3-phenylpropyl |
| 11d | $CH_3$ | S | 3-phenylpropyl |
| 11e | $CF_3$ | S | 3-phenylpropyl |
| 12a | H | S=O | 3-phenylpropyl |
| 12b | F | S=O | 3-phenylpropyl |
| 12c | Cl | S=O | 3-phenylpropyl |
| 12d | $CH_3$ | S=O | 3-phenylpropyl |
| 12e | $CF_3$ | S=O | 3-phenylpropyl |
| 13a | H | S | —$CH_2CH(OH)CH_3$ (racemic) |
| 13b | H | S | —$CH_2CH(OH)CH_3$ (S configuration) |
| 13c | H | S | —$CH_2CH(OH)CH_3$ (R configuration) |
| 13d | F | S | —$CH_2CH(OH)CH_3$ (racemic) |
| 13e | F | S | —$CH_2CH(OH)CH_3$ (S configuration) |
| 13f | F | S | —$CH_2CH(OH)CH_3$ (R configuration) |
| 13g | H | S | —$CH_2CH(OH)CH_2Ph$ (racemic) |
| 13h | H | S | —$CH_2CH(OH)CH_2Ph$ (S configuration) |
| 13i | H | S | —$CH_2CH(OH)CH_2Ph$ (R configuration) |
| 13j | F | S | —$CH_2CH(OH)CH_2Ph$ (racemic) |
| 13k | F | S | —$CH_2CH(OH)CH_2Ph$ (S configuration) |
| 13l | F | S | —$CH_2CH(OH)CH_2Ph$ (R configuration) |
| 14a | H | S=O | —$CH_2CH(OH)CH_3$ (racemic) |
| 14b | H | S=O | —$CH_2CH(OH)CH_3$ (S configuration) |
| 14c | H | S=O | —$CH_2CH(OH)CH_3$ (R configuration) |
| 14d | F | S=O | —$CH_2CH(OH)CH_3$ (racemic) |
| 14e | F | S=O | —$CH_2CH(OH)CH_3$ (S configuration) |
| 14f | F | S=O | —$CH_2CH(OH)CH_3$ (R configuration) |
| 14g | H | S=O | —$CH_2CH(OH)CH_2Ph$ (racemic) |
| 14h | H | S=O | —$CH_2CH(OH)CH_2Ph$ (S configuration) |
| 14i | H | S=O | —$CH_2CH(OH)CH_2Ph$ (R configuration) |
| 14j | F | S=O | —$CH_2CH(OH)CH_2Ph$ (racemic) |
| 14k | F | S=O | —$CH_2CH(OH)CH_2Ph$ (S configuration) |
| 14l | F | S=O | —$CH_2CH(OH)CH_2Ph$ (R configuration) |

2-(Benzhydrylthio)ethan-1-ol Starting Material. 2-mercaptoethan-1-ol (7.8 g, 100 mmol) was added to diphenylmethanol (3.7 g, 20 mmol) in TFA (40 mL) and $CH_2Cl_2$ (40 mL) at 0° C. and the mixture was stirred at r.t. overnight. The solvent was removed and $K_2CO_3$ (11 g, 80 mmol), $H_2O$ (7 mL) and acetone (25 mL) were added to the reaction residue, and the mixture stirred at r.t. overnight. The solvent was removed, $H_2O$ (100 mL) was added to the residue obtained, and the aqueous mixture was extracted with ethyl acetate (3×100 mL). The organic layer was dried over $MgSO_4$ and the solvent was removed in vacuo. The crude product was purified by flash column chromatography (hexane/ethyl acetate=6:4) to give 2-(benzhydrylthio)ethan-1-ol (3.0 g, 61% yield) as a clear oil. GC/MS (EI) m/z 244 ($M^+$).

2-((Bis(4-fluorophenyl)methyl)thio)ethan-1-ol Starting Material. 2-((Bis(4-fluorophenyl)methyl)thio)ethan-1-ol was prepared as described for the preparation of 2-(benzhydrylthio)ethan-1-ol using bis(4-fluorophenyl)methanol (6.6 g, 30 mmol) to give the product (6.9 g, 82% yield) as a colorless oil. $^1$H NMR (CDCl$_3$): δ 7.35-7.39 (m, 4H), 6.99-7.03 (m, 4H), 5.20 (s, 1H), 3.68-3.70 (m, 2H), 2.59-2.62 (m, 2H).

Benzhydryl(2-bromoethyl)sulfane Starting Material. Triphenylphosphine (PPh$_3$) (1.4 g, 5.3 mmol) was added to a solution of 2-(benzhydrylthio)ethan-1-ol (890 mg, 3.64 mmol) in CH$_3$CN (12 ml), followed by the addition of carbon tetrabromide (CBr$_4$) (1.77 g, 5.34 mmol). The reaction mixture was stirred at r.t. overnight. The solvent was removed and the crude product was purified by flash column chromatography (hexane/ethyl acetate=5:1) to give the compound (850 mg, 76% yield) as a colorless oil GC/MS (EI) m/z 307 (M$^+$); $^1$H NMR (CDCl$_3$): δ 7.23-7.45 (m, 10OH), 5.23 (s, 1H), 3.33-3.39 (m, 2H), 2.80-2.90 (m, 2H).

(Bis(4-fluorophenyl)methyl)(2-bromoethyl)sulfane Starting Material. (bis(4-fluorophenyl)methyl)(2-bromoethyl)sulfane was prepared as described for benzhydryl(2-bromoethyl)sulfane using 2-((bis(4-fluorophenyl)methyl)thio)ethan-1-ol (6.9 g, 25 mmol) to give the product (7.0 g, 83% yield) as a light yellow oil. GC/MS (EI) m/z 343 (M$^+$); $^1$H NMR (CDCl$_3$): δ 7.34-7.37 (m, 4H), 6.00-7.04 (m, 4H), 5.21 (s, 1H), 3.36-3.40 (m, 2H), 2.81-2.85 (m, 2H).

1-(2-(Benzhydrylthio)ethyl)-4-(3-phenylpropyl)piperazine (7a). A mixture of benzhydryl(2-bromoethyl)sulfane (850 mg, 2.76 mmol), 1-(3-phenylpropyl)piperazine (564 mg, 2.76 mmol), K$_2$CO$_3$ (1.52 g, 11.0 mmol) and KI (catalytic amount) in acetone (30 mL) was stirred at reflux overnight. The solvent was removed, H$_2$O (50 mL) was added to the residue, and the aqueous mixture was extracted with ethyl acetate (3×50 ml). The organic layer was dried over MgSO$_4$ and solvent was removed and crude product was purified by flash column chromatography (ethyl acetate/triethylamine (TEA)=95:5) to give 7a (810 mg, 61% yield) as a yellow oil. The free base was converted to the oxalate salt and recrystallized from methanol to give a white solid. Mp 210° C. (dec.); $^1$H NMR (CDCl$_3$): δ 7.16-7.43 (m, 15H), 5.22 (s, 1H), 2.33-2.64 (m, 16H), 1.78-1.82 (m, 2H); $^{13}$C NMR (CDCl$_3$): 142.1, 141.4, 128.5, 128.4, 128.3, 127.2, 125.7, 58.0, 54.5, 54.4, 53.1, 53.0, 33.7, 29.3, 28.6; Anal. (C$_{28}$H$_{34}$N$_2$S.2C$_2$H$_2$O$_4$.0.25H$_2$O) C, H, N.

1-(2-((Bis(4-fluorophenyl)methyl)thio)ethyl)-4-(3-phenylpropyl)piperazine (7b). Compound 7b was prepared as described for 7a using (bis(4-fluorophenyl)methyl)(2-bromoethyl)sulfane (950 mg, 2.76 mmol) to give the product (940 mg, 73% yield) as a yellow oil. The free base was converted to the oxalate salt and recrystallized from methanol to give a white solid. Mp 216-217° C.; $^1$H NMR (CDCl$_3$): δ 7.34-7.37 (m, 4H), 7.24-7.29 (m, 2H), 7.15-7.19 (m, 3H), 6.97-7.01 (m, 4H), 5.20 (s, 1H), 2.33-2.64 (m, 16H), 1.67-1.82 (m, 2H); $^{13}$C NMR (CDCl$_3$): 163.1, 160.7, 142.1, 137.0, 129.8, 129.7, 128.4, 128.3, 125.7, 115.6, 115.3, 58.0, 53.1, 52.9, 52.8, 33.7, 29.4, 28.6; Anal. (C$_{28}$H$_{32}$F$_2$N$_2$S.2C$_2$H$_2$O$_4$) C, H, N.

1-(4-(2-(Benzhydrylthio)ethyl)piperazin-1-yl)propan-2-ol (9a). Compound 9a was prepared as described for 7a using benzhydryl(2-bromoethyl)sulfane (848 mg, 2.76 mmol) and 1-(piperazin-1-yl)propan-2-ol (398 mg, 2.76 mmol) to give the product (850 mg, 83% yield) as a yellow oil. The free base was converted to the oxalate salt and recrystallized from methanol to give a white solid. Mp 209-210° C.; $^1$H NMR (CDCl$_3$): δ 7.41-7.43 (m, 4H), 7.19-7.32 (m, 6H), 5.21 (s, 1H), 3.77-3.82 (m, 1H), 3.41 (br, 1H), 2.17-2.67 (m, 14H), 1.11-1.14 (m, 3H); $^{13}$C NMR (CDCl$_3$) 141.4, 128.6, 128.5, 128.3, 127.2, 65.6, 62.2, 57.9, 54.5, 54.4, 53.1, 29.3, 20.0; Anal. (C$_{22}$H$_{30}$N$_2$OS.2C$_2$H$_2$O$_4$.0.25H$_2$O) C, H, N.

1-(4-(2-((Bis(4-fluorophenyl)methyl)thio)ethyl)piperazin-1-yl)propan-2-ol (9d). Compound 9d was prepared as described for 7a using (bis(4-fluorophenyl)methyl)(2-bromoethyl)sulfane (950 mg, 2.76 mmol) and 1-(piperazin-1-yl)propan-2-ol (398 mg, 2.76 mmol) to give the product (880 mg, 79% yield) as a yellow oil. The free base was converted to the oxalate salt and recrystallized from methanol to give a white solid. Mp 205-206° C.; $^1$H NMR (CDCl$_3$): δ 7.33-7.37 (m, 4H), 6.96-7.02 (m, 4H), 5.19 (s, 1H), 3.77-3.82 (m, 1H), 3.41 (br, 1H), 2.18-2.69 (m, 14H), 1.11-1.13 (m, 3H); $^{13}$C NMR (CDCl$_3$) 163.1, 160.7, 137.0, 129.8, 129.7, 115.7, 115.6, 115.5, 115.4, 65.5, 62.2, 57.8, 53.1, 52.9, 29.4, 20.0; Anal. (C$_{22}$H$_{28}$F$_2$N$_2$OS.2C$_2$H$_2$O$_4$) C, H, N.

1-(2-(Benzhydrylthio)ethyl)piperazine Starting Material. A mixture of benzhydryl(2-bromoethyl)sulfane (1.4 g, 4.6 mmol), piperazine (2.35 g, 27.3 mmol), and K$_2$CO$_3$ (1.05 g, 9.12 mmol) in acetonitrile (25 mL) was stirred at reflux overnight. The solvent was removed, H$_2$O (100 mL) was added to the residue, and the aqueous mixture was extracted with ethyl acetate (3×100 mL). The organic layer was dried over MgSO$_4$ and solvent was removed in vacuo. The crude product was purified by flash column chromatography (CHCl$_3$/MeOH/NH$_4$OH=90:10:0.5) to give the product (710 mg, 50% yield) as a yellow oil. $^1$H NMR (CDCl$_3$): δ 7.41-7.43 (m, 4H), 7.19-7.32 (m, 6H), 5.22 (s, 1H), 2.83-2.85 (m, 4H), 2.52-2.54 (m, 4H), 2.34-2.37 (m, 4H).

1-(2-((Bis(4-fluorophenyl)methyl)thio)ethyl)piperazine Starting Material. 1-(2-((Bis(4-fluorophenyl)methyl)thio)ethyl)piperazine was prepared as described for 1-(2-(benzhydrylthio)ethyl)piperazine using (bis(4-fluorophenyl)methyl)(2-bromoethyl)sulfane (1.03 g, 3.00 mmol) to give the product (910 mg, 87% yield) as a yellow oil. $^1$H NMR (CDCl$_3$): δ 7.34-7.37 (m, 4H), 6.97-7.26 (m, 4H), 5.20 (s, 1H), 2.84-2.86 (m, 4H), 2.50-2.52 (m, 4H), 2.35-2.37 (m, 4H).

1-(2-(Benzhydrylsulfinyl)ethyl)-4-(3-phenylpropyl)piperazine 8a. Compound 8a was prepared as previously described using 7a (431 mg, 1.00 mmol) to give the product (250 mg, 56% yield) as a yellow oil. The free base was converted to the hydrochloride salt and recrystallized from methanol to give a white solid. Mp 210° C. (dec.); $^1$H NMR (CDCl$_3$): δ 7.15-7.50 (m, 15H), 4.96 (s, 1H), 2.33-2.82 (m, 16H), 1.76-1.84 (m, 2H); $^{13}$C NMR (CDCl$_3$): 142.1, 136.0, 135.2, 129.3, 129.2, 128.7, 128.4, 128.3, 128.2, 125.8, 72.1, 57.9, 53.4, 53.0, 51.0, 48.2, 33.7, 28.6; Anal. (C$_{28}$H$_{34}$N$_2$OS.2HCl.0.5H$_2$O) C, H, N.

1-(2-((Bis(4-fluorophenyl)methyl)sulfinyl)ethyl)-4-(3-phenylpropyl)piperazine 8b. Compound 8b was prepared as described for 8a using 1-(2-((bis(4-fluorophenyl)methyl)thio)ethyl)-4-(3-phenylpropyl)piperazine (466 mg, 1.00 mmol) to give the product (290 mg, 60% yield) as a yellow oil. The free base was converted to the oxalate salt and recrystallized from methanol to give a white solid. Mp 204° C. (dec.); $^1$H NMR (CDCl$_3$): δ 7.37-7.40 (m, 4H), 7.24-7.28 (m, 2H), 7.16-7.19 (m, 3H), 7.05-7.11 (m, 4H), 4.95 (s, 1H), 2.34-2.79 (m, 16H), 1.76-2.04 (m, 2H); $^{13}$C NMR (CDCl$_3$): 164.0, 163.8, 161.6, 142.1, 131.0, 130.6, 130.3, 128.4, 128.3, 125.8, 116.4, 116.2, 115.9, 115.6, 68.8, 68.2, 65.8, 57.9, 53.0, 50.9, 48.1, 33.7, 28.5; Anal. (C$_{28}$H$_{32}$F$_2$N$_2$OS.2C$_2$H$_2$O$_4$.H$_2$O) C, H, N.

1-(4-(2-(Benzhydrylsulfinyl)ethyl)piperazin-1-yl)propan-2-ol (10a). Compound 10a was prepared as described for 8a using 9a (556 mg, 1.50 mmol) to give the product (450 mg, 78% yield) as a white solid. The free base was converted to the oxalate salt and recrystallized from methanol to give a white solid. Mp 195-197° C. (dec.); $^1$H NMR (CDCl$_3$): δ 7.30-7.49 (m, 10OH), 4.95 (s, 1H), 3.78-3.82 (m, 1H), 3.39 (br, 1h), 2.18-2.83 (m, 14H), 1.11-1.12 (m, 3H); $^{13}$C NMR (CDCl$_3$): 136.0, 135.1, 129.3, 129.2, 128.7, 128.6, 128.3, 72.2, 65.5, 62.2, 53.1, 50.9, 48.3, 20.0; Anal ($C_{22}H_{30}N_2O_2S \cdot 2C_2H_2O_4 \cdot 0.25H_2O$) C, H, N.

1-(4-(2-((Bis(4-fluorophenyl)methyl)sulfinyl)ethyl)piperazin-1-yl)propan-2-ol (10d). Compound 10d was prepared as described for 8a using 9d (610 mg, 1.50 mmol) to give the product (340 mg, 54% yield) as a yellow oil. The free base was converted to the oxalate salt and recrystallized from methanol to give a white solid. Mp 190-191° C. (dec.); $^1$H NMR (CDCl$_3$): δ 7.36-7.43 (m, 4H), 7.04-7.12 (m, 4H), 4.92 (s, 1H), 3.77-3.83 (m, 1H), 2.22-2.84 (m, 14H), 1.11-1.12 (m, 3H); $^{13}$C NMR (CDCl$_3$): 164.0, 163.8, 161.6, 161.3, 131.7, 131.0, 130.6, 130.5, 130.4, 130.3, 116.4, 116.2, 115.9, 115.6, 69.9, 69.8, 65.5, 62.3, 53.1, 50.8, 48.3, 20.0; Anal. ($C_{22}H_{28}F_2N_2O_2S \cdot 2C_2H_2O_4$) C, H, N.

1-(4-(2-(Benzhydrylthio)ethyl)piperazin-1-yl)-3-phenylpropan-2-ol (9g). A solution of compound 1-(2-(benzhydrylthio)ethyl)piperazine (710 mg, 2.27 mmol) and 2-benzyloxirane (304.6 mg, 2.27 mmol) in 2-propanol (24 mL) was stirred at reflux overnight. Solvent was removed and the reaction residue was purified by flash column chromatography (hexane/ethyl acetate/triethylamine (TEA)=50:50:2) to give 9g (850 mg, 84% yield) as a yellow oil. The free base was converted to the oxalate salt and recrystallized from hot 2-propanol to give a white solid. Mp 210-211° C.; $^1$H NMR (CDCl$_3$): δ 7.40-7.43 (m, 4H), 7.20-7.32 (m, 11H), 5.22 (s, 1H), 3.88-3.93 (m, 1H), 3.45 (br, 1H), 2.27-2.83 (m, 16H); $^{13}$C NMR (CDCl$_3$): 141.4, 138.3, 129.3, 128.6, 128.5, 128.3, 127.3, 127.2, 126.3, 67.2, 63.4, 57.9, 54.4, 53.1, 41.3, 29.3; Anal. ($C_{28}H_{34}N_2OS \cdot 2C_2H_2O_4 \cdot 0.5H_2O$) C, H, N.

1-(4-(2-((Bis(4-fluorophenyl)methyl)thio)ethyl)piperazin-1-yl)-3-phenylpropan-2-ol (9j). Compound 9j was prepared as described for 9g using 1-(2-((bis(4-fluorophenyl)methyl)thio)ethyl)piperazine (455 mg, 1.31 mmol) to give the product (540 mg, 86% yield) as a yellow oil. The free base was converted to the oxalate salt and recrystallized from hot acetone to give a white solid. Mp 206-207° C.; $^1$H NMR (CDCl$_3$): δ 7.19-7.37 (m, 9H), 6.96-7.02 (m, 4H), 5.18 (s, 1H), 3.45 (br, 1H), 3.88-3.93 (m, 1H), 2.31-2.81 (m, 16H); $^{13}$C NMR (CDCl$_3$): 163.1, 160.7, 138.2, 137.0, 129.8, 129.7, 129.3, 128.3, 126.3, 115.6, 115.4, 67.2, 63.4, 57.8, 53.1, 52.9, 41.3, 29.4; Anal. ($C_{28}H_{32}F_2N_2OS \cdot 2C_2H_2O_4 \cdot 0.25H_2O$) C, H, N.

1-(4-(2-(Benzhydrylsulfinyl)ethyl)piperazin-1-yl)-3-phenylpropan-2-ol (10g). Compound 10g was prepared as described for 8a using 9g (534 mg, 1.20 mmol) to give the product (340 mg, 61% yield) as a yellow oil. The free base was converted to the oxalate salt and recrystallized from hot methanol to give a white solid. Mp 198-200° C. (dec.); $^1$H NMR (CDCl$_3$): δ 7.20-7.49 (m, 15H), 4.95 (s, 1H), 3.88-3.92 (m, 1H), 2.31-2.83 (m, 16H); $^{13}$C NMR (CDCl$_3$): 138.2, 136.0, 135.2, 129.3, 129.2, 128.9, 128.7, 128.6, 128.4, 128.3, 126.3, 72.1, 67.3, 63.4, 53.0, 50.8, 48.2, 41.3; Anal. ($C_{28}H_{34}N_2O_2S \cdot 2C_2H_2O_4 \cdot 0.25H_2O$) C, H, N.

1-(4-(2-((Bis(4-fluorophenyl)methyl)sulfinyl)ethyl)piperazin-1-yl)-3-phenylpropan-2-ol (10j). Compound 10j was prepared as described for 8a using 9j (400 mg, 0.83 mmol) to give the product (280 mg, 68% yield) as a yellow oil. The free base was converted to the oxalate salt and recrystallized from hot methanol to give a white solid. Mp 198-200° C. (dec.); $^1$H NMR (CDCl$_3$): δ 7.20-7.43 (m, 13H), 7.05-7.11 (m, 4H), 4.93 (s, 1H), 3.88-3.92 (m, 1H), 2.29-2.84 (m, 16H); $^{13}$C NMR (CDCl$_3$): 161.6, 161.3, 138.2, 131.8, 131.0, 130.9, 130.5, 130.3, 129.3, 128.4, 126.3, 116.4, 116.2, 115.9, 115.6, 69.4, 67.3, 63.4, 53.1, 50.8, 48.2, 41.3, Anal. ($C_{28}H_{32}F_2N_2O_2S \cdot 2C_2H_2O_4$) C, H, N.

2-(Benzhydrylthio)-1-(4-(3-phenylpropyl)piperazin-1-yl)ethan-1-one (1a). A mixture of CDI (583 mg, 3.60 mmol) and 2-(benzhydrylthio)acetic acid (775 mg, 3.00 mmol) in THF (24 mL) was stirred at r.t. under argon. After 2 hours of reaction time, 1-(3-phenylpropyl)piperazine (613 mg, 3.00 mmol) in THF (15 mL) was added and the reaction mixture was stirred overnight. Solvent was removed and the reaction residue was purified by flash column chromatography (ethyl acetate/triethylamine (TEA)=95:5) to give 11a (1.2 g, 90% yield) as a yellow oil. The free base was converted to the oxalate salt and recrystallized from hot 2-propanol to give a white solid. Mp 92-95° C.; $^1$H NMR (CDCl$_3$): δ 7.42-7.45 (m, 4H), 7.17-7.33 (m, 11H), 5.34 (s, 1H), 3.57-3.60 (t, 2H, J=14.1 Hz), 3.37-3.40 (t, 2H, J=5.2 Hz), 3.18 (s, 2H), 2.62-2.66 (m, 2H), 2.34-2.39 (m, 6H), 1.78-1.84 (m, 2H); $^{13}$C NMR (CDCl$_3$): 167.2, 141.9, 140.7, 128.6, 128.5, 128.4, 128.3, 127.3, 125.8, 57.7, 54.1, 53.2, 52.7, 46.3, 41.9, 33.5, 28.4; Anal. ($C_{28}H_{32}N_2OS \cdot C_2H_2O_4 \cdot 0.5H_2O$) C, H, N.

2-(Benzhydrylsulfinyl)-1-(4-(3-phenylpropyl)piperazin-1-yl)ethan-1-one (12a). Compound 12a was prepared as described for 8a using 11a (667 mg, 1.50 mmol) to give the product (500 mg, 72%) as a yellow oil. The free base was converted to the oxalate salt and recrystallized from hot acetone to give a white solid. Mp 180-182° C.; $^1$H NMR (CDCl$_3$): δ 7.49-7.55 (m, 4H), 7.16-7.43 (m, 11H), 5.30 (s, 1H), 3.27-3.70 (m, 6H), 2.61-2.65 (m 2H), 2.33-2.47 (m, 6H), 1.75-1.83 (m, 2H); $^{13}$C NMR (CDCl$_3$): 163.1, 141.9, 136.0, 133.6, 130.0, 129.1, 129.0, 128.7, 128.5, 128.4, 128.3, 128.2, 125.8, 70.1, 70.0, 57.5, 53.1, 52.6, 46.4, 42.0, 33.5, 28.4; Anal. ($C_{28}H_{32}N_2O_2S \cdot C_2H_2O_4 \cdot 0.25H_2O$) C, H, N.

Example 5

Binding Affinity Data at Monoamine Transporters for Piperazinyl Derivatives

Binding affinities of several piperazinyl compounds of Example 4 were evaluated at the DAT, SERT, and NET in rat brain membranes using previously described methods as in Example 3. The results are provided in Table 5 along with the compound's CLogP.

TABLE 5

| compound | DAT Ki ± SEM (nM) | NET Ki ± SEM (nM) | SERT Ki ± SEM (nM) | Sigma 1 Ki ± SEM (nM) | Sigma 2 Ki ± SEM (nM) | CLogP |
|---|---|---|---|---|---|---|
| 7a | 3.58 ± 0.16 | 988 ± 22.8 | 1050 ± 152 | 19.9 ± 2.59 | 16.8 ± 2.15 | 5.87 |
| 8a | 3.17 ± 0.11 | 5540 ± 808 | 7220 ± 944 | 116 ± 1.24 | 20.5 ± 0.43 | 3.91 |
| 7b | 4.50 ± 0.34 | 1890 ± 116 | 285 ± 35.4 | 59.5 ± 5.04 | 28.5 ± 2.14 | 6.12 |
| 8b | 2.92 ± 0.38 | 4281 ± 343 | 678 ± 66.1 | 42.4 ± 5.10 | 25.9 ± 1.11 | 4.20 |
| 9j | 6.72 ± 0.98 | 1950 ± 227 | 213 ± 13.2 | 95.4 ± 13.4 | 38.6 ± 0.94 | 5.00 |
| 10j | 2.53 ± 0.25 | 15000 ± 575 | 4610 ± 562 | 336 ± 42.2 | 176 ± 26.3 | 3.06 |

TABLE 5-continued

| compound | DAT Ki ± SEM (nM) | NET Ki ± SEM (nM) | SERT Ki ± SEM (nM) | Sigma 1 Ki ± SEM (nM) | Sigma 2 Ki ± SEM (nM) | CLogP |
|---|---|---|---|---|---|---|
| 9d | 16.7 ± 1.22 | 17800 ± 885 | 1770 ± 234 | 4.03 ± 0.22 | 84.7 ± 11.9 | 3.42 |
| 10d | 289 ± 43.0 | >1e-4M | 50300 ± 5760 | 1010 ± 134 | 1800 ± 264 | 1.49 |
| 9a | 49.6 ± 4.31 | 44500 ± 2400 | 26700 ± 2630 | 0.94 ± 0.07 | 92.6 ± 13.5 | 3.13 |
| 10a | 636 ± 14.7 | >1e-4M | >1e-4M | 861 ± 109 | 3930 ± 208 | 1.21 |
| 9g | 2.54 ± 0.23 | 1430 ± 118 | 1630 ± 169 | 30.0 ± 3.81 | 31.8 ± 3.63 | 4.70 |
| 10g | 3.43 ± 0.5 | 25300 ± 2040 | 21700 ± 2020 | 983 ± 103 | 316 ± 25.2 | 2.78 |
| 11a | 47.2 ± 5.56 | 22600 ± 3010 | 9320 ± 932 | 1120 ± 20.3 | 773 ± 86.23 | 6.37 |
| 12a | 33.0 ± 2.83 | 54300 ± 3210 | 15200 ± 1100 | 1430 ± 21.1 | 469 ± 66.4 | 4.67 |

Example 6

Molecular Docking and Mutagenesis Studies

Molecular Pharmacology Site-Directed Mutagenesis:

Synthetic cDNA encoding the human DAT (synDAT) were subcloned into pcDNA3 (Invitrogen, Carlsbad, Calif.). cDNA encoding the human SERT (hSERT) was cloned into the pUbilz expression vector. Mutations herein were generated by the QuickChange method (adapted from Stratagene, La Jolla, Calif.) and confirmed by restriction enzyme mapping and DNA sequencing. Positive clones were amplified by transformation into XL1 blue competent cells (Stratagene) and positive colony picked and grown in LB media over night at 37° C. in an orbital incubator (Infors) @200 rpm. Plasmids were harvested using the maxi prep kit provided by Qiagen according to the manufacturer's manual.

Cell Culture and Transfection:

COS-7 cells were grown in Dulbecco's modified Eagle's medium 041 01885 supplemented with 10% fetal calf serum, 2 mM L-glutamine and 0.01 mg/mL gentamicin at 37° C. in 10% $CO_2$. Wild type and mutant constructs were transiently transfected into COS-7 cells with Lipo2000 (Invitrogen) according to manufacturer's manual using a cDNA:Lipo2000 ratio of 3:6 and 2:6 for hDAT and hSERT, respectively.

[$^3$H]Dopamine and [$^3$H]5-HT Uptake Experiments:

Uptake assays were performed essentially as previously described to Cha, J. H.; Zou, M. F.; Adkins, E. M.; Rasmussen, S. G.; Loland, C. J.; Schoenenberger, B.; Gether, U.; Newman, A. H. Rhodamine-Labeled 2beta-Carbomethoxy-3beta-(3,4-Dichlorophenyl)Tropane Analogues as High-Affinity Fluorescent Probes for the Dopamine Transporter. J. Med. Chem. 2005, 48, 7513-7516 using [2,5,6,7,8-$^3$H]Dihydroxyphenylethylamine ([$^3$H]DA, 94.4 Ci/mmol, Perkin Elmer) or 5-[1,2-$^3$H(N)]-hydroxytryptamine ([$^3$H]5-HT, 28 Ci/mmol, Perkin Elmer) for hDAT and hSERT expressing cells, respectively. Transiently transfected COS-7 cells were plated in 12-well (3*10$^5$ cells/well) or 24-well dishes (10$^5$ cells/well) coated with poly-ornithine to achieve an uptake level of no more than 10% of total added radioligand. The uptake assays were carried out 2 days after transfection. Prior to the experiment, the cells were washed once in 500 μl of uptake buffer (25 mM 4-(2-hydroxyethyl)-1-piperazineethanesulfonic acid (HEPES), 130 mM NaCl, 5.4 mM KCl, 1.2 mM $CaCl_2$, 1.2 mM $MgSO_4$, 1 mM L-ascorbic acid, 5 mM D-glucose, and 1 μM of the catechol-O-methyltransferase inhibitor Ro 41-0960 (Sigma), pH 7.4) at room temperature (RT). The unlabeled ligand (e.g. modafinil [(±)-1] or analogues) was added to the cells in 10 concentrations from 1 nM to 0.1 mM equally distributed around the expected $IC_{50}$ value, and uptake was initiated by addition of ~10 nM radioligand in a final volume of 500 μL. After 3 (for the hSERT) or 5 (hDAT) min of incubation, the reaction was stopped by rapid wash with 2×500 μL of ice cold uptake buffer, lysed in 250 μL (300 μL for 12-well plates) 1% SDS and left for 30 min at 37° C. with gentle shaking. All samples were transferred to 24-well counting plates and 500 μL (or 600 μL) of Optiphase Hi Safe 3 scintillation fluid (Perkin Elmer) was added followed by counting of the plates in a Wallac Tri-Lux β-scintillation counter (Perkin Elmer). Nonspecific uptake was determined in the presence of 5 μM paroxetine for hSERT and 50 μM nomifensine for hDAT expressing cells. All determinations were performed in triplicate.

Molecular Modeling: compound 2h was docked in a LeuT-based SERT model. The preparation and MD equilibration of the homology model of SERT was described in Plenge, P.; Shi, L.; Beuming, T.; Te, J.; Newman, A. H.; Weinstein, H.; Gether, U.; Loland, C. J. Steric Hindrance Mutagenesis in the Conserved Extracellular Vestibule Impedes Allosteric Binding of Antidepressants to the Serotonin Transporter. J. Biol. Chem. 2012, 287, 39316-39326. The compound was constructed and prepared for docking using LigPrep (Schrodinger Inc., Portland, Oreg.). Docking of the compound was carried out with Glide (Schrodinger Inc., Portland, Oreg.). The binding modes shown in FIG. 1 were chosen based on both the docking scores and the consistency to the (±)-modafinil pose in the previously modeled DAT-(±)-modafinil complexes.

To interpret SAR revealed by radioligand binding studies in the context of ligand-transporter interactions, we carried out molecular docking studies with both DAT and SERT homology models that are based on the crystal structure of the bacterial homologue, LeuT. These studies led to the identification of a key divergent position in transmembrane helix 10 (TM10), T497 in SERT and A480 in DAT that appears to contribute to the DAT vs. SERT selectivity. Previously A479 and A480 of DAT were found to be involved in the binding of benztropine (3α-diphenylmethoxytropane) and its derivatives, the atypical DAT inhibitors, many of which do not exert cocaine-like subjective effects. In contrast, the mutation of these two residues did not significantly affect the binding of a cocaine analogue WIN 35,428 (2β-carbomethoxy 3β-(4-fluorophenyl)tropane). In addition, it has been reported that the covalent modification on T497C of SERT by the cysteine reactive MTSET ([2-(trimethyl-ammonium)ethyl]-methanethiosulfonate) disrupted activity.

It is clear from the SAR described herein, that reduction of the amide to a secondary or primary amine significantly improves binding affinities at all three monoamine transporters (e.g., 2a vs. 4a). This effect appears to be most consistent at DAT, as all but a few analogues in Table 2 have submicromolar affinities. Interestingly, when the diphenyl ring system is substituted with either para-Cl or Br groups, the binding affinities at SERT are more improved than at DAT in all cases and most dramatically with, compounds 4b and 4c that bind with $K_i$ values≤30 nM at SERT, suggesting a specific interaction at the para-position that may differ between these two transporters. To investigate this further, molecular docking studies were conducted with a group of representative compounds using the homology models of DAT and SERT based on the crystal structure of LeuT to compare the difference of their binding modes for these targets.

Previously, it was proposed that the sulfoxide O interacted with the conserved Y156 in DAT. The residue immediately before Y156 is divergent among monoamine transporters: whereas in DAT this residue is phenylalanine (F155), the aligned position in SERT/NET is a tyrosine. Molecular docking studies revealed that while both F155 in DAT and Y175 in SERT directly interact with (±)-modafinil, this molecule differentially affects how Y156 of DAT and Y176 of SERT are positioned when bound. Thus the S=O is optimally positioned to interact with Y156 of DAT but not Y176 of SERT. If the S=O cannot properly interact with the conserved Tyr in SERT, the S=O contributes negatively to binding affinity and as a result (±)-modafinil has higher affinity for DAT than SERT. Conversely, absence of the sulfoxide oxygen should increase the affinity for SERT. Consistent with this prediction, in the presence of the carbonyl oxygen of the amide [(±)-modafinil vs. compound 2a, Table 1], reducing the S=O decreased the binding affinity for DAT but increased the affinity for SERT. Nevertheless, when either of the phenyl rings was substituted with halogens (2e vs. 3d) or the terminal amide was substituted (3f vs. 2g), this trend was not consistently observed underscoring the influence of these additional substituents on binding mode in both DAT and SERT. Note the binding affinities at SERT are so low for these analogues, it is difficult to determine a specific trend.

By reducing the amide carbonyl, the N becomes positively charged, resulting in an increase in affinity for all three monoamine transporters as described above [compare (±)-modafinil vs. 5a]. An interpretation is that the positive charge facilitates direct interaction between the N and the negatively charged Asp in the Na1 site, for all three transporters. Additionally, the combined effect of a global reduction of both the amide carbonyl and sulfoxide oxygens is even higher affinities at the DAT, SERT and NET, suggesting that the impact of the charged N is dominant compared to removal of the sulfoxide O, especially for DAT and SERT (compare (±)-modafinil to 5a vs. (±)-modafinil to 4a].

For amide analogues (2g vs. 2i) the presence of a Br substituent in the para-position likely causes a drug-receptor interaction (halogen bond formation) with T497 in SERT, thus improving binding affinity. However, the aligned position, A480 in DAT, prevents the formation of a halogen-bond with the Br substituent as in SERT and thus no improvement in DAT affinity is observed. Indeed, as noted above, in the amine series the reverse order of halogen effects on DAT binding is observed as compared to the acetamides, suggesting that halogen bond formation is unlikely.

To test the hypothesis that these residues in TM10 are part of the primary substrate/inhibitor (S1) binding site and play different roles in DAT vs. SERT binding for para-halogenated analogues in this series, two chimera mutants were created in DAT and SERT in which the residues are interchanged, resulting in DAT-A480T and SERT-T497A. The effect of the mutations on uptake inhibition potency for compounds with a Cl substituent in the para-position were measured on intact COS-7 cells transiently expressing wild types or the Ala and Thr substituted mutants (Tables 6 and 7). The affinity of (±)-modafinil is increased in DAT A480T (~5 fold) and perhaps slightly in the SERT T497A mutant, compared to their corresponding wild types. In addition, whereas the affinity of the para-Cl substituted thioacetamide 2h (a secondary amide) is significantly decreased at the SERT T497A compared to SERT WT (Table 7), suggesting a direct interaction between the para-Cl and the side chain of T497 (FIG. 1), the affinity of 2h at the DAT-A480T is essentially the same as at DAT-WT, similar to 2g that does not possess the para-Cl substituent (Table 6).

TABLE 6

[³H]DA uptake inhibition potency for selected analogues measured in intact COS7 cells expressing human DAT wild type or the A480T mutant[a]

| Compound | hDAT WT $K_i$ [S.E. interval] (nM) | n | hDAT A480T $K_i$ [S.E. interval] (nM) | n |
|---|---|---|---|---|
| Dopamine ($K_M$) | 1,160[980; 1,380] | 9 | 1,930[1,510; 2,480] | 5 |
| (±)-modafinil | 13,000[10,000; 17,000] | 6 | 3,090[2,300; 4,200] | 3 |
| 2g | 5,500[4,000; 7,600] | 4 | 3,600[2,010; 6,300] | 3 |
| 2h | 3,700[2,700; 5,100] | 5 | 2,300[1,700; 3,100] | 3 |
| 4a | 390[280; 540] | 3 | 720[620; 830] | 4 |
| 4b | 1,210[960; 1,510] | 5 | 1,370[1,240; 1,510] | 3 |

[a]The inhibition potency for [³H]dopamine (DA) uptake were calculated from non-linear regression analysis of uptake experiments performed on COS7 cells transiently transfected with cDNA of the human dopamine transporter (hDAT) wild type (WT) or the Ala480 to Thr mutant (A480T). The $IC_{50}$ values used in the calculation of $K_M$ and $K_i$ were calculated from means of $pIC_{50}$ and the indicated S.E. intervals were calculated from $pIC_{50}$ ± S.E. Non-specific uptake was determined using 50 µM nomifensine. All experiments were performed in triplicate.

TABLE 7

[³H]5-HT uptake inhibition potency for selected analogues measured in intact COS7 cells expressing human SERT wild type or the T497A mutant[a]

| Compound | hSERT WT $K_i$ [S.E. interval] (nM) | n | hSERT T497A $K_i$ [S.E. interval] (nM) | n |
|---|---|---|---|---|
| 5-HT ($K_M$) | 520[360; 760] | 7 | 1,090[840; 1,430] | 4 |
| (±)-modafinil | IA[b] | 3 | 570,000[497,000; 653,000][c] | 3 |
| 2g | IA[b] | 3 | IA[b] | 3 |
| 2h | 8,300[6,000; 11,600] | 3 | 27,000[14,000; 53,000] | 2 |

TABLE 7-continued

[³H]5-HT uptake inhibition potency for selected analogues measured in intact COS7 cells expressing human SERT wild type or the T497A mutant[a]

| Compound | hSERT WT $K_i$ [S.E. interval] (nM) | n | hSERT T497A $K_i$ [S.E. interval] (nM) | n |
| --- | --- | --- | --- | --- |
| 4a | 690[590; 810] | 4 | 630[550; 720] | 3 |
| 4b | 270[230; 330] | 3 | 170[91; 320] | 3 |

[a]The inhibition potency for [³H]serotonin (5-HT) uptake were calculated from non-linear regression analysis of uptake experiments performed on COS7 cells transiently transfected with cDNA of the human serotonin transporter (hSERT) wild type (WT) or the Thr497 to Ala mutant (T497A). The $IC_{50}$ values used in the calculation of $K_M$ and $K_i$ were calculated from means of $pIC_{50}$ and the indicated S.E. intervals were calculated from $pIC_{50}$ ± S.E. Non-specific uptake was determined using 5 μM paroxetine. All experiments were performed in triplicate.
[b]IA; Inactive - defined as <50% inhibition at 100 μM.
[c]According to the definition, (±)-modafinil would be IA. However, it was possible to determine a $K_i$ value and although the affinity for the T497A mutant was very low, it was in fact, higher than at the WT SERT, where no $K_i$ could be determined.

These results support the hypothesis that halogen bond interactions at SERT T497 affect binding affinities of these analogues. It is also hypothesized that a change of affinity might result for the A480T DAT mutant, however it was found that binding affinity was not affected by this mutation. Hence, these data also suggest that the binding sites of DAT and SERT obviously have other divergences beyond this single residue position—how the rest of the binding sites of DAT and SERT change in response to the mutations are different—and simply switching the residues at this position is not enough to interconvert the specificity of the compounds. For example, in both DAT and SERT, the affinities of 4a and 4b (both primary amines) remain unchanged at the mutants, suggesting that the exact configuration near the terminal nitrogen, either amide or charged nitrogen, has a strong impact on the orientation of the diphenylmethyl moiety in both transporters. Taken together, this residue position of TM10 appears to be more important for binding of the amide derivatives of (±)-modafinil with a para-Cl substituent at the SERT, compared to binding at the DAT. If the amide function is reduced to an amine, the relative importance of interaction at these residues is diminished.

Consistent with this understanding, at the SERT, the difference in binding affinity for halogen-substituted thioacetamides is more pronounced in compounds lacking a charged N (e.g., >50-fold increase in SERT affinity for amides 2i v. 2g in Table 1 and only a 9-fold increase in SERT affinity for amines 4c v. 4a in Table 2). In both cases, improvements in DAT affinity were diminished compared to SERT with only a 6-fold improvement in DAT affinity between 2i and 2g and only a 3-fold improvement for DAT affinity between 4c and 4a. In contrast, moving the halogen substituent to the meta-position as in compounds 2e and 3d has little if any effect on SERT binding, hence a decrease in or no change in binding affinity resulted compared to compound 2a and (±)-modafinil, respectively. However, the halogen substituent in the meta-position appears to generate new interactions that favor binding to the DAT, further supporting the influence of other residue divergences in the binding sites of DAT and SERT to compound affinity. It is proposed that substitution at the meta-position may be more favorable for designing DAT-over-SERT-selective analogues of (±)-modafinil.

Example 7

Mouse Locomotor Activity Test, Compound 4g

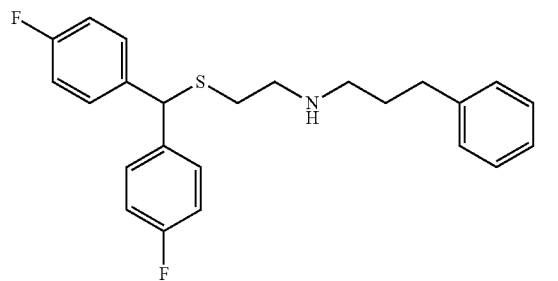

4g

Figure 2:
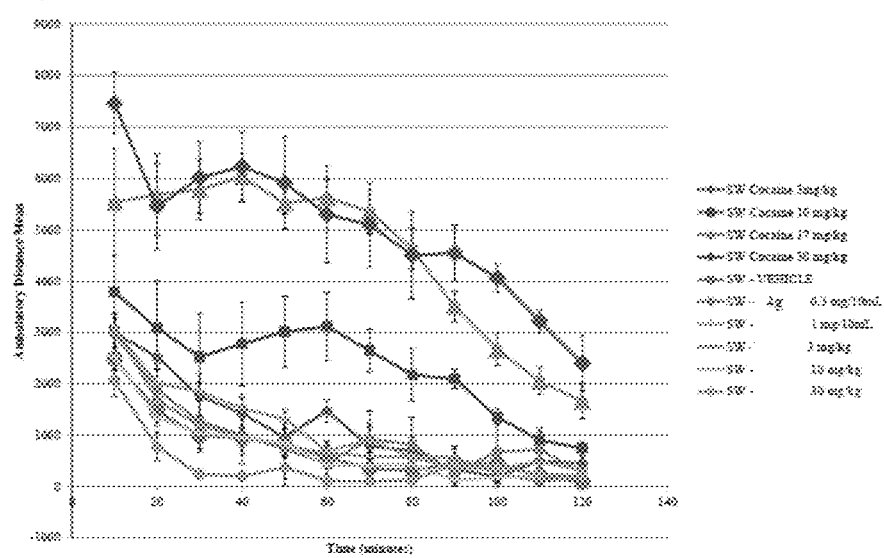
FIG. 2: Ambulatory distance mean±standard deviation for compound 4g versus cocaine.

Compound 4g was evaluated in a mouse locomotor activity test versus cocaine at using Swiss Webster mice. Cocaine was administered at 3, 10, 17, and 30 mg/kg while compound 4g was administered at 0.3 and 1 mg/10 ml and 3, 10 and 30 mg/kg. The data (FIG. 2) show that compound 4g, up to 30 mg/kg, does not produce locomotor stimulation, unlike cocaine. This compound, and those disclosed herein, have potential for the treatment of cocaine and methamphetamine abuse.

Example 8

Metabolic Stability of Compound 4g in Mouse Plasma and Mouse Liver Microsomes The metabolic stability was evaluated using mouse plasma and mouse liver microsomes. For plasma stability, compound (10 µM) was spiked in plasma and reaction (100 µL) was stopped at 0, 15, 30 and 60 min by addition of acetonitrile (300 µL) spiked with internal standard (10 µM, losartan).

Phase I and phase II metabolic stability assay for was conducted in mouse liver microsomes. For phase I metabolism, the reaction was carried out with 100 mM potassium phosphate buffer, pH 7.4, in the presence of NADPH regenerating system (1.3 mM NADPH, 3.3 mM glucose 6-phosphate, 3.3 mM $MgCl_2$, 0.4 U/mL glucose-6-phosphate dehydrogenase, 50 µM sodium citrate). Reactions in duplicate were initiated by addition of the liver microsomes to the incubation mixture (compound final concentration was 10 µM; 0.5 mg/mL microsomes). For phase II glucuronidation reaction compound was added to TRIS-HCl buffer (50 mM, pH 7.5) with microsomes (0.5 mg/mL), along with $MgCl_2$ (8 mM), and alamethicin (25 µg/mL) and pre-incubated at 37° C. The reaction was initiated (in duplicate) with UDPGA at a final concentration of 2 mM. Negative controls in the absence NADPH and UDPGA were carried for both phase I and phase II metabolism respectively, to determine the specific cofactor free degradation. Positive control for plasma (procaine), phase I (testosterone) and phase II (4-methylumbelliferone) were also added. At predetermined times (0, 15, 30 and 60 min) aliquots of the mixture were removed and the reaction quenched by addition of two times the volume of ice cold acetonitrile spiked with the internal standard. Compound disappearance was monitored over time using a liquid chromatography and tandem mass spectrometry (LC/MS/MS) method.

Compounds were separated on an Agilent 1290 UPLC system with a c18 column using a gradient run of 55:45-5:95 water:acetonitrile over 3.2 minutes and detected on an Agilent 6520 QTOF mass spectrometer. The results are provided in Tables 8 and 9 below.

TABLE 8

Metabolic stability results for compound 4g in plasma and mouse liver microsomes

| Time | Plasma | Phase I | Phase II | Negative Control |
|---|---|---|---|---|
| 0 | 100% | 100% | 100% | 100% |
| 15 | 100% | — | 90% | 104% |
| 30 | 99% | 95% | 77% | 97% |
| 60 | 103% | 77% | 50% | 119% |

TABLE 9

Positive controls: Procaine (plasma), Testosterone (Phase I) and 4-Methyl umbelliferone (Phase II)

| Time | Procaine | Testosterone | 4 Methyl Umbelliferone |
|---|---|---|---|
| 0 | 100% | 100% | 100% |
| 60 | 9.70% | 0% | 3.10% |

Compound 4g was found to be stable in mouse plasma over a period of 60 minutes. However, in mouse liver microsomal incubations in the presence of NADPH, compound 4g was metabolized with 77% remaining after 60 minutes of incubation. Also, in microsomes fortified with UDPGA, compound 4g was rapidly metabolized with 50% of the parent compound remaining after 60 minutes of incubation. No metabolism was observed in microsomes without the cofactors showing their specificity to CYP and UGT dependent instability.

Example 9

Pharmacokinetics of Compound 4g in Mice

In vivo pharmacokinetics was evaluated by dosing compound 4g at 10 mg/kg orally (p.o.) and intravenously (i.v.) to male CD1 mice, 6-8 weeks old, and weighing 20-25 g. The dosing solution for compound 4g was prepared in 10% DMSO, 15% Tween 80 and 75% saline to a concentration of 1 mg/ml. Following administration, blood was obtained via cardiac puncture at 5, 15 min, 30 min, 1 h, 2 h, and 4 h post dose (n=3 per time point). Plasma was harvested from blood by centrifugation. Additionally at two selected time points (i.e. 30 min and 2 h) brains were collected following both oral and IV dosing. Samples were extracted from plasma by a single one-step protein precipitation method (as described in bioanalysis section below). For brain tissue, whole brains were weighed and homogenized in two times the volume of acetonitrile, followed by vortexing and centrifugation. Once extracted, the samples were analyzed via LC/MS/MS (as described in bioanalysis section below). Non-compartmental-analysis module in WinNonlin™ (version 5.3) was used to assess pharmacokinetic parameters including maximal concentration (Cmax), time to Cmax (Tmax), area under the curve (AUClast), area extrapolated to infinity (AUC0-∞), terminal disposition rate constant (ke), and terminal half-life (t½).

Bioanalysis of compound 4g: Calibration standards were prepared in mouse plasma or mouse brain spiked with compound 4g (Std Curve 1. 50-50,000 nM, Std Curve 2. 1-1000 nM). Briefly, plasma samples were thawed on ice prior to extraction. Samples (50 µL) were extracted in 300 µL acetonitrile containing 1000 nM losartan as internal standard. For brain, 50 µL of the supernatant from homogenized tissue was extracted with 100 µL acetonitrile containing 1000 nM losartan as internal standard. Extracts were centrifuged at 16000×g at 4° C. for 10 minutes. Supernatants were transferred to a new siliconized tube and dried under $N_2$ at 45° C. for 30 min. Samples were reconstituted with 100 µL of 30% acetonitrile, vortexed and centrifuged. Supernatants (95 µL) were transferred to a 250 µL polypropylene autosampler vials sealed with a Teflon cap and a volume of 10 µL was injected onto the ultra-performance liquid chromatography (UPLC) instrument for quantitative analysis using a temperature-controlled autosampler operating at 10° C.

The mass spectrometer was operated with an ESI interface in positive ionization mode for compound 4g. The instrument was controlled by the Xcalibur software 2.3 (Thermo Scientific). Samples were introduced to the interface through Turbo Ion Spray with the temperature setting at 350° C. A high positive voltage of 4.0 kV was applied to the ion spray. Nitrogen was used as the sheath and auxiliary gas, and argon as a collision gas with the settings of 40, 10 and 10, respectively. Quantification was performed in multiple-reaction monitoring (MRM) mode using transitions of m/z 398.404→183.357, 203.38 for 4g and m/z 423.69→180.36, 207.39 for losartan (internal standard).

Chromatographic analysis was performed using an Accela™ ultra high-performance system consisting of an analytical pump, and an autosampler coupled with TSQ Vantage mass spectrometer (Thermo Fisher Scientific Inc., Waltham Mass.). Separation of the analyte from potentially interfering material was achieved at ambient temperature using Agilent Eclipse Plus column (100×2.1 mm i.d.) packed with a 1.8 μm $C_{18}$ stationary phase. The mobile phase used was composed of 0.1% Formic Acid in Acetonitrile and 0.1% Formic Acid in $H_2O$ with gradient elution, starting with 10% (organic) linearly increasing to 99% up to 2.5 min, maintaining at 99% (2.5-3.5 min) and reequlibrating to 10% by 4.5 min. The total run time for each analyte was 4.5 min.

Figure 3:
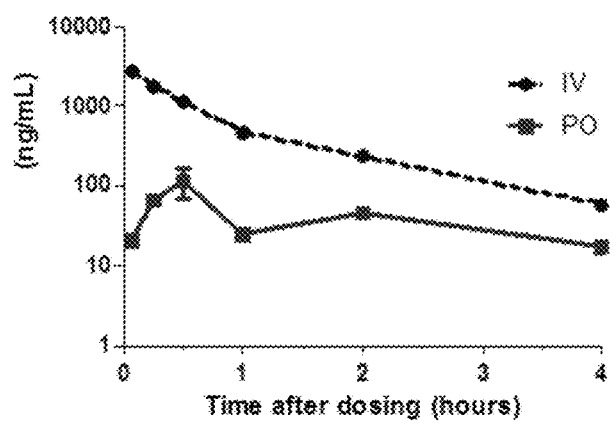
FIG. 3: Mean concentration profiles for compound 4g in mouse plasma following P.O. (◆) and I.V. (■) administration of 10 mg/kg.

Plasma concentration-time profiles of compound 4g in mice after i.v. and p.o. dosing are shown in FIG. 3. A summary of the plasma pharmacokinetic parameters is listed in Table 10. Absorption was relatively rapid for compound 4g as it was detectable at the earliest blood sampling point (5 min); the peak plasma concentration ($C_{max}$) for compound 4g was 116 ng/mL the terminal half-life ($t_{1/2}$) were approximately 1 hour. The average absolute bioavailability was low/moderate with compound 4g at approximately 10%. Compound 4g showed excellent brain penetrability following both p.o. and i.v. dosing as shown in Table 11. Brain to plasma ratio ranged from 4-60 fold. Additionally, following i.v. administration accumulation of compound 4g in brain was also observed. The results of this study and in Example 8 demonstrate that in total, compound 4g has reasonable bioavailability, especially due to its very high blood-brain barrier penetration.

TABLE 10

Noncompartmental PK parameters for compound 4g in mouse plasma following 10 mg/kg I.V. and P.O. administration in mice

| | $C_{max}^a$ (ng/mL) | $T_{max}^a$ (h) | $AUC_{last}^a$ (h*ng/mL) | $(AUC_{inf})^a$ (h*μg/mL) | $K_e$ | $t_{1/2}^a$ (h) | F % |
|---|---|---|---|---|---|---|---|
| Plasma (IV) | 2740 | 0.08 | 1956 | 2041 | 0.6952 | 0.997 | |
| Plasma PO | 116 | 0.5 | 155.48 | 202.83 | N.C.[b] | N.C.[b] | 9.89% |

[a]Data are presented as mean.; n = 3 mice per time point
[b]Not Calculated

TABLE 11

Brain concentrations of compound 4g in mouse brain following IV and PO dosing at 10 mg/kg

| Time (h) | IV (Conc. ng/g ± SD*) | PO (Conc. ng/g ± SD) |
|---|---|---|
| 0.5 | 4776 (1324) | 369 (303) |
| 2 | 14111 (8093) | 223 (90) |

*Std. Deviation

The terms "a" and "an" do not denote a limitation of quantity, but rather denote the presence of at least one of the referenced item. The term "or" means "and/or". Reference throughout the specification to "one embodiment", "another embodiment", "an embodiment", and so forth, means that a particular element (e.g., feature, structure, and/or characteristic) described in connection with the embodiment is included in at least one embodiment described herein, and may or may not be present in other embodiments. In addition, it is to be understood that the described elements may be combined in any suitable manner in the various embodiments. The modifier "about" used in connection with a quantity is inclusive of the stated value and has the meaning dictated by the context (e.g., includes the degree of error associated with measurement of the particular quantity).

The endpoints of all ranges directed to the same component or property are inclusive of the endpoints, are independently combinable, and include all intermediate points and ranges (e.g., ranges of "up to about 25 wt. %, or, more specifically, about 5 wt. % to about 20 wt. %," is inclusive of the endpoints and all intermediate values of the ranges of "about 5 wt. % to about 25 wt. %," such as about 10 wt % to about 23 wt %, etc.).

All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein. Unless defined otherwise, technical and scientific terms used herein have the same meaning as is commonly understood by one of skill in the art to which this invention belongs.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

REFERENCES

1. Loland et. al. Biological Psychiatry 2012, 72, 405-413.
2. Schmitt and Reith PLoS ONE 2011, 6(10): e25790.
3. Mahler et. al. Addiction Biol. 2012 Sep. 27. doi: 10.1111/j.1369-1600.2012.00506.x. [Epub ahead of print].
4. Tahsili-Fahadan, Malcolm and Aston-Jones, Neuropsychopharmacology Reviews 2010, 35, 343-344.
5. Reichel and See, Psychopharmacology 2010, 210, 337-346; International Journal of Neuropsychopharmacology 2012, 15, 919-929.
6. Minzenberg and Carter, Neuropsychopharmacology 2008, 33, 1477-1502.
7. Scoriels et. al., Neuropharmacology 2013, 64, 168-184.
8. Cao et al. ACS Medicinal Chemistry Letters 2011, 2, 48-52.
9. Newman and Katz Topics in Medicinal Chemistry 2009, 4, 95-129.

What is claimed is:

1. A compound or salt of formula V:

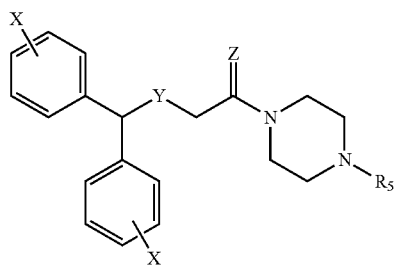

Formula V wherein
R$_5$ is hydrogen, C$_1$-C$_6$alkyl, C$_2$-C$_6$alkenyl, C$_3$-C$_7$cycloalkyl, (C$_3$-C$_7$cycloalkyl)C$_0$-C$_6$alkyl, (C$_3$-C$_7$cycloalkenyl)C$_0$-C$_6$alkyl, (heterocycloalkyl)C$_0$-C$_6$alkyl, (aryl)C$_0$-C$_6$alkyl, or (mono- or bicyclic heteroaryl)C$_0$-C$_6$alkyl, wherein each alkyl portion independently can optionally be substituted with a hydroxyl group;

X is independently chosen at each occurrence from halogen, hydroxyl, amino, nitro, cyano, C$_1$-C$_6$ alkyl, —COOH, —CHO, —CONH$_2$, C$_1$-C$_6$alkoxy, C$_2$-C$_6$alkanoyl, mono- or di-C$_1$-C$_2$alkylamino, C$_1$-C$_2$haloalkyl, or C$_1$-C$_2$haloalkoxy;

Y is S, S(O), or S(O)$_2$; and
Z is O, S, or 2H.

2. The compound or salt of claim 1, wherein
R$_5$ is 3-phenylpropyl, —CH$_2$CH(OH)CH$_3$, or —CH$_2$CH(OH)CH$_2$Ph;
each instance of X is located at the para or meta position and is fluoro, methyl, or CF$_3$;
Y is S or S(O); and
Z is O or 2H.

3. The compound or salt of claim 1, wherein a sulfoxide fragment has an (R)-configuration.

4. A pharmaceutical composition comprising a compound or salt of claim 1, containing at least one pharmaceutically acceptable carrier.

5. The pharmaceutical composition of claim 4, wherein the composition is formulated as an injectable fluid, an aerosol, a cream, a gel, a tablet, a pill, a capsule, a syrup, an ophthalmic solution, or a transdermal patch.

6. A package comprising the pharmaceutical composition of claim 5 in a container and further comprising instructions for using the composition in order to elicit a wake-promoting, cognition-enhancing or mood-enhancing effect in a patient.

7. A package comprising the pharmaceutical composition of claim 5 in a container and further comprising instructions for using the composition to treat a patient suffering from substance use disorders, attention deficit (hyperactivity) disorder, depressive disorders, sleep disorders or cognitive impairment.

8. The compound or salt of claim 1, wherein a sulfoxide fragment has an (S)-configuration.

9. The compound or salt of claim 1, wherein
R$_5$ is —CH$_2$CH(OH)CH$_3$ or —CH$_2$CH(OH)CH$_2$Ph wherein the carbon substituted with —OH is racemic, in the R configuration, or in the S configuration;
each instance of X is located at the para or meta position and is fluoro, methyl, or CF$_3$;
Y is S or S(O); and
Z is 2H.

10. The compound or salt of claim 9, wherein a sulfoxide fragment has an (R)-configuration or an (S)-configuration.

11. The compound or salt of claim 1, wherein
R$_5$ is —CH$_2$CH(OH)CH$_3$ or —CH$_2$CH(OH)CH$_2$Ph wherein the carbon substituted with —OH is racemic, in the R configuration, or in the S configuration;
each instance of X is located at the para or meta position and is fluoro;
Y is S or S(O); and
Z is 2H.

12. The compound or salt of claim 11, wherein a sulfoxide fragment has an (R)-configuration or an (S)-configuration.

13. A compound or salt of formula V:

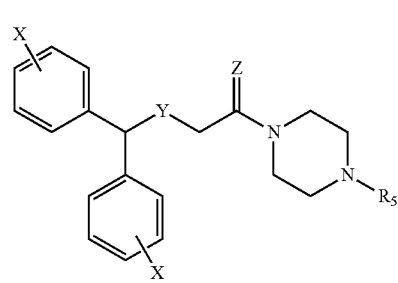

Formula V wherein
R$_5$ is hydrogen, C$_1$-C$_6$alkyl, C$_2$-C$_6$alkenyl, C$_3$-C$_7$cycloalkyl, (C$_3$-C$_7$cycloalkyl)C$_0$-C$_6$alkyl, (C$_3$-C$_7$cycloalkenyl)C$_0$-C$_6$alkyl, (heterocycloalkyl)C$_0$-C$_6$alkyl, (aryl)C$_0$-C$_6$alkyl, or (mono- or bicyclic heteroaryl)C$_0$-C$_6$alkyl, wherein each alkyl portion independently can optionally be substituted with a hydroxyl group;

X is independently chosen at each occurrence from hydroxyl, amino, nitro, cyano, C$_1$-C$_6$ alkyl, —COOH, —CHO, —CONH$_2$, C$_1$-C$_6$alkoxy, C$_2$-C$_6$alkanoyl, mono- or di-C$_1$-C$_2$alkylamino, C$_1$-C$_2$haloalkyl, or C$_1$-C$_2$haloalkoxy;

Y is O, S, S(O), or S(O)$_2$; and
Z is O or S.

14. The compound or salt of claim 13, wherein
R$_5$ is 3-phenylpropyl, —CH$_2$CH(OH)CH$_3$, or —CH$_2$CH(OH)CH$_2$Ph;
each instance of X is located at the para or meta position and is methyl or CF$_3$;
Y is S or S(O); and
Z is O.

15. The compound or salt of claim 13, wherein
R$_5$ is —CH$_2$CH(OH)CH$_3$ or —CH$_2$CH(OH)CH$_2$Ph wherein the carbon substituted with —OH is racemic, in the R configuration, or in the S configuration;
each instance of X is located at the para or meta position and is methyl or CF$_3$;
Y is S or S(O); and
Z is O.

16. The compound or salt of claim 15, wherein a sulfoxide fragment has an (R)-configuration or an (S)-configuration.

* * * * *